US011096753B1

(12) United States Patent
Mantri et al.

(10) Patent No.: US 11,096,753 B1
(45) Date of Patent: *Aug. 24, 2021

(54) SYSTEMS AND METHODS FOR DEFINING AND MODIFYING RANGE OF MOTION OF PROBE USED IN PATIENT TREATMENT

(71) Applicant: PROCEPT BioRobotics Corporation, Redwood City, CA (US)

(72) Inventors: Surag Mantri, East Palo Alto, CA (US); Kevin Patrick Staid, Lowell, MA (US); Jason Hemphill, Los Gatos, CA (US); Kevin Louis Hudelson, Fremont, CA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/939,880

(22) Filed: Jul. 27, 2020

Related U.S. Application Data

(60) Provisional application No. 63/044,843, filed on Jun. 26, 2020.

(51) Int. Cl.
*A61B 34/37* (2016.01)
*A61B 34/00* (2016.01)
(Continued)

(52) U.S. Cl.
CPC .............. *A61B 34/70* (2016.02); *A61B 34/25* (2016.02); *A61B 34/37* (2016.02); *A61B 90/03* (2016.02);
(Continued)

(58) Field of Classification Search
CPC ......... A61B 34/30; A61B 34/37; A61B 34/35; A61B 34/20; A61B 2034/301;
(Continued)

(56) References Cited

U.S. PATENT DOCUMENTS

| 4,932,956 A | 6/1990 | Reddy |
| 7,021,173 B2 | 4/2006 | Stoianovici |

(Continued)

FOREIGN PATENT DOCUMENTS

| WO | 2008083407 | 7/2008 |
| WO | 2009111736 | 9/2009 |

(Continued)

OTHER PUBLICATIONS

Dwyer et al., A miniaturised robotic probe for real-time intraoperative fusion of ultrasound and endomicroscopy, 2015, IEEE, pg. (Year: 2015).*

(Continued)

*Primary Examiner* — McDieunel Marc
(74) *Attorney, Agent, or Firm* — FisherBroyles LLP; John Shimmick

(57) ABSTRACT

A system for treating a target tissue of a patient comprises a first robotic arm coupled to a treatment probe for treating the target tissue of the patient, and a second robotic arm coupled to an imaging probe for imaging the target tissue of the patient. The system further comprises one or more computing devices operably coupled with the first robotic arm and the second robotic arm, the one or more computing devices configured to execute instructions for controlling movement of one or more of the first robotic arm or the second robotic arm. The distal end of the treatment probe and/or imaging probe is constrained to be moved only within an allowable range of motion.

20 Claims, 30 Drawing Sheets

(51) Int. Cl.
*A61B 90/00* (2016.01)
*B25J 9/02* (2006.01)
*B25J 9/16* (2006.01)
*A61B 34/30* (2016.01)

(52) U.S. Cl.
CPC .......... *A61B 90/361* (2016.02); *A61B 90/37* (2016.02); *B25J 9/02* (2013.01); *B25J 9/1664* (2013.01); *A61B 2034/301* (2016.02)

(58) Field of Classification Search
CPC .......... A61B 90/361; A61B 2034/2055; A61B 2034/305; A61B 34/70; A61B 2090/3937; A61B 17/00234; A61B 34/25; A61B 90/37; A61B 2090/3983; A61B 34/74; A61B 34/76; A61B 17/0218; A61B 1/00149; A61B 1/00193; A61B 1/05; A61B 90/50; A61B 90/98; A61B 18/1445; A61B 2090/371; A61B 1/00087; A61B 2034/742; A61B 34/00; A61B 17/29; A61B 1/3132; A61B 2505/05; A61B 18/1477; A61B 1/00045; A61B 2017/3409; A61B 17/062; A61B 17/32; A61B 17/3201; A61B 17/34; A61B 18/1402; A61B 1/00006; A61B 1/00009; A61B 17/0483; A61B 17/1285; A61B 2017/00115; A61B 2017/00199; A61B 2017/00075; A61B 8/4444; B25J 9/1689; B25J 19/021; B25J 9/06; B25J 13/025; B25J 19/023; Y10T 74/20305; A61F 2002/30785; A61F 2002/30892; G06F 19/00; G06F 3/016; G06F 3/0346; G06F 3/011; G05B 19/00; G05B 2219/40174; G05B 2219/50391; G06N 20/00; G06N 5/04; Y10S 901/02; Y10S 901/15

See application file for complete search history.

(56) References Cited

U.S. PATENT DOCUMENTS

| | | | |
|---|---|---|---|
| 7,882,841 | B2 | 2/2011 | Aljuri |
| 8,398,541 | B2 * | 3/2013 | DiMaio .................. A61B 34/76 |
| | | | 600/111 |
| 8,814,921 | B2 | 8/2014 | Aljuri |
| 8,827,948 | B2 | 9/2014 | Romo |
| 8,961,533 | B2 | 2/2015 | Stahler |
| 9,314,306 | B2 | 4/2016 | Yu |
| 9,364,251 | B2 | 6/2016 | Aljuri |
| 9,610,131 | B2 | 4/2017 | Stoianovici |
| 9,737,371 | B2 | 8/2017 | Romo |
| 9,867,635 | B2 | 1/2018 | Alvarez |
| 9,877,788 | B2 | 1/2018 | Stoianovici |
| 10,130,427 | B2 | 11/2018 | Tanner |
| 10,231,867 | B2 | 3/2019 | Alvarez |
| 10,555,780 | B2 | 2/2020 | Tanner |
| 10,555,785 | B2 | 2/2020 | Yeung |
| 10,646,295 | B2 | 5/2020 | Stoianovici |
| 2004/0024311 | A1 | 2/2004 | Quaid |
| 2012/0071894 | A1 | 3/2012 | Tanner |
| 2014/0039314 | A1 | 2/2014 | Stoianovici |
| 2014/0194896 | A1 | 7/2014 | Frimer |
| 2014/0309649 | A1 | 10/2014 | Alvarez |
| 2015/0025539 | A1 | 1/2015 | Alvarez |
| 2016/0262827 | A1 | 9/2016 | Ross |
| 2017/0020253 | A1 | 1/2017 | Drozdowicz |
| 2017/0202537 | A1 | 7/2017 | Ippolito |
| 2017/0245878 | A1 | 8/2017 | Aljuri |
| 2017/0245949 | A1 | 8/2017 | Randle |
| 2018/0014891 | A1 | 1/2018 | Krebs |
| 2018/0021960 | A1 | 1/2018 | Grant |
| 2018/0263647 | A1 | 9/2018 | Aljuri |
| 2018/0263685 | A1 | 9/2018 | Onik |
| 2018/0353253 | A1 | 12/2018 | Bowling |
| 2019/0076674 | A1 | 3/2019 | Ergün |
| 2019/0105023 | A1 | 4/2019 | Aljuri |
| 2019/0105117 | A1 * | 4/2019 | Brisson .................. A61B 34/30 |
| 2019/0142396 | A1 | 5/2019 | Stoianovici |
| 2019/0321119 | A1 | 10/2019 | Yeung |
| 2019/0336238 | A1 | 11/2019 | Yu |
| 2020/0008874 | A1 * | 1/2020 | Barbagli ................. G16H 20/40 |
| 2020/0261297 | A1 | 8/2020 | Strydom |
| 2020/0360097 | A1 * | 11/2020 | DiMaio ................. H04N 5/2253 |
| 2020/0360100 | A1 * | 11/2020 | Mantri .................... A61B 90/37 |
| 2021/0030496 | A1 | 2/2021 | Devengenzo |

FOREIGN PATENT DOCUMENTS

| | | |
|---|---|---|
| WO | 2011097505 | 8/2011 |
| WO | 2013130895 | 9/2013 |
| WO | 2014127242 | 8/2014 |
| WO | 2014165703 | 10/2014 |
| WO | 2015035249 | 3/2015 |
| WO | 2015200538 | 12/2015 |
| WO | 2016004071 | 1/2016 |
| WO | 2016037132 | 3/2016 |
| WO | 2016037137 | 3/2016 |
| WO | 2017161331 | 9/2017 |
| WO | 2019032986 | 2/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |

OTHER PUBLICATIONS

Christoforou et al., Robotic Arm for Magnetic Resonance Imaging Guided Interventions, 2006, IEEE, p. 1-6 (Year: 2006).*

Marmol et al., ArthroSLAM: Multi-Sensor Robust Visual Localization for Minimally Invasive Orthopedic Surgery, 2018, IEEE, p. 3882-3889 (Year: 2018).*

Rosa et al., Laparoscopic optical biopsies: In vivo robotized mosaicing with probe-based confocal endomicroscopy, 2011, IEEE, p. 1339-1345 (Year: 2011).*

Lim et al. "Robotic Transrectal Ultrasound-Guided Prostate Biopsy." IEEE Trans BME. Jan 7, 2019. 11 pages. (Year: 2019).

Stoianovici et al. "MRI-Safe Robot for Endorectal Prostate Biopsy." IEEE/ASME Trans Mechatronics, vol. 19, No. 4 Aug. 2014. pp. 1289-1299. (Year: 2014).

Office Action (final) for U.S. Appl. No. 16/939,972, 13 pages (dated Jan. 8, 2021).

Office Action (final) for U.S. Appl. No. 16/940,100, 12 pages (dated Mar. 23, 2021).

Response to Non-Final Office Action for U.S. Appl. No. 16/940,085, 8 pages (dated Mar. 2, 2021).

Response to Non-Final Office Action for U.S. Appl. No. 16/940,100, 8 pages (dated Mar. 11, 2021).

Notice of Allowance for U.S. Appl. No. 16/939,972, 12 pages (dated May 13, 2021).

Office Action (Final) for U.S. Appl. No. 16/940,085, 14 pages (dated Apr. 13, 2021).

Response to Final Office Action for U.S. Appl. No. 16/940,085, 8 pages (dated Jun. 3, 2021).

* cited by examiner

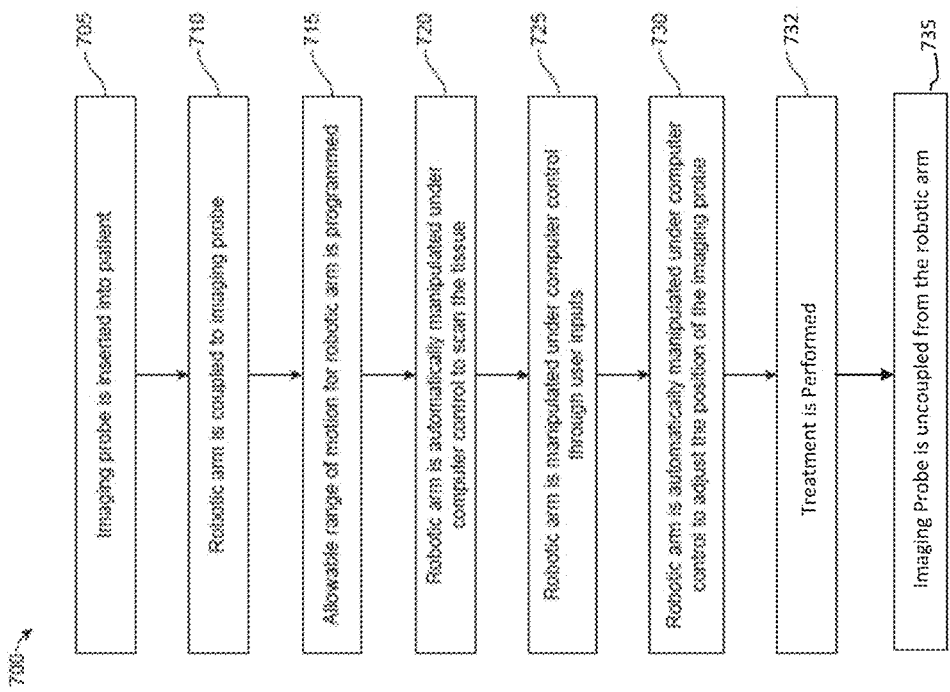

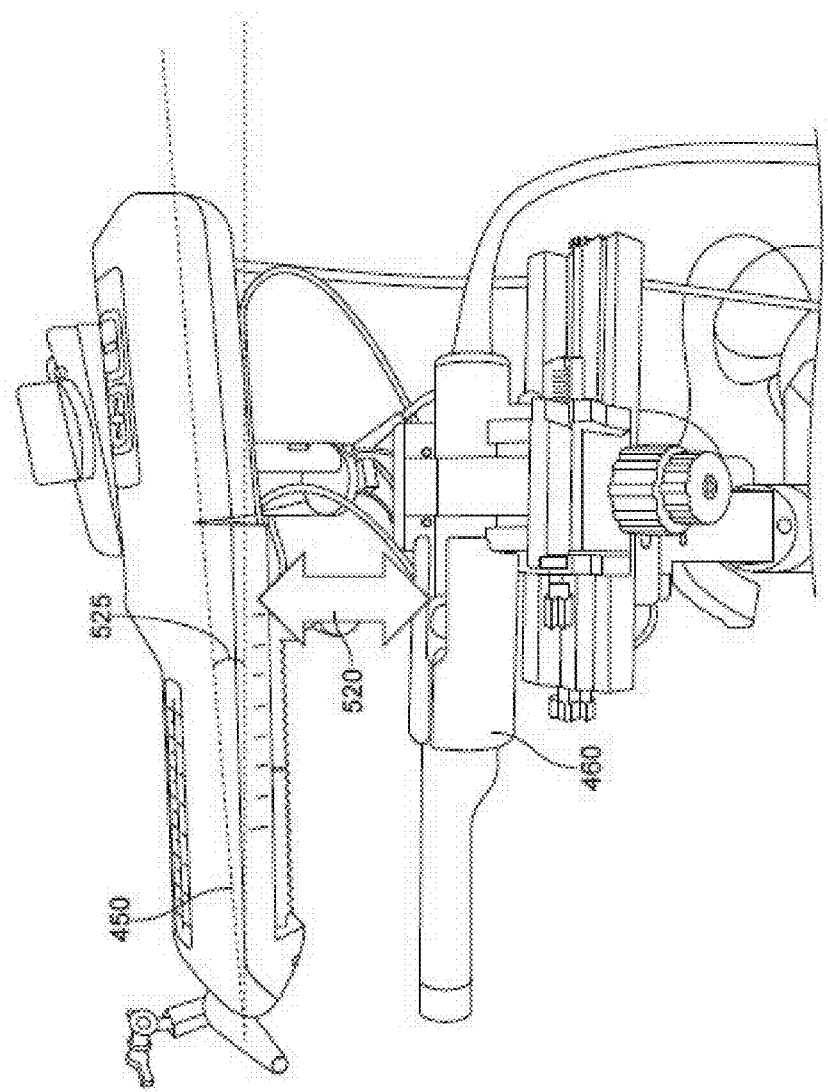

SYSTEMS AND METHODS FOR DEFINING AND MODIFYING RANGE OF MOTION OF PROBE USED IN PATIENT TREATMENT

CROSS-REFERENCE TO RELATED APPLICATIONS

This application claims the benefit under 35 U.S.C. § 119(e) of U.S. Provisional Patent Application No. 63/044,843 filed Jun. 26, 2020, and titled "System and Methods for Defining and Modifying Range of Motion of Probe Uses in Patient Treatment", which is incorporated, in its entirety, by this reference.

The subject matter of this patent application is related to International Application No. PCT/US2015/048695, filed Sep. 4, 2015, and International Application No. PCT/US2020/021756, filed Mar. 9, 2020, entitled "ROBOTIC ARMS AND METHODS FOR TISSUE RESECTION AND IMAGING, the entire contents of which applications are incorporated herein by reference.

BACKGROUND

The field of the present disclosure is related to the treatment of tissue with energy, and more specifically to the treatment of an organ such as the prostate with fluid stream energy.

Prior methods and apparatus of treating subjects such as patients can result in less than ideal tissue removal in at least some instances. For example, prior methods of surgery such as prostate surgery can result in longer healing time and a less than desirable outcome than would be ideal in at least some instances.

Prior methods and apparatus of imaging tissue can be less than ideal for imaging a treated tissue. For example, prior ultrasound methods and apparatus may not be well suited to view the treatment site during treatment, and alignment of diagnostic images with treatment images can be less than ideal. Also, at least some of the prior treatment methods and apparatus of treating tissue may not be well suited for combination with imaging systems of the prior art. In at least some instances, it would be helpful to provide improved imaging of tissue during surgery, for example to provide real time imaging of tissue that would allow a user to adjust the treatment based on real time images of the tissue. At least some of the prior methods and apparatus to image tissue during surgery can be somewhat cumbersome to use and can result in delays in the patient treatment.

Prior methods and apparatus to treat an organ such as the prostate may provide a user interface that is somewhat cumbersome for the user and can provide less than ideal planning of the surgery, such as by not providing sufficient images of probes and treatment areas, not providing "fine" enough controls of probes or not providing indications of constraints on probe motion that may impact the planning process, etc. Also, at least some of the prior methods and apparatus used to treat tissue such as the prostate tissue can be somewhat less accurate than would be ideal, such as by showing inaccuracies in the placement of an organ, mis-identifying tissue, creating uncertainty as to whether the application of a treatment is to the correct area or region, etc. In at least some instances, the prior methods and apparatus may provide a less than ideal user experience (for example, excessive manual operations which could be accomplished automatically). Also, at least some of the prior interfaces may provide less than ideal coupling of the treatment apparatus with tissue structures (for example, by lacking images and/or controls that would enable more accurate and informed control of a treatment procedure by a physician).

For at least the reasons mentioned, prior methods and apparatus of treating tissue with robotic instrumentation can be less than ideal during a treatment. The robotic arms and surgical probes of a robotic surgery system may be aligned with one another and with the patient prior to the treatment. In some instances, the robotic arms and surgical probes are first manually moved and positioned before they are coupled to each other and locked in position for further controller-based adjustments. For example, a surgical probe or other tool coupled to a robotic arm may be manually guided through the anatomy to reach a target site, such as through the anus and rectum in the case of transrectal ultrasound ("TRUS"), or through the tortuous path of the urethra, prostate, and bladder neck which involves sharp turns through sensitive anatomy. In at least some instances, the maintenance of the desired alignment and the stability of the robotic arms after the manual adjustment and during treatment can be less than ideal. For example, the prior robotic arms and end surgical probes could be held too rigidly which could potentially lead to tissue injury related to patient movement, or may be held with less than ideal support strength, which could lead to less than ideal alignment with the target site if the robotic arms and surgical probes were to be disturbed, e.g. upon being bumped or being released from the grasp of a user subsequent to coupling.

A further disadvantage of prior methods and apparatus of treating tissue with robotic instrumentation is that the probes and devices used for treatment, and in some cases for monitoring treatment, have a range of possible motions that in some cases, could cause the probes and devices to collide with each other during treatment in some instances. This could potentially lead to a less than ideal outcome and an interruption in the treatment. The prior approaches can be somewhat limited in the ability to customize the allowable range of motion for an individual patient, even though the absolute and relative positions of the robotic arms may be known.

Work in relation to the present disclosure suggests that prior approaches to aligning probes with robotic arms can be less than ideal in at least some instances.

While these aforementioned methods and apparatuses can be effective and may represent a significant advance over prior luminal tissue treatment approaches, it would be desirable to provide improvements to assist in more accurate tissue removal in both fully automated and physician assisted operating modes. At least some of these limitations of the prior approaches will be overcome in accordance with embodiments of the present disclosure.

SUMMARY

Embodiments of the present disclosure provide improved movement of robotic arms and are well suited for use with surgical procedures. In some embodiments, a robotic arm is configured to enter into a teaching or training mode that can allow range of motion limits or constraints to be established for a probe inserted into a patient. The probe coupled to the robotic arm can be moved within the patient by an operator to establish positions that are appropriate for the patient and the treatment. Also, the pivot location of the probe can be established. With prostate surgery, the pivot location of a surgical probe inserted into the patient can be established so as to correspond to the pubic bone. Similarly, the TRUS or imaging probe can be inserted into the patient to establish ranges of motion and a pivot location at a location corresponding to the rectum. Because patient anatomy can vary, establishing ranges of motion for probes and their associated pivots can be helpful. In some embodiments, a pivot location corresponding to the rectum can be located caudal or cephalad to the pivot location corresponding to the treatment probe. Once the ranges of motion and pivot locations have been established, the operator can then precisely position the probes under robotic control. The imaging probe can also be used to determine the position and orientation of the treatment probe, with that information being used to limit movement of the treatment probe toward the imaging probe. Although reference will be made to use of robotic arms and probes for purposes of imaging and treatment, the systems and methods described herein may also be used for diagnostic purposes, as part of treatment planning, as part of post-treatment examination, etc.

Embodiments of the present disclosure provide improved methods and apparatus for performing tissue treatment such as, but not limited to tissue resection. In some embodiments, an image-guided treatment system comprises a treatment probe and an imaging probe. The imaging probe may be configured to provide an image of the target site while the treatment probe performs resection or other treatment of the target tissue. In some embodiments, the treatment probe and the imaging probe are each coupled to robotic arms under control of one or more computing devices. The treatment probe may be coupled to a first robotic arm configured to provide computer-controlled movement of the treatment probe during tissue resection with the treatment probe. The imaging probe may be coupled to a second robotic arm configured to provide computer-controlled movement of the imaging probe during scanning of the target site with the imaging probe, before and/or during the tissue resection procedure with the treatment probe. One or more computing devices or processors may be configured to execute instructions for operating the robotic arms in a passive mode in which the robotic arms are configured to be manually adjusted to position the treatment and imaging probes to a manually-set position, such as for imaging and treatment of the same or different tissue sites. The one or more computing devices may be configured to execute instructions for maintaining the manually set position(s) of the probes after the robotic arms are released from the manual adjustment or passive mode. The robotic arms may be configured to maintain the manually set position with respect to one or more of a translational axis or a rotational axis. In some embodiments, the rotational angle is maintained to within 5° and the translational position to within 5 mm, or less. In some embodiments, the rotational angle and translational position are maintained for each of three axes, which can improve the accuracy of imaging and treatment with a probe.

The one or more computing devices operably coupled to the first and second robotic arms may be configured to automatically control the movement of the treatment probe and/or the imaging probe, for example based on a pre-planned or programmed scanning profile, or according to various pre-programmed parameters. The treatment pre-planning may be performed manually and/or with the assistance of one or more of computer vision, image recognition, or machine learning. The automatically controlled movement of the treatment probe in accordance with a treatment profile can perform treatment of the target site, for example. The automatically controlled movement of the image probe in accordance with an imaging profile can generate a 3-dimensional rendering of the target site, for example. The automatic, computer-controlled scanning or monitoring of the target site with the imaging probe using the robotic arm can also be used to generate useful information regarding the target site for purposes of preventing harm to the patient or for additional treatment. For example, the imaging probe may be configured to perform a color/Doppler scan of the target site after a resection procedure, in order to locate bleeding sites within the target site that require hemostasis. As another example, the imaging probe may be configured to perform a color/Doppler scan of the target site before a resection or other procedure, in order to locate blood vessels and enabling the surgical planning to avoid potential bleeding sites, thereby avoiding a post procedure requirement for hemostasis treatment. The 3-dimensional scan of the target site using the imaging probe may also be used to identify tissue anomalies at the target site, such as tumors. A scan or imaging may also be performed pre or post-operation or treatment and compared to a later scan or image to identify bleeding or other issues.

Alternatively, or additionally, the one or more computing devices may be configured to control movement of the treatment probe and/or the imaging probe in response to user inputs, for example through a graphical user interface of the treatment apparatus. In some embodiments, the one or more computing devices may be configured to limit the movement of the treatment probe and/or imaging probe within an allowable range of motion, which may be programmed into the first and/or second robotic arm prior to initiating use of the first or second arm under computer control.

In some embodiments, the disclosure is directed to a system for treating or imaging tissue of a patient. In these embodiments, the system may include a probe sized for insertion into the patient, a robotic arm configured to couple to the probe, one or more computing devices operatively coupled to the robotic arm and configured with instructions for establishing an allowable range of motion for the probe, with the allowable range of motion stored on a memory of the one or more computing devices. In these embodiments, establishing the allowable range of motion includes defining a possible range of motion for a distal end of the probe and modifying the possible range of motion of the distal end of the probe to define an allowable range of motion for the distal end of the probe for an individual patient. In some embodiments, this approach allows the allowable range of motion to be established for an individual patient and to be customized for each patient. The instructions also include instructions for treating or imaging the target tissue of the patient with the probe and moving the robotic arm to affect movement of the probe within the allowable range of motion for the probe.

In some embodiments, the one or more computing devices may be configured to limit or constrain the movement of the treatment probe and/or imaging probe within an allowable range of motion based on one or more of training or motion adjusting steps.

In some embodiments, the training or motion adjusting steps may include providing a computer system used to control the robotic arms and attached probes with data regarding the possible range of motion of each probe. This data may be provided in the form of a mathematical representation of the respective possible range of motion for each probe or an image showing the possible range of motion along with indications of the amounts of translational and/or angular motion that are possible. The possible range of motion for one or more probes may then be limited or constrained to an allowable range of motion by a training or teaching mode or session.

In some embodiments, the training or motion adjusting steps may include providing a computer system used to control the robotic arms and attached probes with data obtained from a training or teaching mode or session. In such a mode or session, a physician may manipulate the probe or probes while inside a patient's body to "teach" the computer system what constraints or boundaries to place on the possible range of motion of each probe. This may be done to prevent harm to a patient, such as damage to tissue or an organ. A training or teaching mode may also (or instead) be conducted when the probes are outside of a patient's body. During a training mode, the computer system learns the limits to apply to the possible range of motions to prevent harm to the patient, and in response prevents the robotic arms from being able to position the probes in a harmful position or orientation. A training mode conducted outside the body is especially effective in training probe location and enabling anti-collision capability in the control system.

In some embodiments, the training or motion adjusting steps may include providing a computer system used to control the robotic arms and attached probes with images obtained from a monitoring or imaging probe (such as the TRUS probe described herein). In these embodiments, the monitoring or imaging probe can be used to provide images of the treatment probe and surrounding tissue and organs, and the computer system can be configured to control the position, orientation, or movement of the probes to prevent harm to the patient and/or a collision between the probes based on the images. In some embodiments, an image recognition method may be used to assist the computing system to identify a patient's tissue or organs. In some embodiments, a CT, MRI or other scan of the patient may be used to assist the image recognition system to identify the patient's tissue or organs and/or to determine appropriate limits or constraints on a possible range of motion of a probe.

In some embodiments, the disclosure is directed to a method of treating target tissue at a target site of a patient, where the method includes manually inserting a probe into the patient, coupling the probe to a robotic arm, establishing an allowable range of motion for the probe with the allowable range of motion stored on a memory of one or more computing devices operably coupled with the robotic arm. In these embodiments, establishing the allowable range of motion further comprises defining a possible range of motion for a distal end of the probe and modifying the possible range of motion of the distal end of the probe to define an allowable range of motion for the distal end of the probe for an individual patient. The method further includes treating or imaging the target tissue of the patient with the probe and moving the robotic arm under control of the one or more computing devices operably coupled with the probe, to affect movement of the probe within the allowable range of motion for the probe.

In some embodiments, the disclosure is directed to a system for treating target tissue at a target site of a patient, where the system includes a first robotic arm coupled to a treatment probe for treating the target tissue of the patient, a second robotic arm coupled to an imaging probe for imaging the target tissue of the patient and one or more computing devices operably coupled with the first robotic arm and the second robotic arm, the one or more computing devices configured to execute instructions for controlling movement of one or more of the first robotic arm or the second robotic arm, wherein the instructions constrain the movement of one or both probes to be within an allowable range of motion for the probe or probes.

The first robotic arm and/or the second robotic arm may be configured to adjust the position and/or orientation of the first arm and/or the second arm to maintain proper position or alignment of the treatment probe and the imaging probe, and/or to prevent collision or interference between the treatment probe and the imaging probe outside of the patient's body.

The first robotic arm and/or the second robotic arm may comprise one or more feedback sensing mechanisms. For example, the first robotic arm and/or the second robotic arm may be operably coupled with a force sensor configured to detect a compression of the tissue anterior to the treatment probe and/or imaging probe. The one or more computing devices may comprise instructions to control movement of the robotic arms in response to forces detected by the sensor, for example to prevent over-compression of the anterior tissue and resultant damage to the tissue and/or the probe. Another exemplary feedback sensing mechanism may comprise position and/or motion sensors operably coupled with the first and/or second robotic arm. The one or more computing devices may comprise instructions to control movement of the robotic arms in response to the position and/or motion detected by the sensors, for example to adjust the position of the treatment and/or imaging probe in response to patient movement during a treatment and/or scanning procedure.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 7 shows a method for operating a robotic arm coupled to an imaging probe in accordance with some embodiments;

FIG. 8A illustrates a configuration of a treatment probe and an imaging probe during treatment of a patient, in accordance with some embodiments;

DETAILED DESCRIPTION

Figure 1:
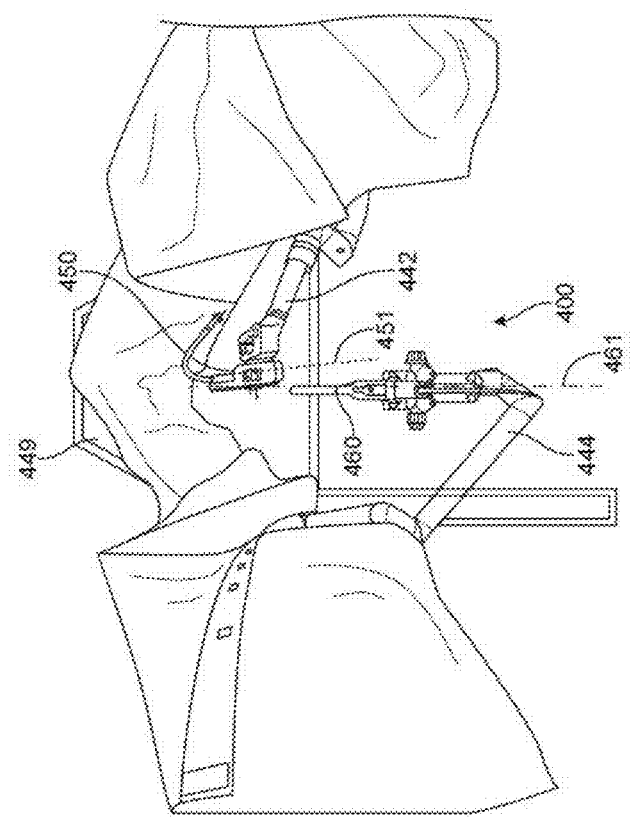
FIG. 1 shows a front view of a system for performing tissue resection in a patient, in accordance with some embodiments.

Embodiments of the present disclosure provide improved methods and apparatus for performing tissue treatment such as tissue resection, for example prostate tissue resection. The methods and apparatus disclosed herein are well suited for many types of surgical procedures and can be incorporated into many prior systems and methods. While some embodiments of the present disclosure are directed to transurethral treatment of the prostate, some aspects of the present disclosure may also be used to treat and modify other tissues and associated organs. These other tissues and associated organs may include but are not limited to the brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen or inserted through an opening created in body tissue.

The presently disclosed methods and apparatus are well suited for treating many types of tissue with an energy source. The tissue may comprise soft tissue, such as glandular tissue or capsular tissue, or hard tissue such as bone or blockages, such as kidney stones, for example. The energy source may comprise one or more of a laser beam, a water jet, an electrode, ultrasound, high intensity focused ultrasound, mechanical vibrations, radiofrequency (RF) energy an ultrasound transducer, microwave energy, cavitating energy such as a cavitating water jet or ultrasonic cavitations, radiation such as ionizing radiation from a radioisotope, or ion energy from ionization electrodes or plasma energy from plasma electrodes. The presently disclosed methods and apparatus are well suited for performing lithotripsy to break up kidney stones, for example. The presently disclosed methods and apparatus are well suited for treatment with radiation, such as a radio isotope on the treatment probe. The radiation treatment can be provided on the probe and removed with the probe, or implanted from the treatment probe, for the treatment of cancer for example.

In some embodiments, an image-guided treatment system comprises a treatment probe and an imaging probe. The imaging probe may be configured to provide an image of the target site while the treatment probe performs resection or other treatment of the target tissue. The treatment probe and the imaging probe may each be coupled to robotic arms under control of one or more computing devices, in order to enable more precisely controlled movement of one or both of the arms and to improve the safety and efficiency of treatment using the treatment system. The treatment probe and the imaging probe may instead or also be under the control of signals received from a joystick, GUI or other form of manual controller.

The robotic arms can be configured in many ways. Work in relation to the present disclosure suggests that a TRUS probe can exert force on a robotic arm. In some embodiments this force is related to force from the patient against the probe. In some embodiments this force is related to force caused by the practitioner surgeon moving the probe against tissue and moving the tissue for the purpose of improving imaging or tissue position relative to the intended treatment. The length of the probe can result in a corresponding torque on the robotic arm. Collisions between probes or between a probe and a patient's organs or tissue can cause forces on the robotic arms that can impact their positioning precision and control.

The present inventors have conducted experiments to determine the amount of force from the TRUS probe that can be applied to the robotic arm. This force can be measured at a motor mount exterior to the patient, for example. The force can range from 0 to about 49 Newtons, depending on the surgical placement of the probe and patient. In some embodiments, the distance from the arm to the point of contact with prostate corresponds to an amount of torque on the arm.

Instrument positioning can have three categories of motion control and capability in accordance with some embodiments disclosed herein. The three categories of motion generally comprise a 1) coarse motion capability for movement, storage and preparation for surgery, 2) an intermediate movement capability for aligning the probe with the patient and inserting the probe into the patient, and 3) a fine movement capability corresponding to positional tolerances for accurate surgery.

Coarse motion capability allows for storage below and adjacent to the table and during patient positioning, for example.

Intermediate motion allows for instrument positioning with respect to the patient on the surgical support structure, e.g. an operating room ("OR") table, for example when the system is being prepared and positioned for patient entry. A typical range of position for the TRUS probe or any suitable surgically invasive probe is to have free motion for insertion into the patient, which can be describe with a X,Y,Z coordinate system. With an appropriate coordinate reference system, the entry to a lumen of the patient may correspond to values of 0, 0, 0 in an X,Y,Z coordinate system. The coordinate reference may also comprise angular coordinate references of X',Y',Z'. The entry to the lumen may comprise an anus of the patient. With an anal entrance at 0,0,0 and the probe colinear with the patient axis, the intermedia motion may comprise an X motion tolerance of +/−2 to 15 cm, Y motion tolerance of +/−2 to 15 cm, and Z motion tolerance of +/−2 to 30 cm. In some embodiments, the X and Y motion corresponds to translation of the probe along the X and Y coordinate references. The Z axis position corresponds to movement along an axis of the lumen and may correspond to advancement and retraction of the probe along the body lumen, e.g. translational movement into and out of the patient. With an angular adjustment of X',Y', Z', the angular position capability may comprise X'+/−zero to 30 degrees, Y'+/−zero to 30 degrees, Z'+/−zero to 30 degrees, with respect to the natural axis of the patient. Work in relation to the present disclosure suggests that a probe with these angular capabilities can be manipulated by a user for insertion into the patient.

In some embodiments, the fine movement capability and tolerances correspond to a configuration of the robotic probe and arms with the probe positioned in the patient, for example during tissue resection and imaging. When the system is in use with instruments positioned for diagnosis and treatment, the sensors and controls and described herein can be configured to prevent tissue damage, and also to position a treatment probe and an imaging probe to obtain reliable images, e.g. optimal images, and the treatment and imaging probes can be precisely positioned and firmly held in position against tissue pressures. The X,Y,Z reference frame can be centered on the lumen entrance at 0,0,0 and (the probe colinear with the patient axis). In some embodiments, X motion tolerance is +/−0 to 5 cm; the Y motion tolerance is +/−0 to 5 cm; and Z motion tolerance is +/−0 to 15 cm. The X and Y motion generally corresponds to translation of the probe, and the Z axis corresponds to advancement and retraction of the probe in and out of the patient. The corresponding angular adjustment ranges for X',Y',Z' are X'+/−zero to 10 degrees, Y'+/−zero to 10 degrees, and Z'+/−zero to 15 degrees, with respect to a natural axis of the patient, for example with reference to a midline of the patient with the Z axis extending along the midline of the patient. While the above values represent example ranges of motion, the robotics arms and surgical probes may provide tighter tolerances for fixed position configurations of the probe. For example, when the probe is intended to be held in a fixed position, the rotational tolerances can maintain one or more of X',Y',Z' within a within +/−5° tolerance or less, e.g. +/−3°. With respect to translational movement, the manually set position can be maintained to a positional tolerance of 5 mm or less, 3 mm or less, or 2 mm or less for one or more of the X, Y, Z axes, for example. In some embodiments, these tolerances are maintained for each of X, Y, Z and X', Y', Z'. In some embodiments, the probe is manually set, and the translational and rotational tolerances are maintained to within the above values, which can improve the accuracy of the tissue treatment and associated imaging. These tolerances may correspond a maximal structural relaxing or loading of the arm with the probe mounted thereon, for example.

The probe can be manipulated and inserted into the patient in many ways. For example, the probe can be manipulated manually, and the robotic arm moved into alignment with the probe and coupled to the probe, with the probe maintaining the above tolerances when released by the user and the arm subsequently supporting the full load of the patient and probes. The arm can be brought into alignment with the probe manually, or with at least some automation in which sensors and guidance circuitry are used to bring the arm into alignment with the probe held by the user. The arm may comprise a coupling structure to engage the probe with 6 degrees of freedom, such that a coupling structure on the arm can be brought into precise alignment with the coupling structure on the probe. The coupling structures can be subsequently engaged and coupled to each other in response to detection of the alignment. In some embodiments, sensors are provided on one or more of the arm or the probe to detect alignment between the arm and probe, and the coupling structures engaged in response to the detected alignment. The robotic arm may comprise a linkage coupled to a processor or computing device, in which the processor or device controls movement of the arm and brings the arm into alignment with the probe held by the user.

In some embodiments, the urethral probe has similar dimensional, motion and tolerance capabilities to the TRUS probe.

In some embodiments, the probe comprises a mass within a range from about 250 grams to 1500 grams, and the arm maintains the tolerances described herein with the probe comprising the mass within this range.

The robotics arms as described herein can improve alignment between the treatment probe and the imaging probe, which may comprise a sagittal plane of an imaging TRUS probe. For example, the treatment probe be aligned substantially coplanar along the sagittal plane of the imaging probe. This coplanarity can provide clear imaging and alignment of coordinates of the treatment probe and imaging probe. In some embodiments, the tolerance of this coplanarity is related to the combination of the width of the treatment probe and the width of the imaging plane capability, e.g. width of the image captured with ultrasound beam forming. The relative position of the TRUS to the treatment probe can be substantially parallel and aligned within an angular tolerance. The alignment can be within a range from +/−zero (parallel) to about 30 degrees. In some embodiments, the elongate axis of the treatment probe and TRUS probe are aligned in a substantially co-planar configuration, with the separation distance between the probes varying along the length of the imaging and treatment probes. For example, the distal tip of the treatment probe can be farther away from the TRUS probe and the proximal end closer to the TRUS probe, in which the two probes are inclined relative to each other, although substantially coplanar. The inclination between the two probes can be related to the tissue or organ constraints of natural orifices of each unique human or patient anatomy. The distances between the entrances to the naturally available orifices can vary, for example within a range from about 5 cm to about 25 cm separation.

In some embodiments, the imaging probe and the treatment probe are aligned so that the treatment probe is within the field of view of the imaging probe. In some embodiments, the alignment is configured to maintain the treatment probe within a field of view of the imaging probe. In some embodiments, the treatment probe is configured to move to a position and the imaging probe is configured to maintain the treatment probe within the field of view. In some embodiments, this provides for monitoring of the position and orientation of the treatment probe during treatment and can reduce the possibility of harm to a patient.

In some embodiments, the monitoring of the position and orientation of the treatment probe by the imaging probe can generate a signal to a computing device to stop movement of one or both probes or to alter the position, location or orientation of one or both probes to prevent a collision between the probes while inside a patient's body and/or to prevent harm to a patient's tissue or organs. In some embodiments, monitoring of the position and orientation of the treatment probe by the imaging probe can cause the system to stop motion of one or both probes and generate an alert to the physician to prevent harm to the patient. In addition, it is important to prevent collisions between the robotic arms or between a robotic arm and a surgical tool or accessory, as this could cause injury to a patient or impact the execution of a treatment plan. These types of collisions can be limited or prevented by a calibration procedure based on using the forward kinematics data regarding the arms.

In some embodiments, one or more of computer vision, image recognition, or a trained machine learning model may be used to assist the system to recognize when one or both probes are too close to each other or to tissue or an organ of a patient.

In these and other embodiments, stopping motion of one or both probes or changing the position, location, or orientation of one or both probes may be implemented by controlling one or both robotic arms.

FIG. 1 shows an exemplary embodiment of a system 400 for performing tissue resection in a patient. The system 400 may comprise a treatment probe 450 and an imaging probe 460. The treatment probe 450 may be coupled to a first arm 442, and the imaging probe 460 coupled to a second arm 444. One or both of the first arm 442 and the second arm 444 may comprise robotic arms whose movements may be controlled by one or more computing devices operably coupled with the arms. The treatment probe 450 may comprise a device for removing target tissue from a target site within a patient. The treatment probe 450 may be configured to deliver energy from the treatment probe 450 to the target tissue sufficient for removing or otherwise treating the target tissue. For example, the treatment probe 450 may comprise an electrosurgical ablation device, a laser ablation device, a transurethral needle ablation device, a water jet ablation device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
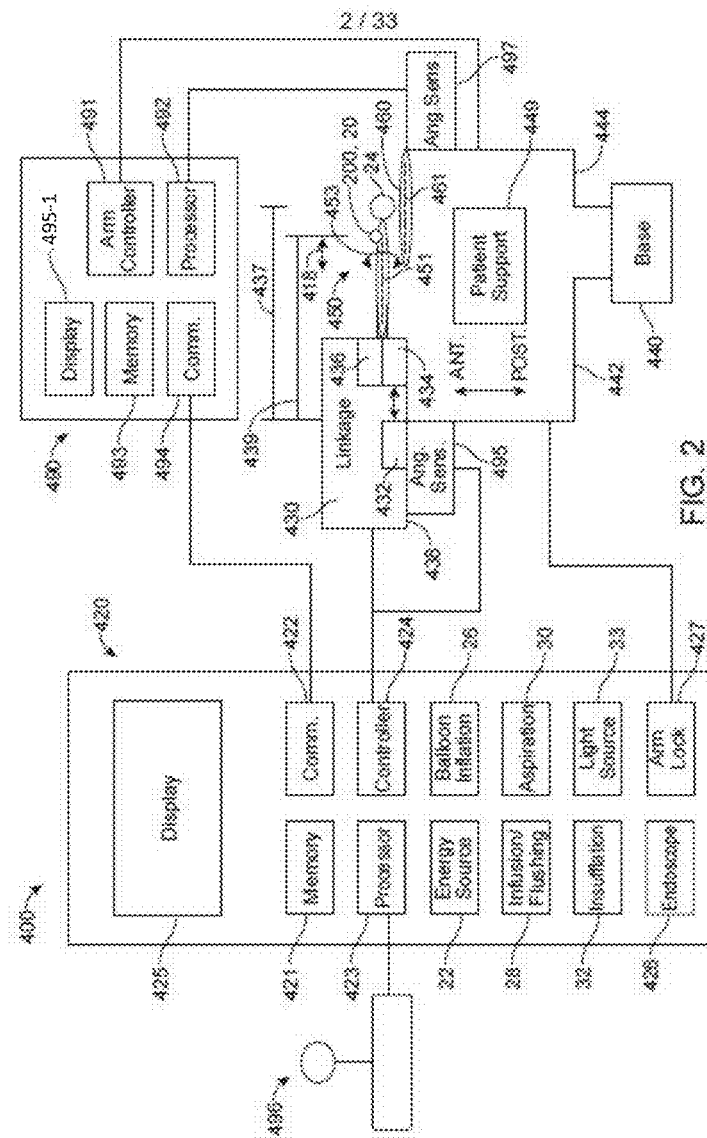
FIG. 2 schematically illustrates a system for performing tissue resection in a patient, in accordance with some embodiments.

FIG. 2 schematically illustrates an exemplary embodiment of the system 400 for performing tissue resection in a patient. The system 400 comprises a treatment probe 450 and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end (typically referred to as the distal end) of the treatment probe or the imaging probe in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The computing device or processor can be configured with instructions for the probe control to be switched between automated image-based guidance treatment with the energy source and treatment with the energy source in response to user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such that the treatment or imaging probe can be desirably rotated and/or translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image data of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment probe 450 based on images from imaging probe 460. The coupling can be achieved with the common base 440 as shown. Alternatively, or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively, or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively, or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 422. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. The probe 450 may comprise a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed to the substantially constant distance 437 from the anchor 24. The substantially constant distance 437 between the anchor 24 and the fixed first portion 432 of the linkage allows the treatment to be accurately placed. The first portion 432 may comprise a linear actuator to accurately position the high-pressure nozzle 200 in the energy delivery region 20 at a desired axial position along an elongate axis 451 of treatment probe 450.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust in manner 418 in response to computer control to set a target location along the elongate axis 451 of the treatment probe referenced to anchor 24. The first portion of the linkage remains fixed, while the second portion 434 adjusts the position of the energy delivery region 20 along the axis 451. The third portion of the linkage 436 adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 495-1.

In order to facilitate precise control of the treatment probe and/or the imaging probe during treatment of the patient, each of the treatment probe and the imaging probe may be coupled to a robotic, computer-controllable arm. For example, referring to system 400 shown in FIG. 2, one or both of the first arm 442 coupled to the treatment probe 450 and the second arm 444 coupled to the imaging probe 460 may comprise robotic, computer-controllable arms. The robotic arms may be operably coupled with one or more computing devices or processors configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

Either robotic arm described above may comprise 6 or 7 or more joints to allow the arm to move under computer control. Suitable robotic arms are commercially available from several manufacturers such as RoboDK Inc., Kinova Inc. and several other manufacturers.

The one or more computing devices or processors operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters or treatment plans. The robotic arms may be configured to automatically move the treatment probe and/or imaging probe along a pre-planned or programmed treatment or scanning profile, which may be stored in or on a memory element able to be accessed by the one or more computing devices or processors. Alternatively, or additionally to automatic adjustment of the robotic arms, the one or more computing devices may be configured to control movement of the treatment probe and/or the imaging probe in response to user inputs, for example through a graphical user interface or movable controller of the treatment apparatus.

Alternatively, or additionally to automatic adjustment of the robotic arms, the one or more computing devices may be configured to control movement of the treatment probe and/or the imaging probe in response to real-time imaging or positioning information. In some embodiments, this may be in response to patient anatomy recognized in one or more images captured by the imaging probe or other imaging source (from which allowable and safe ranges of motion of the treatment probe and/or the imaging probe may be determined) and/or position information of the treatment probe and/or imaging probe from one or more sensors coupled to the probes and/or the robotic arms.

As will be described further herein, changes to the control of or constraints on the movement of the robotic arms and/or probes may result from one or more of a combination of factors. These factors include (a) the possible range of motion of the robotic arms and probes as defined or expressed in the form of an image, a maximum angular or linear separation between elements or sections of a probe or arm, a mathematical function or other mathematical representation of a geometric section (e.g., a cylinder, a conic section, a sphere or section of a sphere, a combination of different shaped sections, etc.) representing the range of possible motion of a probe, (b) constraints or limits on the motion of a probe "taught" to the system by a physician who may demonstrate an allowable range of motion of the probes before or after the probes are inserted into a patient's body, and (c) images captured during a treatment procedure that are analyzed to determine when movement of a probe or probes should be prevented or altered to prevent collision between the probes or harm to a patient's tissue or organs. In some embodiments, the images may be subjected to further processing in order to determine the position or orientation of one or both probes relative to each other or to the tissue or an organ of a patient. In some embodiments, the further processing may include one or more of image recognition, application of a trained machine learning model, comparison to a database of images of the patient's organs or the organs of others, or inputs provided by a physician.

Figure 3B:
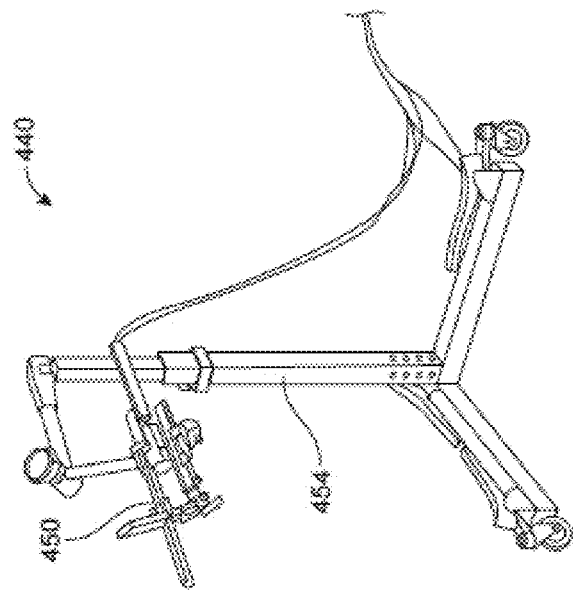
FIGS. 3A and 3B show perspective views of a common base or mount for supporting one or more robotic arms, in accordance with some embodiments.
Figure 3A:
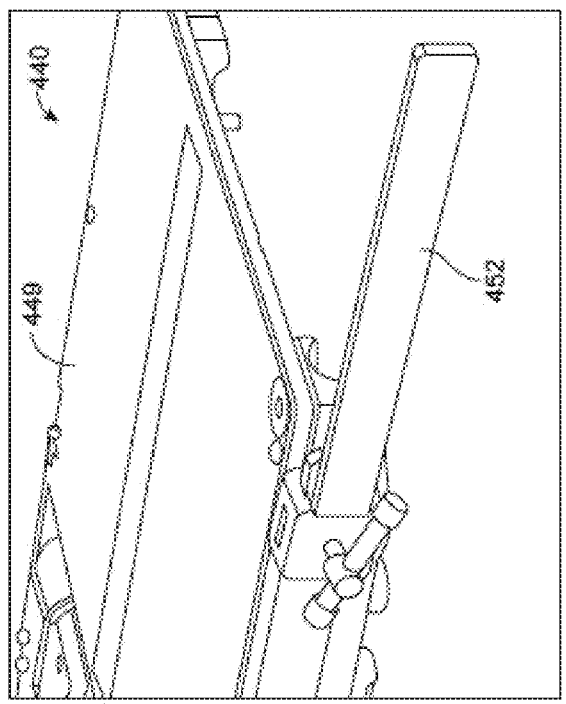

FIGS. 3A and 3B show exemplary embodiments of a common base or mount 440 for supporting one or more robotic arms of an image-guided treatment system as disclosed herein. FIG. 3A shows a patient support 449 comprising one or more rails 452. The patient support 449 may comprise a surgical table or a platform. One or more robotic arms associated with one or more of the treatment probe or the imaging probe may be mounted to the rails 452, such that the rails function as the common base 440. FIG. 3B shows a common base 440 comprising a floor stand 454 configured to couple to the first robotic arm connected to the treatment probe and/or the second robotic arm connected to the imaging probe. The floor-stand 454 may be positioned between the patient's legs during the treatment procedure.

Figure 4A:
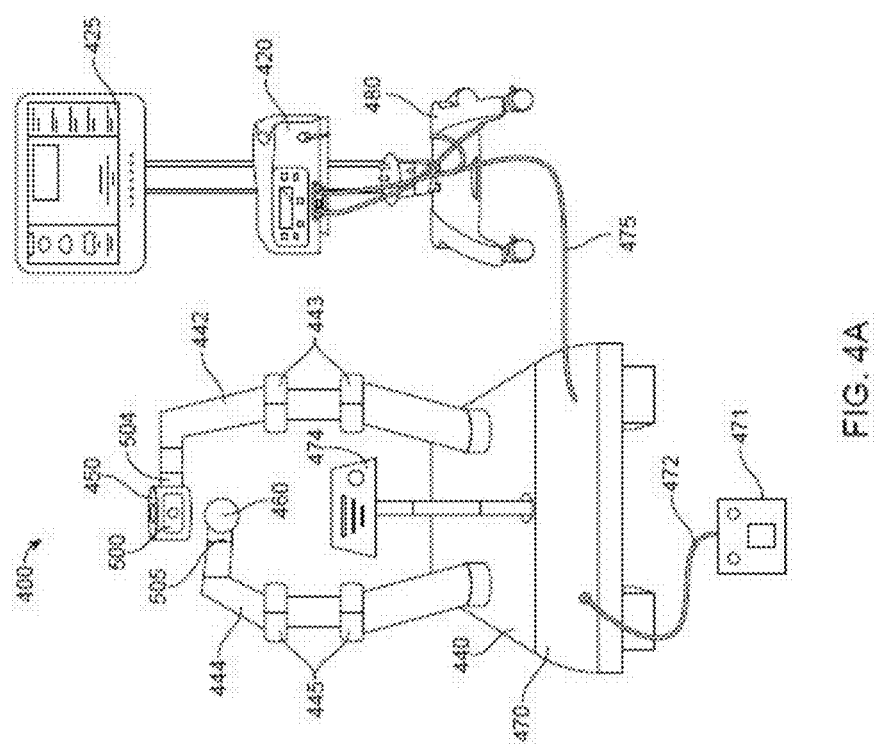
FIGS. 4A and 4B illustrate a perspective and side view, respectively, of a system for performing tissue resection in a patient that comprises a mobile base, in accordance with some embodiments.
Figure 4B:
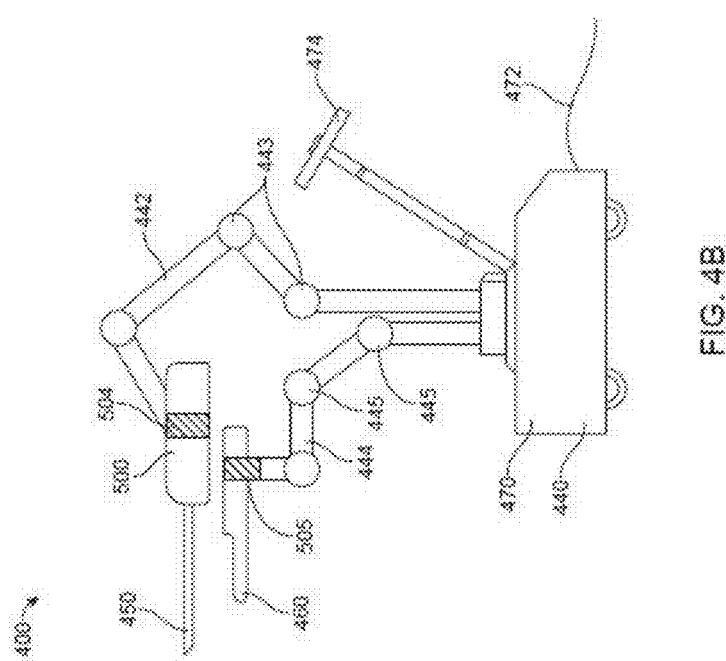

FIGS. 4A and 4B illustrate an exemplary embodiment of a treatment system 400 as described herein comprising a mobile base 470. FIG. 4A is a front view and FIG. 4B is a side view of the treatment system 400. The treatment system 400 comprises a treatment probe 450 coupled to a first robotic arm 442, and an imaging probe 460 coupled to a second robotic arm 444. The first robotic arm 442 and the second robotic arm 444 each comprises a proximal end and a distal end, the distal end coupled to the treatment probe 450 and the imaging probe 460, respectively, and the proximal end coupled to a common base 440 comprising a mobile base 470. The first robotic arm 442 may comprise a first arm coupling structure 504 to couple to the treatment probe 450, and the second robotic arm 444 may comprise a second arm coupling structure 505 to couple to the imaging probe 460. The treatment probe 450 may be coupled to the distal end of the first robotic arm 442 via an attachment device 500, which may comprise a linkage configured to affect movement of the treatment probe as described herein (e.g., rotation, translation, pitch, etc.). Coupling of the treatment probe 450 to the first robotic arm 442 may be fixed, releasable, or user adjustable. Similarly, coupling of the imaging probe 460 to the second robotic arm 444 may be fixed, releasable, or user adjustable.

The first robotic arm 442 may articulate at one or more first arm joints 443. The imaging arm 444 may articulate at one or more second arm joints 445. Each arm joint 443 or 445 may be operably coupled with a computer-controllable actuator, such as a stepper motor, to affect movement at the joint. Each arm joint 443 or 445 may comprise one of a variety of kinematic joints including but not limited to a prismatic, revolute, parallel cylindrical, cylindrical, spherical, planar, edge slider, cylindrical slider, point slider, spherical slider, or crossed cylindrical joint, or any combination thereof. Moreover, each arm joint 443 or 445 may comprise a linear, orthogonal, rotational, twisting, or revolving joint, or any combination thereof.

The system 400 may further comprise a console 420 as described herein, which may be supported by a mobile support 480 separate from the mobile base 470. The console 420 may be operably coupled with the mobile base 470 via a power and communication cable 475, to allow control of the treatment probe 450 coupled to the mobile base via the first robotic arm. The treatment console 420 comprises a computing device, typically including a processor and a memory having stored thereon or therein computer-executable instructions for execution by the processor. When executed, the instructions may cause the console to control various modules or functionalities of the treatment console, such as an energy source, infusion/flushing control, aspiration control, and other components as described herein with reference to FIG. 2.

The treatment console 420 may further comprise a display 425 in communication with the processor. The display 425 may be configured to display, for example, one or more of: subject vital signs such as heart rate, respiratory rate, temperature, blood pressure, oxygen saturation, or any physiological parameter or any combination thereof; status of a procedure; one or more previously taken images or sequence of images of a treatment site from one or more views; one or more real-time images or sequence of images of the treatment site from one or more views acquired by the imaging probe 460; a set of treatment parameters including but not limited to a treatment mode such as cutting or coagulating, an intensity of treatment, time elapsed during treatment, time remaining during treatment, a depth of treatment, an area or volume of the treatment site that has been treated, an area of the treatment site that will be treated, an area or volume of the treatment site that will not be treated, location information of the treatment probe 450 or the imaging probe 460 or both; treatment adjustment controls such as means to adjust the depth of treatment, the intensity of treatment, the location and/or orientation of the treatment probe 450, the depth of imaging, or the location and/or orientation of the imaging probe 460, or any combination thereof; or system configuration parameters.

The mobile base 470 may further comprise one or more computing devices to control operation of the one or more robotic arms. For example, the mobile base may comprise processors and a memory having stored thereon or therein computer executable instructions for execution by the one or more processors. The memory may have stored thereon or therein instructions for operating the one or more robotic arms coupled to the mobile base. The processor may be operably coupled with the robotic arms via suitable electromechanical components to affect movement of the robotic arms. For example, each of the one or more joints of a robotic arm may comprise a step motor, and the processor may be operably coupled with the step motor at each joint to actuate the motor by a specified increment in a specified direction. Alternatively, the one or more robotic arms may be operably coupled with one or more processors of the console 420 or a separate imaging console (such as imaging console 490 shown in FIG. 2), wherein the one or more console processors may be configured to execute instructions for controlling movement of the one or more robotic arms, and may communicate the instructions to the robotic arms via communication circuitry (such as communication circuitry 422 of console 420 or communication circuitry 494 of console 490 shown in FIG. 2). The computer executable instructions for controlling movement of the robotic arms may be pre-programmed and stored on a memory or may be provided by a user via one or more user inputs before or during treatment of the patient using the treatment system.

The one or more computing devices operably coupled with the first and/or second robotic arms may be configured to control movement of the arms so as to adjust the pitch, yaw, roll, and/or linear position of the treatment probe and/or imaging probe along the target site.

The mobile base 470 may comprise one or more user input devices to enable a user to control movement of the robotic arms under computer instructions. For example, as shown in FIGS. 4A and 4B, the mobile base may comprise a keyboard 474 and/or a footswitch 471, the footswitch operably coupled with the mobile base via a footswitch cable 472. The keyboard 474 and the footswitch 471, independently or in combination, may be configured to control operation of the first robotic arm 442 and/or the second robotic arm 444, for example via articulation of one or both robotic arms at one or more joints. The keyboard and the footswitch may be in communication with the one or more processors configured to control movement of the robotic arms. When a user inputs instructions into the keyboard and/or the footswitch, the user instructions can be received by the one or more processors, converted into electrical signals, and the electrical signals may be transmitted to the one or more computer-controllable actuators operably coupled with the one or more robotic arms. The keyboard and/or the footswitch may control movement of one or both arms towards or away from a treatment position, a position of interest, a predetermined location, or a user-specified location, or any combination thereof.

Optionally, the keyboard 474 and the footswitch 471, independently or in combination, may be configured to control operation of the treatment probe 450 and/or imaging probe 460. For example, the keyboard 474 and/or footswitch 471 may be configured to start, stop, pause, or resume treatment with the treatment probe. The keyboard 474 and/or footswitch 471 may be configured to begin imaging or freeze, save, or display on the display 425 an image or sequence of images previously or currently acquired by the imaging probe.

The mobile base 470 and the mobile support 480 of the console 420 may be independently positionable around a patient, supported by a patient support 449 such as a platform. For example, the mobile base 470, supporting the first and second robotic arms and the treatment and imaging probes, may be positioned between the patient's legs, while the mobile support 480 carrying the console 420 and the display 425 may be positioned to the side of the patient, such as near the torso of the patient. The mobile base 470 or the mobile support 480 may comprise one or more movable elements that enable the base or the support to move, such as a plurality of wheels. The mobile base 470 may be covered with sterile draping throughout the treatment procedure, in order to prevent contamination and fluid ingress.

Figure 5A:
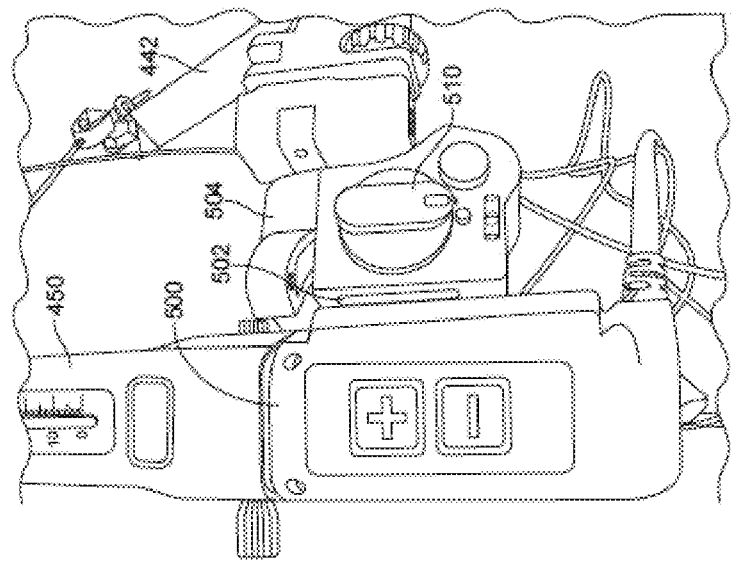
FIGS. 5A and 5B show top views of a coupling between a treatment probe and a first robotic arm, in accordance with some embodiments, with FIG. 5A showing the treatment probe and the first robotic arm uncoupled and FIG. 5B showing the treatment probe and the first robotic arm coupled.
Figure 5B:
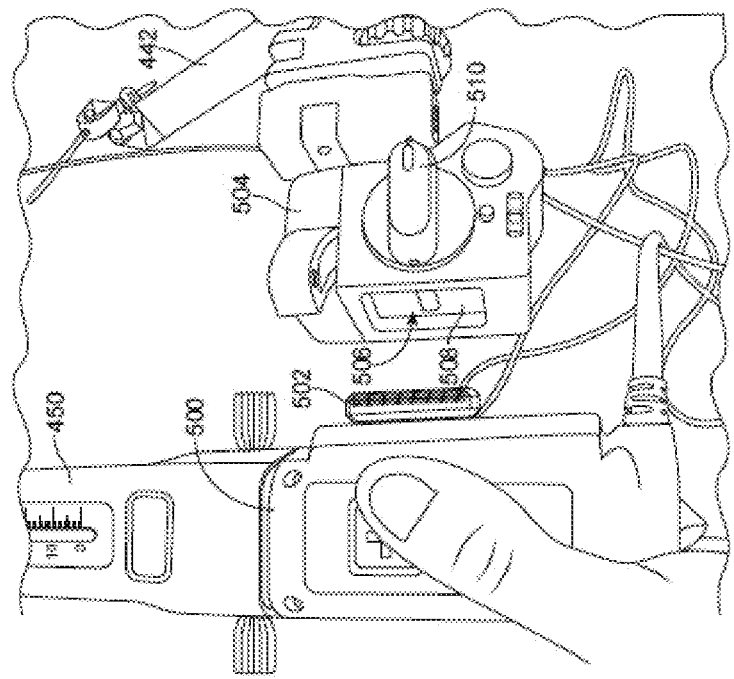

FIGS. 5A-5B show an exemplary coupling between a treatment probe 450 and a first robotic arm 442. FIG. 5A shows the treatment probe uncoupled from the robotic arm. FIG. 5B shows the treatment probe coupled to the robotic arm. As shown, the treatment probe 450 may be coupled to the robotic arm 442 with an attachment device 500 which may comprise a reusable motor pack. The treatment probe 450 may be removably coupled to the attachment device 500. The attachment device may further comprise a connector 502 configured to couple to the robotic arm and lock the attachment device in place. The robotic arm 442 may comprise a coupling structure 504 disposed at the distal end of the arm, configured to lockingly receive the connector 502 of the attachment device 500. Once the treatment probe and the robotic arm are coupled together, movement of the treatment probe may be controlled by moving the robotic arm (e.g., by articulating one or more joints of the robotic arm under computer control).

In some embodiments, the treatment probe is coupled to the robotic arm via a quick release mechanism, such that the coupling between the probe and the robotic arm is capable of a quick disconnect in order to prevent injury to the patient in case the robotic arm loses position or otherwise fails to operate correctly. The treatment probe and the robotic arm may be coupled to one another in many ways such as mechanically (e.g., a broom clip) and/or magnetically. For example, in the embodiment shown in FIGS. 5A and 5B, the coupling structure 504 may comprise a slot 506 having a magnet 508 disposed therein, and the connector 502 may comprise a ferromagnetic fixture configured to fit within the slot 506 to engage the magnet 508. The coupling structure 504 may further comprise a latching mechanism 510 to selectively engage or disengage the connector 502 with the magnet 508. For example, as shown in FIGS. 5A and 5B, the latching mechanism 510 may comprise a rotatable knob that can be rotated to affect engagement of the magnet 508 of the coupling structure 504 with the connector 502 of the attachment device 500. The latching mechanism may be automatically or manually engaged or disengaged by a user to couple or de-couple, respectively, the attachment device 500, and hence the treatment probe 450 coupled thereto, to the robotic arm 442. In some embodiments, the coupling structure 504 may be operably coupled with the one or more computing devices configured to control the robotic arm, and the one or more computing devices may comprise instructions to release the coupling of the coupling structure to the probe when an error is detected in the operation of the robotic arm.

In some embodiments, the first robotic arm 442 may be configured to automatically locate the treatment probe 450 in response to sensor location data from one or more of the attachment device 500 or coupling structure 504. The first robotic arm 442 may be operated in a "seek" mode, for example, to locate the attachment device 500. In some embodiments, the probe comprises one or more fiducial targets and the robotic arm comprises corresponding sensors of sufficient resolution and positioning to identify the relative position of the probe in 3D space. In some embodiments, the processor is configured with instructions to seek the treatment probe or imaging probe with the mounting structures on the robotic arm while the user holds the probe steady, for example when the probe has been positioned in the patient.

Figure 8B:
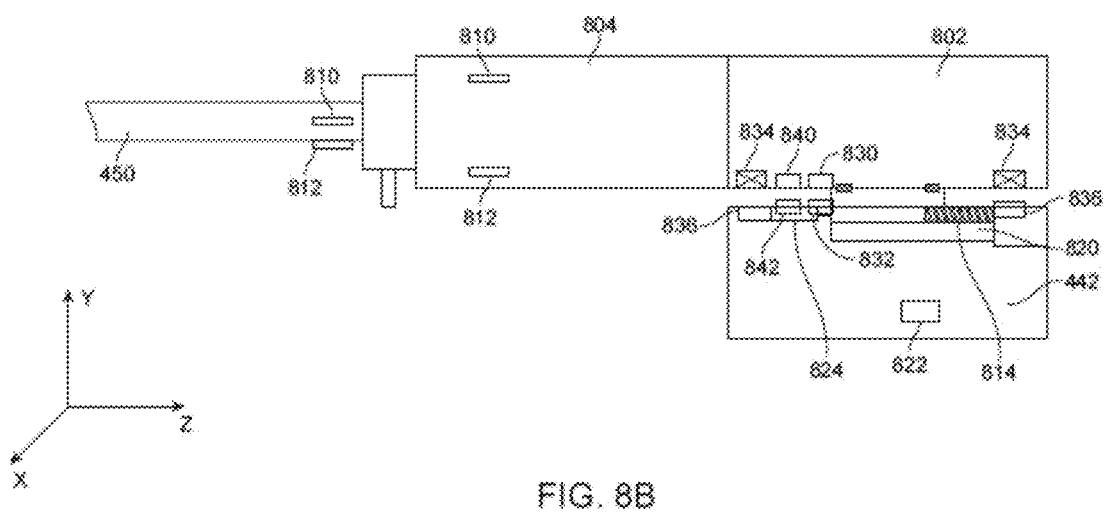
FIG. 8B is a schematic illustration of a probe and a robotic arm with force detection sensors, in accordance with some embodiments.

The sensors on the robotic arm such as the first robotic arm 442 and sensors on the probe such as the treatment probe can be arranged in many ways, for example as shown in FIG. 8B.

The processor can be coupled to the sensors near the end of the robotic arm or on the probe to dynamically update the relative location during the movement of the robot arm while seeking to engage the probe on the arm. The sensors on the robotic arm may comprise a plurality of sensors comprising one or more of capacitive, capacitive displacement, doppler, inductive, magnetic, optical, radar, sonar, ultrasonic or Hall effect sensors, in order to determine relative distances between the robotic arm and the probe. In some embodiments the probe comprises a plurality of targets and the sensors are configured to generate signals in response to distances from the plurality of targets. Alternatively, or in combination, the sensors can be located on the probe and the targets on the robotic arm. In some embodiments, the sensors comprise close contact mechanical sensors to confirm docking of the probe on the robotic arm or in proximity to the arm, for example to sense the position of the probe in relation to the robotic arm when the probe and arm are within a few millimeters of docking with each other. The close contact mechanical sensors may comprise one or more of micro-motion switches, whisker touch sensors, or a pin-in-hole contact switch. In some embodiments, the probe and robotic arm comprise an integrated locking mechanism to provide a non-movement locking engagement at the final position of contact. The integrated locking mechanism may comprise one or more of magnetics, electromagnetics, a latching, screw such as a multi turn latching screw or quarter turn locking screw, a vacuum, or other mechanical means of reversible attachment as will be understood by one of ordinary skill in the art.

In some embodiments, a plurality of sensors is used, such as one or more sensors for near, one or more sensors for intermediate and one or more sensors for far separation distances between the probe and the robotic arm. A coarse location sensor can be used to determine the approximate location of the probe, e.g. a beacon. One or more sensors can be used for fine location positioning of the probe in relation to the robotic arm, e.g. proximity sensors. In some embodiments, one or more markers on the probe are used with a camera and machine vision detection of the one or more markers.

In some embodiments, coarse location sensors may be provided which may be an infrared (IR) beacon which enables the coarse positional spatial location for homing detection of the robotic arm to the probe. In some cases, a homing beacon, such as an IR beacon, allows for homing across larger distances as compared to a sensor that may rely on visual recognition of fiducials.

In some embodiments, a docking detection sensor confirms that the robotic arm has engaged or is in close proximity with a probe. As an example, a Hall effect sensor can be used in conjunction with a permanent magnet to affect the sensors output. In some embodiments, a Hall effect sensor is noise immune, non-contact, and has a consistent detection range. Any of a number of different types of Hall sensors may be utilized, and in many cases, the sensor functions as a simple switch and linear range measurement and detection in which the overall output voltage is set by the supply voltage and varies in proportion to the strength of the magnetic field. This results in a distance measurement between the sensor and a locating magnet and may be used to measure the distance between the robotic arm and the probe and aid in docking. The sensor and beacon may be located within respective housings of the robotic arm and probe.

In some embodiments, positional sensing of the robotic arm is performed by an inertial measurement unit (IMU), which may include up to 9-axis detection. In some cases, a 6-axis IMU can be used for motion detection, vibration detection, positional orientation information, redundancy and backup of the primary encoder signals that may be located in the joints of the robotic arms. The IMUs may perform a dual function of seeking a probe for docking with the robotic arm as well as force detection and motion compensation as described herein. The described sensors can be used in combination with any robotic arms or probes described herein.

According to some embodiments, the procedure for docking a robotic arm with a probe may comprise an IR beacon to provide coarse positional and spatial location for homing detection, fiducials on either the arm or the probe and an optical sensor to view the fiducials which can be used to allow fine alignment of positional location in the XY plane, and a Hall effect sensor to detect Z direction proximity for docking. An IR beacon allows for larger distance seek for the home position of the robotic arm relative to the probe. The fiducials and optical sensor may allow for rapid, low-latency detection of the 3D location and 3D orientation of the probe by the robotic arm. A user interface, which may be located on the robotic arm, on the probe, or on a robotic arm control unit, may indicate distance, position, docked status or other information. In some embodiments, the user interface includes one or more visual cues, such as LED indicators, to indicate the relative position and/or docking status of the arm and probe.

While the coupling mechanism shown in FIGS. 5A and 5B is described in the context of coupling the treatment probe to the first robotic arm, a substantially similar mechanism may also be used for coupling the imaging probe to the second robotic arm 444. For example, the coupling structure of the second robotic arm 444 may comprise a similar coupling mechanism for engaging an attachment device connected to the imaging probe.

Figure 6:
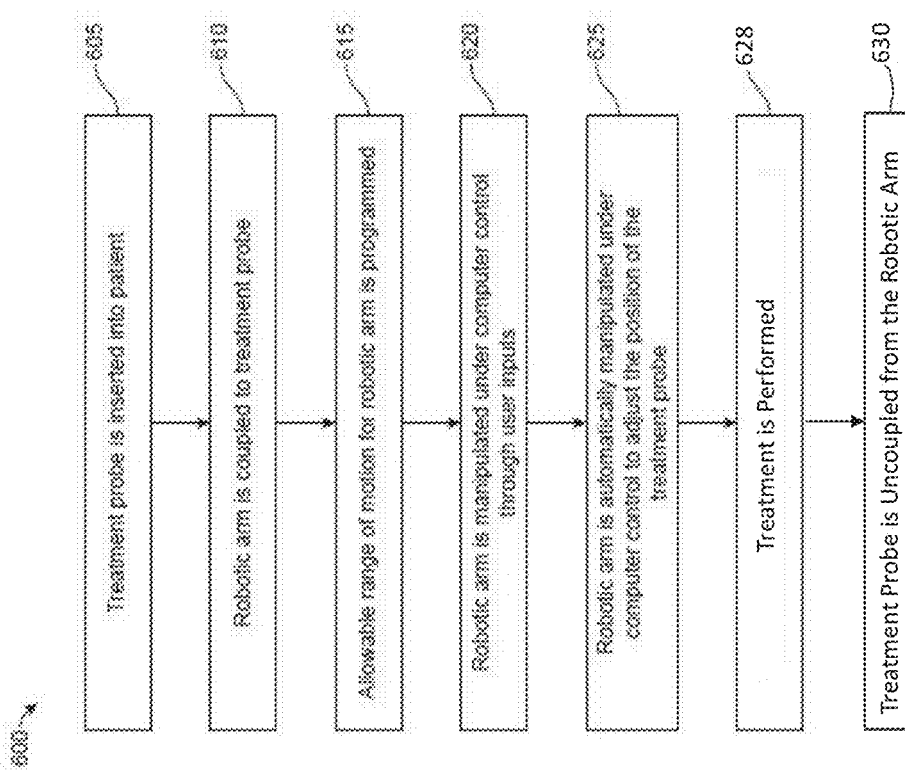
FIG. 6 shows a flow chart for a method of operating a robotic arm coupled to a treatment probe, in accordance with some embodiments.

FIG. 6 shows a method 600 for operating a robotic arm coupled to a treatment probe in accordance with some embodiments.

With a step 605, a treatment probe is inserted into the patient, with the robotic arm on standby to one side of the patient, manually, semi-automatically, or automatically. For example, for a prostatic tissue resection system, the treatment probe may be manually inserted into the urethra of the patient towards the prostate. The treatment probe may be manipulated as it is advanced to track the tortuous path of the urethra, prostate, and bladder neck. After entering the urethra, the treatment probe may be turned (e.g., by 90 degrees) before further advancement through the urethral bulb. Instructions may be provided to the user to perform such a turn, or in cases where insertion is automatic or semi-automatic, the robotic arm may be instructed to make such a turn in response to image, position, and/or force feedback data. In some embodiments, the treatment probe is inserted into the patient concurrently with or after the imaging probe, and in some instances, the treatment probe insertion may be guided by image data from the inserted image probe. The insertion point or location of a patient may vary, and may include organs, the prostrate, kidney, heart, lung, liver, etc. As mentioned, while some embodiments of the present disclosure are directed to transurethral treatment of the prostate, aspects may also be used to treat and modify other tissues and associated organs. These other tissues and associated organs include but are not limited to the brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat.

With a step 610, the robotic arm is coupled to the treatment probe. A user can manually align the robotic arm coupling structure to the attachment device of the treatment probe as described herein, while the robotic arm remains in a passive or "zero-gravity" mode. The attachment device and the coupling structure of the robotic arm can couple together to attach the robotic arm to the treatment probe. In some embodiments, a robot or robotic arm may be configured to "find" the inserted probe while operating in an autonomous or semi-autonomous mode.

With a step 615, the allowable range of motion for the robotic arm is programmed. For example, a user can manually move, rotate, and angulate the treatment probe to set the boundaries for the allowable range of motion of the treatment probe, while the probe is connected to the robotic arm with the robotic arm still in passive mode. The user may set the boundaries based on a combination of cystoscopic, ultrasound, and haptic feedback. Alternatively, the boundaries may be based on anatomy such as anatomical models or tissue conditions. The processor operably coupled with the robotic arm can detect and store the boundaries for the allowable range of motion, such that the robotic arm, when switched to active mode, can use these boundaries to avoid moving outside of the allowable range of motion.

In some embodiments, a treatment probe is manually inserted within a penile urethra and placed with the distal end about 1 cm past the medium lobe and within a bladder of the patient. The probe can be imaged, for example with ultrasound such as a TRUS probe. The images of the probe may show the probe manually positioned near the final location in the patient anatomy, for example about 1 cm past the median lobe within the bladder. In some embodiments, the range of motion is manually calibrated by the medical practitioner manipulating the probe parallel to an angle of initial insertion docking the treatment probe upward in the pubic or urethral arch and restricting motion to within a range from about 3 mm to about 5 mm laterally in the X plane, within a range from about 0 mm to 10 about mm downward in the Y plane. The trained motion for the Z plane (into and out of the patient) would be set to zero cm inward toward the patient and full extraction out of the patient. For example, a 30 cm probe could be retracted as much as 30+ cm to remove it from the patient and much less if adjusting the effective area for clinical treatment.

Angularly, as measured from the physician's full insertion position, the range of safe motion within the patient depends on anatomic structures such as tissue elasticity and bony structure. An example of angular positioning with the fulcrum at the pelvic notch bone structure the allowable angular range of motion can be set to be within a range from about 0 degrees to about +/−5 degrees in the lateral X direction, within a range from about zero degrees to +/−25 degrees in the vertical direction along a Y plane, or a combination of motions within these ranges depending on the patient anatomy, for example.

Alternatively or in addition, the boundaries for the allowable range of motion of the treatment probe may be automatically or semi-automatically determined with one or more system processors in response to an automated analysis of image data of the target site such as from the imaging probe or other imaging source (e.g., a cystoscope, an external ultrasound source, a CT scanner, an MRI system, a fluoroscopic imaging system, etc.). The image data may be generated in real-time. For example, the one or more system processors may be instructed to recognize anatomy (e.g., the prostate, the external sphincter, the verumontanum, the bladder neck, etc.), and in some cases the treatment and/or imaging probes, in the image data and determine the boundaries of, or limits upon, the allowable range of motion in response.

Alternatively or in addition, the boundaries for the allowable range of motion of the treatment probe may be automatically or semi-automatically determined with one or more system processors in response to position and/or force feedback data of the treatment probe from one or more position and/or force sensors on the treatment probe and/or treatment probe robotic arm. For example, the one or more force sensors on the treatment probe and/or treatment probe robotic arm can provide tissue pressure data which may indicate areas where probe advancement is more resisted and can present risks of tissue damage.

In some embodiments, the joint sensors within the robotic arms comprise force feedback sensors to detect force to the probe inserted into patient. Alternatively, or in combination, sensors coupled to the processor can be located at one or more of the probe or at an interface between the probe and the robotic arm. For example, probe sensors within the probe can sense pressure near the distal end of the probe. The processor can be configured with instructions to adjust the distal end of the probe translationally and/or rotationally in response to the distal pressures sensed. The sensors may comprise one or more of multi plane strain gauge elements located along the probe to sense pressures of the probe against tissue. The processor can be configured with instructions to implement threshold limits to avoid undesirable tissue damage. The multiplane strain gauge elements may comprise one or more of electrical conductance thin film sensors, semiconductor sensors, piezoresistors, nanoparticle-based strain sensors, capacitive sensors, optical ring resonators, fiber optic sensors, or conductive fluid in an elastomer.

In some embodiments, a probe shaft comprises a spring constant and embedded strain gauges at periodic locations along the shaft to measure bending, and axial pressure at specific points along the shaft. These sensor measurements can be combined with the arm joint sensors. In some embodiments, the processor is configured with instructions for identifying or determining if a source of pressure resistance exists, such as one or more of a bony constraint related to proximity to bone, a tough tissue entry fulcrum, or the distal tip of the probe being forced against inner anatomy tissue. Alternatively, or in combination, the probe on the probe may comprise elastomeric tubular sheaths having exposed "touch areas" coupled with pressure sensors reporting information from elements such as rings around the probe, a linear side structure, or button sensor elements near the distal end of the probe.

With a step 620, the robotic arm is manipulated under computer control through user inputs. The user may manipulate the robotic arm motion via inputs provided to the graphic user interface of the image-guided treatment system (e.g., user interface software provided through the treatment console as described herein) or other suitable user input or control element, such as a joystick. For example, the user may affect one or more of rotation, translation, and/or adjustment of pitch angle of the treatment probe. While in active mode, the robotic arm may be configured to move only within the boundaries of allowable range of motion as set in step 615. The robotic arm, while in active mode, may be configured to retract the treatment probe from the patient, but not advance the treatment probe into the patient, to ensure safety of the patient; any advancement of the probe into the patient can be performed manually by the user. During retraction of the probe, the robotic arm may be programmed to maintain the probe on a linear track so that the z-axis position of the probe remains substantially constant.

The robotic arm and the treatment probe may be manipulated under computer control to perform a treatment protocol, which may be automated. In some embodiments, a tissue resection procedure is automatically planned based on the image data from the imaging probe or other imaging source. For example, the one or more system processors may be instructed to recognize the prostate or other relevant anatomy thereof, generate a treatment protocol in response to the locations of the anatomy and probes, and allow the user to modify and/or accept the treatment protocol before it is implemented by manipulating the robotic arm and/or treatment probe.

With a step 625, the robotic arm is automatically manipulated under computer control to adjust the position of the treatment probe. The position of the treatment probe may be adjusted according to pre-programmed parameters, user instructions, real-time feedback (from imaging, position, and/or force feedback data, for example), or combinations thereof. For example, the imaging system may be configured to detect the location of the treatment probe during treatment, for example using "smart" image recognition based on ultrasound images of the target site obtained with an ultrasound imaging probe. Based on the detected location of the treatment probe, the robotic arm may be manipulated automatically to adjust the position and/or orientation of the treatment probe, in order to align the treatment probe to the target tissue of the patient and/or to the imaging probe, and/or in order to compensate for patient movement. With a step 628, the treatment is performed.

With a step 630, the treatment probe is uncoupled from the robotic arm. When the treatment procedure is completed, the user can disconnect the treatment probe from the robotic arm, manually move the robotic arm to the side, and then remove the treatment probe from the patient.

One or more steps of the method 600 may be performed with circuitry as described herein, for example, one or more of a processor or a logic circuitry of the systems described herein. The circuitry may be programmed to provide one or more steps of the method 600, and the program may comprise program instructions stored on a computer readable memory or programmed steps of the logic circuitry such as with programmable array logic or a field programmable gate array.

Although the above steps show a method 600 of operating a robotic arm coupled to a treatment probe in accordance with some embodiments, a person of ordinary skill in the art will recognize many variations based on the teachings described herein. For example, the steps may be completed in a different order. One or more steps may be added or omitted. Some of the steps may comprise sub-steps. Many of the steps may be repeated as often as necessary or desired.

FIG. 7 shows a method 700 for operating a robotic arm coupled to an imaging probe in accordance with some embodiments.

With a step 705, an imaging probe is inserted into the patient, with the robotic arm on standby to one side of the patient, manually, semi-automatically, or automatically. For example, for an image-guided prostatic tissue resection system, the imaging probe may comprise a TRUS probe and may be manually inserted into the rectum of the patient. In some embodiments, the imaging probe is inserted concurrently with or before the treatment probe. The imaging probe may provide one or more images along the transverse plane. The imaging probe may provide one or more images along the sagittal plane which may be generated as the imaging probe (and/or an imaging transducer within the imaging probe) is advanced and/or retracted. The transverse and/or sagittal images may be combined to generate a three-dimensional image.

With a step 710, the robotic arm is coupled to the imaging probe. For example, the robotic arm and the imaging probe may be coupled together using a coupling mechanism substantially similar to that described herein with reference to the treatment probe.

With a step 715, the allowable range of motion for the robotic arm is programmed. For example, a user can manually move, rotate, and angulate the imaging probe to set the boundaries for the allowable range of motion of the imaging probe, while the probe is connected to the robotic arm with the robotic arm still in passive mode. The user may set the boundaries based on a combination of cystoscopic, ultrasound, and haptic feedback. Note that the allowable range of motion may differ from the possible range of motion of elements of the probes. This may be done to facilitate a treatment, prevent a collision between the probes or robotic arms during a treatment, and/or protect a patient from possible harm.

In some embodiments, a probe is manually positioned near the final location in the patient's rectal anatomy. The range of motion is manually calibrated by the medical practitioner manipulating the probe substantially parallel to an angle of initial insertion, for example. The medical practitioner moves the inserted probe within a range of allowable motion, for example an allowable range of motion with boundaries within a range from about 3 cm to about 5 cm along one or more of the lateral X plane or the vertical Y plane. In some embodiments, the medical practitioner moves the probe along the Z plane (into and out of the patient). In some embodiments the range of motion along the Z plane can be within a range from 0 cm inward toward the patient (zero to avoid inadvertent robotic caused rectal damage) to full extraction out of the patient. For example, a 10 cm probe could be retracted 10+ cm to remove it from the patient. Angularly, as measured from the physician's full insertion position, the range of safe motion within the patient depends on anatomic structures such as tissue elasticity and bony structure. An example of angular positioning of the probe with the fulcrum at the tissue surface (or alternatively at planes defined by bone structure), the allowable range of motion can be set from 0 to about +/−15 degrees, for example from about 0 to about +/−30 degrees in one or more of the X or Y planes. In some embodiments, the angular boundary may comprise a combination of motions corresponding to tracing a cone within these boundaries.

The processor operably coupled with the robotic arm can detect and store the boundaries for the allowable range of motion, such that the robotic arm, when switched to active mode, can use these boundaries to avoid moving outside of the allowable range of motion. Alternatively or in addition, the boundaries for the allowable range of motion of the imaging probe may be automatically or semi-automatically determined with one or more system processors in response to an automated analysis of image data of the target site such as from the imaging probe or other imaging source (e.g., a cystoscope, an external ultrasound source, a CT scanner, an MRI system, a fluoroscopic imaging system, etc.). The image data may be generated in real-time. For example, the one or more system processors may be instructed to recognize anatomy (e.g., the prostate, the external sphincter, the verumontanum, the bladder neck, etc.), and in some cases the treatment and/or imaging probes, in the image data and determine the boundaries for the allowable range of motion in response.

Alternatively, or in addition, the boundaries for the allowable range of motion of the imaging probe may be automatically or semi-automatically determined with one or more system processors in response to position and/or force feedback data of the imaging probe from one or more position and/or force sensors on the imaging probe and/or treatment probe robotic arm. For example, the one or more force sensors on the imaging probe and/or imaging probe robotic arm can provide tissue pressure data which may indicate areas where probe advancement is more resisted and can present risks of tissue damage.

With a step 720, the robotic arm is automatically manipulated under computer control to scan the tissue. For example, during the planning of the treatment procedure, the robotic arm can be pre-programmed to automatically scan the target site to render a 3-dimensional image of the target site. While in active mode, the robotic arm may be configured to move only within the boundaries of allowable range of motion as set in step 715. The robotic arm, while in active mode, may be configured to retract the treatment probe from the patient, but not advance the treatment probe into the patient, to ensure safety of the patient; any advancement of the probe into the patient can be performed manually by the user. During retraction of the probe, the robotic arm may be programmed to maintain the probe on a linear track so that the z-axis position of the probe remains substantially constant.

With a step 725, the robotic arm is manipulated under computer control through user inputs. The user may manipulate the robotic arm motion via inputs provided to the graphic user interface of the image-guided treatment system (e.g., user interface software provided through the treatment or imaging console as described herein). For example, the user may affect rotation, translation, and/or adjustment of pitch angle of the imaging probe. While in active mode, the robotic arm may be configured to move only within the boundaries of allowable range of motion as set in step 715. The robotic arm, while in active mode, may be configured to retract the treatment probe from the patient, but not advance the treatment probe into the patient, to ensure safety of the patient; any advancement of the probe into the patient can be performed manually by the user.

With a step 730, the robotic arm is automatically manipulated under computer control to adjust the position of the imaging probe. The position of the imaging probe may be adjusted according to pre-programmed parameters, user instructions, real-time feedback (from imaging, position, and/or force feedback data, for example), or a combination thereof. For example, the imaging system may be configured to detect the location of the treatment probe during treatment, for example using "smart" image recognition based on ultrasound images of the target site obtained with an ultrasound imaging probe. Based on the detected location of the treatment probe, the robotic arm may be manipulated automatically to adjust the position and/or orientation of the imaging probe, in order to align the imaging probe to the treatment probe and/or in order to compensate for patient movement. With a step 732, the treatment is performed.

With a step 735, the imaging probe is uncoupled from the robotic arm. When the treatment procedure is completed, the user can disconnect the imaging probe from the robotic arm, manually move the robotic arm to the side, and then remove the imaging probe from the patient.

One or more steps of the method 700 may be performed with circuitry as described herein, for example, one or more of a processor or a logic circuitry of the systems described herein. The circuitry may be programmed to provide one or more steps of the method 700, and the program may comprise computer-executable program instructions stored on or in a computer readable memory or programmed steps of the logic circuitry such as with programmable array logic or a field programmable gate array.

Although the above steps show a method 700 of operating a robotic arm coupled to an imaging probe in accordance with some embodiments, a person of ordinary skill in the art will recognize many variations based on the teachings described herein. For example, the steps may be completed in a different order. One or more steps may be added or omitted. Some of the steps may comprise sub-steps. Many of the steps may be repeated as often as necessary or desired.

FIG. 8A illustrates a configuration of a treatment probe 450 and an imaging probe 460 during treatment of a patient with the treatment system as described herein. It is desirable to ensure that the treatment probe and the imaging probe outside of the patient body do not collide or otherwise interfere with one another during use of the system, thereby maintaining the precision of movement of the probes and sterility of the system. The robotic arms as described herein, coupled to the treatment probe and the imaging probe and configured to control their movement, may be configured to maintain boundaries to prevent collision or interference between the two probes. For example, one or both of the first robotic arm coupled to the treatment probe and the second robotic arm 444 coupled the imaging probe may be configured to sense a distance 520 between the two probes, and maintain the distance substantially constant or greater than a minimum threshold value to prevent collision. Alternatively, or additionally, as described with reference to the methods shown in FIGS. 6 and 7, the user may program an allowable range of motion for one or both of the treatment probe and the imaging probe so as to set boundaries for the range of motion that would prevent collision or interference between the probes.

For example, before the robotic arms are switched to active mode, the user may rotate one or both of the probes over a range of allowable pitch angles 525 of the probes to program the allowable range of motion for the probes within which the two probes do not contact one another.

With additional reference to FIG. 8B, the robotic arm 442 is coupled to a motor pack 802, as described herein. The motor pack 802 may be coupled to a hand piece 804 of a probe 450. In some embodiments, one or both of the robotic arms coupled to the treatment probe and the imaging probe may comprise one or more feedback sensing mechanisms. For example, the first robotic arm 442 and/or the second robotic arm 444 may be operably coupled with a force sensor configured to detect a compression of the tissue anterior to the treatment probe and/or imaging probe. In some embodiments, the force exerted by the imaging probe is within a range from 0 to 39 Newtons exerted upward, thereby compressing the tissue to achieve visualization of the treatment probe and target tissue region. In some embodiments, the force exerted by the treatment probe is related to the position of the probe within the lumen such as the urethra. In some embodiments the force is related to a fulcrum or pivot at the urethral notch and a pivoting to lift the target anatomy. These forces can be, respectively, within a range from 0 to 98 Newtons against the bony structure and within a range from 0 to 19 Newtons on the target anatomy, such as the prostate.

According to some embodiments, one or more X-direction force sensors 810, one or more Y-direction force sensors 812, and/or one or more Z-direction force sensors 814 may be provided on the robotic arm 442, the hand piece 804, and/or the probe 450. The one or more force sensors may comprise a strain gauge, a pressure sensor, or a piezo electric transducer, for example. In some embodiments the strain gauge comprises any of a number of configurations of a Wheatstone bridge. A Wheatstone bridge circuit converts a small change in resistance into a measurable voltage differential, which can be equated to an applied force. The force sensor may be coupled to the handpiece, such as any handpiece embodiment described herein. In some instances, one or more force sensors are operatively coupled to the imaging probe, treatment probe, or both.

In some embodiments, the circuitry for operating the force sensor is insulated and isolated from the imaging probe and treatment probe. This allows the probe to satisfy any patient leakage current requirements and reduces any noise that would be picked up by the probe, thus enhancing the signal to noise (S/N) of the force sensor. In some embodiments, the signal wires from the force sensor may be twisted together and optionally may be shielded to maintain signal integrity, improve immunity, and maintain an adequate S/N ratio. The force sensor may be formed of any suitable material, and in some cases, is formed of a biocompatible material for portions of the sensor that may come into contact with a patient before, during, or after treatment.

In some embodiments, one or more force sensors are sized to fit on or within the probe shaft, such as the imaging probe or treatment probe shaft. The force sensor may be configured with any suitable strain sensitivity "k," which is a proportional factor between the relative change of the resistance. The strain sensitivity is a figure that is dimensionless and is called the Gauge Factor ("GF"). A linear pattern strain gauge may be used to measure strain in a single direction on the handpiece. Conductive signal wires may be bonded to the pads of the sensor which carry the signal to an input amplifier. One or more sensors may be bonded to one or more probes on a carrier substrate that may insulate the sensor from any metal of the probe, such as a metal probe shaft.

Displacement in the Z-direction of the handpiece can be detected by a spring and sensor 814. Utilizing this configuration, the entire probe assembly can be able to slide a suitable distance to provide protection from a probe being driven into a tissue wall. The probe assembly may be arranged on a sliding trolley 820 which can be sprung against a simple spring to provide a constant and known force "K" spring constant. Accurate distance measurement of the handpiece, such as by displacement of the trolley, is possible over a short distance with a suitable arrangement, such as less than 2 inches. Other positional encoder linear sensors may be used in combination, or in the alternative. For example, a linear variable differential transformer (LVDT), is an electromechanical sensor used to convert mechanical motion into a variable electrical current and can be used to measure resistance to the insertion force of the probe. An optical encoder, or any of a number of suitable inductive linear encoders may also or instead be used. A sensor can measure a force based upon an inductive linear encoder 824 and may be arranged for non-contact to ensure high reliability. A high-resolution encoder 824 may be provided for a linear resolution of between about 15 micrometers for a digital encoder, to about 54 micrometers, such as for an analogue encoder.

One or more sensors may be provided on one or more robotic arms to measure position, orientation, force, or some other parameter. In some instances, two sensors may be part of the robotic arm assembly and can be utilized to determine unintended movements. These sensors can be internal encoders which may be located one or more joints of the robotic arm and may be an inertial measurement unit (IMU) 822. An IMU is an electronic sensor device that measures and reports one or more parameters, such as a force, an angular rate, and/or the orientation of the sensor, and may use a combination of accelerometers, gyroscopes, and/or magnetometers. Some IMUs that are suitable for incorporation into one or more robotic arms may have a full-scale acceleration ranges of ±2/±4/±8/±16 g ("g" values in relation to acceleration due to gravity) and a wide angular rate ranges of ±125/±250/±500/±1000/±2000/±4000 degrees per second ("dps"). The IMUs can detect forces on the robotic arm and communicate the magnitude and/or direction of an external force to the computing devices, such as a robotic control system. The one or more IMUs 822 can provide feedback which can be used to control the one or more robotic arms to compensate for vibration, positional awareness, and stabilization compensation.

As described herein, the robotic arm 442 can be docked with the probe 450 by the use of sensors to aid in one or more of coarse positional alignment, intermediate positional alignment and fine positional alignment. For example, the probe may be associated with a beacon 830, such as an IR beacon, and the robotic arm 442 may carry an IR receiver 832 that is able to detect an emission from the IR beacon 830 for coarse alignment. One or more alignment fiducials 834 may be associated with the probe 450 and one or more alignment sensors 836 may be associated with the robotic arm 442. The alignment sensors 836 are able to detect the position of the alignment fiducials, and thus determine the position of the robotic arm 442 relative to the probe 450, as described herein. In some embodiments, proximity sensors such as Hall effect sensors or proximity switches are used to detect the alignment between the probe and the arm in order to engage the probe with the arm, for example to latch the probe onto the arm when the arm has been suitably manipulated into position.

In some embodiments, when the treatment has been completed, the arm can be decoupled from the probe while the user holds the probe, and the arm drawn away from the probe, for example the arm may automatically be drawn away from the probe.

The one or more computing devices operably coupled with the robotic arms (such as the processor of the console 420 or console 490 as described herein) may comprise instructions to control movement of the robotic arms in response to forces detected by the sensor, for example to prevent over-compression of the anterior tissue and resultant damage to the tissue and/or the probe. In the exemplary use case of the treatment system for prostatic tissue resection, the treatment probe is ideally positioned at the anterior center of the prostate cavity of the patient, but without over compressing the anterior prostate to prevent inadvertent injury to the urethra/prostate (e.g., excessive bleeding, necrosis, perforation of tissue) and/or damage to one or both of the imaging probe and the treatment probe.

Similarly, the imaging probe, which can be a TRUS probe, is ideally positioned within the rectum of the patient with adequate anterior compression to view the prostate and the treatment probe, but without over compressing the tissue, so as to avoid inadvertent injury to the rectum (e.g., bleeding or perforation of the tissue) and/or damage to one or both of the imaging probe and the treatment probe. The treatment probe, the first robotic arm coupled thereto, the imaging probe, and/or the second robotic arm 444 coupled thereto may be provided with the force sensor configured to detect anterior compression of the tissue with the probe. The detected force level may be communicated to the processor operably coupled with the robotic arm and compared to a threshold value of force pre-programmed or stored in the memory of the computing system. If the detected force exceeds the threshold, then the movement of the robotic arm may be adjusted to move the probe away from the anterior tissue, thereby at least partially relieving compression of the anterior tissue.

Another exemplary feedback sensing mechanism may comprise position and/or motion sensors operably coupled with the first and/or second robotic arm 444. The one or more computing devices operably coupled with the robotic arms may comprise instructions to control movement of the robotic arms in response to the position and/or motion detected by the sensors, for example to adjust the position of the treatment and/or imaging probe in response to patient movement during a treatment and/or scanning procedure. Patient movement while a rigid element such as the treatment probe or the imaging probe is positioned inside the patient's body could potentially cause injury to the patient and could necessitate the removal of the probe during the movement and subsequent re-positioning of the probe.

A robotic arm that automatically adjusts the position of the probe in response to sensed movement of the patient can improve the safety as well as the efficiency of the procedure. One or more position or motion sensors, such as coils and/or accelerometers, may be attached to the patient, and the sensor may be operably coupled with the computing devices controlling the robotic arms. The sensors may be configured to generate small, localized electromagnetic fields or other signals to help determine the location and/or movement of the patient, for example. The computing device or processor can receive the detected patient movement data, and accordingly adjust movement of the robotic arms to substantially match patient movement, such that the probe coupled to the robotic arm can remain within an acceptable range of positions with respect to the tissue or patient organ. In some embodiments, the processor is configured to interrupt the treatment if the force to the sensor exceeds a threshold amount.

Optionally, in some embodiments, the robotic arms may be configured to automatically move in a linked manner. For example, if a user of the system moves the first robotic arm, the second robotic arm 444 may be configured to automatically adjust its position accordingly. In the exemplary use case of the treatment system for prostatic tissue resection, the prostate of the patient may not be symmetrical in anatomy, and the user may need to adjust the position or orientation of the treatment probe accordingly (e.g., push the probe to a side, adjust the pitch angle of the probe, etc.). The robotic arm coupled to the imaging probe may be configured to automatically detect adjustments made to the robotic arm coupled to the treatment probe and make corresponding adjustments to the imaging probe position and/or orientation. Such linked movement of the two robotic arms may be useful for maintaining the treatment and imaging probes at a desired positional relationship with respect to one another, for example with the elongate axis of the treatment probe substantially aligned with the elongate axis of the imaging probe.

Figure 9A:
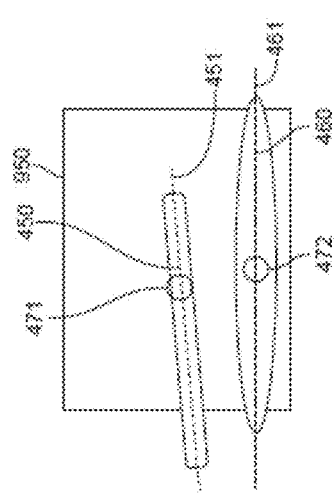
FIGS. 9A, 9B, and 9C schematically illustrate an alignment of a treatment probe axis with a sagittal plane of an imaging probe, in accordance with some embodiments.
Figure 9B:
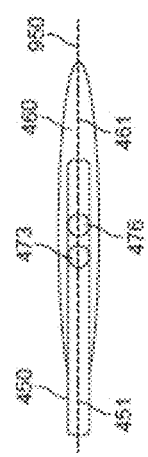
Figure 9C:
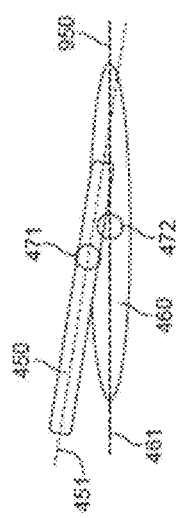

FIGS. 9A-9C schematically illustrate an alignment of a treatment probe axis 451 with a sagittal plane 950 of an imaging probe 460. FIG. 9A is a side view of a treatment probe 450 that is inclined relative to an imaging probe 460. The treatment probe 450 comprises an elongate axis 451, and the imaging probe 460 comprises an elongate axis 461 that provides a reference for the images generated by the imaging probe. The elongate axis 461 may at least partially define a sagittal image plane 950. FIG. 9B is a top view of the treatment probe 450 substantially aligned with the sagittal image plane 950. When the treatment probe axis 451 is substantially aligned with the sagittal image plane 950, a substantial portion of the treatment probe is within the field of view of the ultrasound probe and visible in the sagittal image. In some embodiments, the two probes are substantially aligned when the elongate axes are aligned to within about 5 degrees of each other with respect to a plane perpendicular to the sagittal image plane. In some cases, with greater angles of inclination between the probes, the treatment probe will extend transverse to the field of view of the ultrasound probe, and only the portion of the probe within the field of view of the ultrasound probe will be visible in the ultrasound image.

When the probes are substantially aligned within the sagittal image plane but inclined at an angle as shown in FIG. 9A, the treatment probe and tissue can appear rotated in the sagittal image and the acceptable amount of rotation can be greater than 5 degrees, for example. FIG. 9C is a top view of the treatment probe 450 traversing a sagittal image plane 950. When the imaging probe is not sufficiently aligned with the treatment probe, the treatment probe can appear distorted in the sagittal plane image, with only a portion of the treatment probe extending through the sagittal field appearing in the image. In some embodiments, the treatment and imaging probes may comprise one or more sensors to confirm the desired alignment (parallel and/or coplanar) of the probes to one another. For example, the system may comprise a first orientation sensor 473, and a second orientation sensor 476 on the treatment probe 450 and the imaging probe 460, respectively. In some embodiments, the first orientation sensor, and a second orientation sensor 476 comprise magnetic elements, Hall effect sensors, dials, variable resistors, potentiometers, accelerometers, or any combination thereof that may indicate the relative position and orientation of the probes to one another.

In some embodiments, the angle of the sagittal plane of the ultrasound imaging probe can be rotated by rotating the ultrasound imaging probe about the elongate axis of the ultrasound imaging probe. For example, in some patients, the prostate is not symmetrical, or the urethral notch is deformed, and imaging probe and the treatment probe can be located on opposite sides of the patient or at least offset relative to each other with respect to a midline of the patient, and rotation of the imaging probe about its elongate axis can rotate the sagittal plane of the ultrasound probe and bring the treatment probe and tissue treatment region within the field of view of the ultrasound imaging probe. The alignment, orientation, and relative positioning of the treatment and imaging probes may continue to be monitored during a treatment procedure.

When the treatment probe and the imaging probe are insufficiently aligned, the user can use images of the treatment probe obtained with the imaging probe to align the treatment probe with the imaging probe, for example by providing user inputs into the GUI for controlling the robotic arm coupled to the treatment probe or the imaging probe. Alternatively, or additionally, the robotic arms may be programmed to automatically adjust movements to maintain the probes in sufficient alignment, as described herein. For example, when a user adjusts the position or orientation of the treatment probe by controlling the first robotic arm coupled to the treatment probe, the second robotic arm 444 coupled to the imaging probe may automatically detect the adjustments made to the first robotic arm and make corresponding adjustments to substantially match the pitch, roll, yaw, lateral and/or linear position of the treatment probe along the treatment probe axis.

As will be described in greater detail, in some embodiments, images of the treatment probe obtained by the imaging probe may be used to automatically cause a repositioning, translation or reorientation of one or both probes to prevent a collision between the probes and/or harm to a patient's tissue or organs. In such embodiments, a computing device may determine that based on the images, the probes are too close to each other or to an area of tissue or an organ. In some embodiments, a computing device may use data or images regarding the range of motion of one or both probes and images of the treatment probe obtained by the imaging probe (and also possibly images of tissue or organs surrounding the imaging probe or treatment probe) to determine that a limit or constraint should be placed on the range of possible motion or the range of the trained allowable motion of one or both probes. This limit or constraint may be implemented by limiting or constraining the movement of the probes by the robotic arms, for example.

To provide automatically linked movement of the two robotic arms, a calibration step may be added to the treatment procedure wherein each arm identifies its position with respect to the other arm. For example, each robotic arm may comprise a "target" on the arm of a known location; during the calibration procedure, the user may manipulate the first arm to touch the target located on the second arm with the first arm coupling structure, and manipulate the second arm to touch the target located on the first arm with the second arm coupling structure. Automatically linking movement of the two robotic arms can thus facilitate the treatment procedure by eliminating the need for the user to separately adjust the movement of a second arm after moving a first arm. In addition, the linked movement of the two arms can aid in improving safety and efficiency of the treatment procedure in case the patient moves while the probes are inserted into the patient's body, as described herein.

Optionally, in some embodiments, the robotic arm coupled with the treatment probe may be configured to move the treatment probe along a pre-programmed treatment profile for performing treatment of the target site. For example, the treatment profile may comprise a tissue resection profile of the target site, which may be programmed by the user of the treatment system and stored in a memory of the one or more computing devices operably coupled with the robotic arm. Further details regarding automated treatment using programmed treatment profiles may be found in PCT Publication No. WO2013/130895, previously incorporated herein by reference.

Optionally, in some embodiments, the robotic arm coupled with the imaging probe may be configured to move the imaging probe along a pre-programmed imaging profile for generating a 3-dimensional rendering of the target site, before and/or during treatment with the treatment probe. A 3-dimensional image of the target site may be derived from a biplanar imaging probe by: 1) rotating the imaging probe in place with the imaging probe capturing sagittal view images of the target site, then interpolating the sagittal view images, or 2) translating the imaging probe across the target site (along the z-axis of the probe) with the imaging probe capturing transverse view images of the target site, then interpolating the transverse view images. To improve the efficiency of 3D image rendering and the resolution of the resultant 3D images, the robotic arm may be configured to rapidly scan the target site along a pre-programmed imaging profile, and the 3D image may be generated using software to render a 3D image of the treatment site in substantially real-time. The pre-programmed imaging profile may be stored on or in a memory of the one or more computing devices, and may comprise a plurality of sagittal view scans taken at predetermined time intervals while the imaging probe rotates in place, and/or a plurality of transverse view scans taken at predetermined time intervals while the imaging probe translates across the target site (along the z-axis or elongate axis of the imaging probe).

The automatic, computer-controlled scanning of the target site with the imaging probe using the robotic arm can also be used to generate useful information regarding the target site for additional treatment. For example, the imaging probe may be configured to perform a color/Doppler scan of the target site after a resection procedure, in order to locate bleeding sites within the target site that require hemostasis. The imaging probe may also be used to monitor or examine a location in a patient's body after (or as part of) other types or procedures, including planning tissue removal, treatment profiles, or monitoring during and after a procedure such as a colonoscopy and associated biopsy.

In some embodiments, the Doppler ultrasound image shows blood moving away from the ultrasound probe as blue and blood moving toward the ultrasound probe as red. In some embodiments, the tissue resection profile can be adjusted prior to tissue resection so as to decrease and in some instances avoid resection of blood vessels present in the Doppler ultrasound image. For example, the ultrasound image may comprise a 3D ultrasound image and a 3D resection profile adjusted to decrease or avoid blood vessels.

Figure 10:
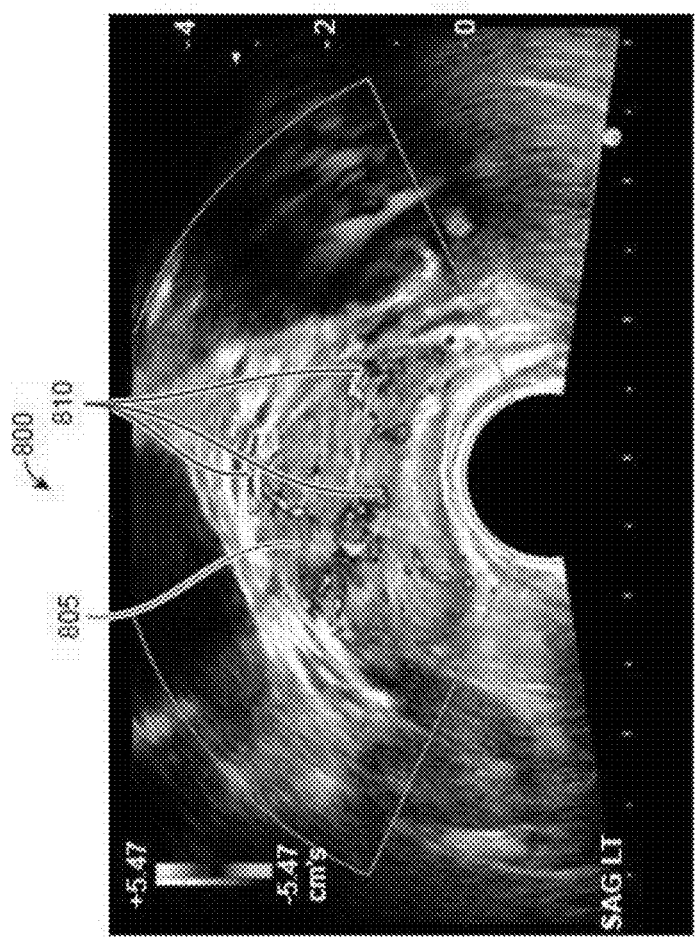
FIG. 10 shows an intra-operative image of a surgical field including the identification of bleeding sites, in accordance with some embodiments.

FIG. 10 illustrates the identification of high blood perfusion sites 810 from an ultrasound image 800 of a tissue 805 of a patient. As described herein, the robotic arm coupled to the imaging probe may be automatically moved to obtain scans from the imaging probe while the imaging probe operates in Doppler imaging mode. The high blood perfusion sites 810 can be identified from the resultant Doppler scan images, based on the detection of blood flowing closer to or farther away from an imaging plane of the imaging probe. In some cases, the high blood perfusion sites 810 comprise bleeding sites, and based on the Doppler information, the user can efficiently locate and treat the bleeding, for example by using focal cautery or hemostatic agents such as gels and matrices. This can reduce bleeding, cautery time and heat or other potentially negative effect on the tissue. The high blood perfusion sites 810 may also, in some cases, comprise abnormal or even cancerous tissue growths. These areas may be flagged or identified for subsequent treatment. For example, normal tissue may be resected around abnormal tissue to leave islands of abnormal tissue that are later treated such as with local drug delivery. In some embodiments, the robotic arms may be configured to automatically apply a cauterization tool (RF or laser for example) to treat an area of tissue that is bleeding based upon the data received form the color Doppler imaging.

The 3-dimensional scan of the target site using the imaging probe may also be used to identify tissue anomalies at the target site, such as tumors. For example, tumors may be identified from the images of the target site obtained with the automated scanning of the target site with the imaging probe, based on differences between hyperechoic and hypoechoic areas of the imaged tissue. Robotically scanning of the target site can improve the speed of image analysis and therefore the accurate detection of tissue anomalies. In addition, the imaging probe may be operated in Doppler imaging mode during the automated scanning to identify regions of higher blood flow, which can correspond to locations of potential cancer. Biopsies may be performed at the identified regions of tissue to improve the detection of cancer.

The imaging probe may also be used to monitor or examine a location in a patient's body after (or as part of) other types or procedures, including planning tissue removal, treatment profiles, or monitoring during and after a procedure such as a colonoscopy and associated biopsy.

Figure 11:
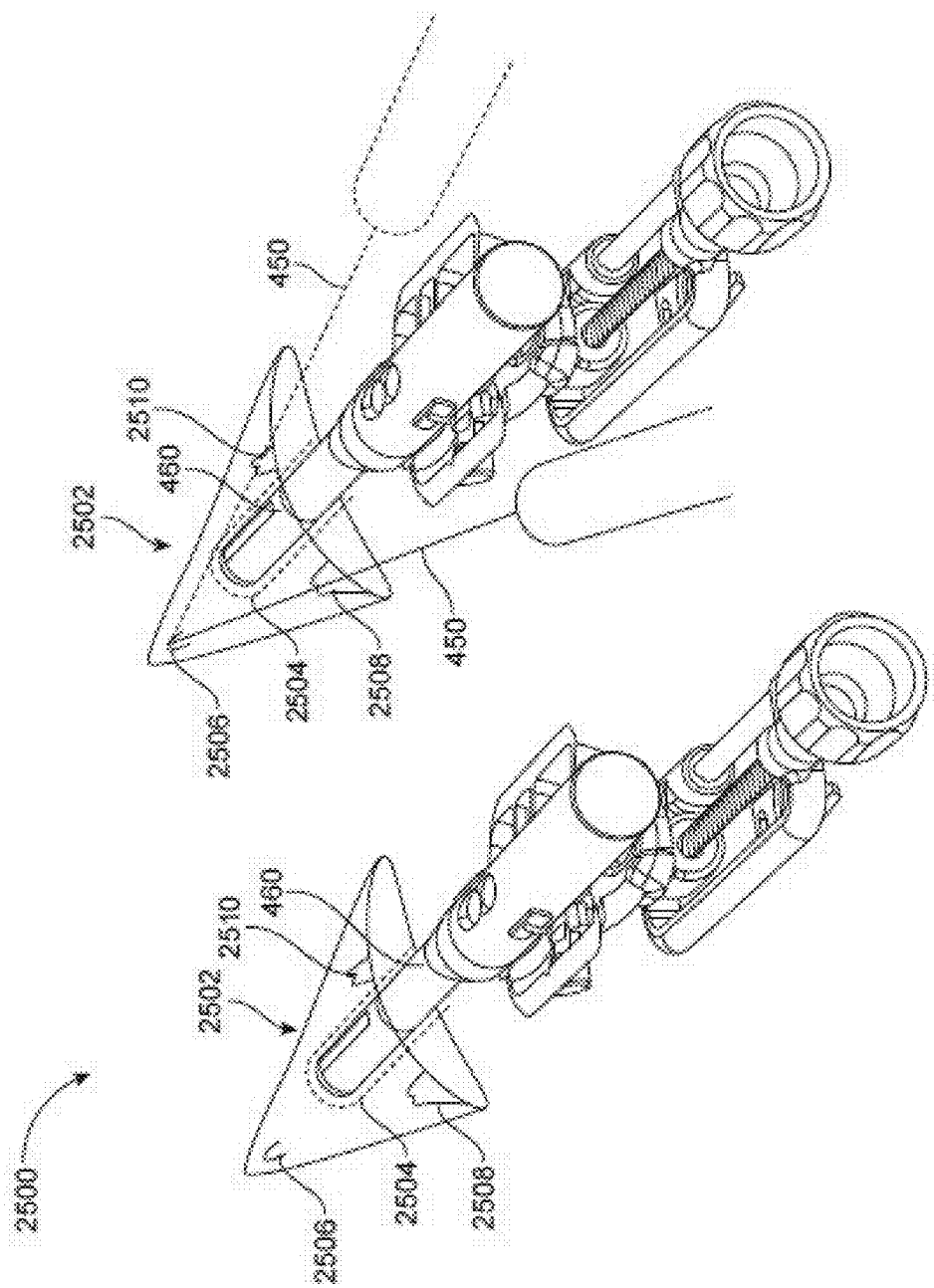
FIG. 11 illustrates a system for locating and calibrating one or more probes, in accordance with some embodiments.

FIG. 11 illustrates a system 2500 for one or more of locating a probe, calibrating a probe, or training a system with calibrated probe movements. In some embodiments, a calibration device 2502 comprises receptacles to receive the treatment probe 450 and the imaging probe 460. The receptacles are sized and shaped to receive the probes and to allow the probes to move into positions that may be used during surgery. The positions of the arms and probes can be monitored during the calibrated movement prior to placement of the probes in the patient.

In some embodiments, the processor is configured with instructions to enable the system to receive or "learn" from mechanical movements of the probe to establish one or more boundaries or constraints on probe positioning, orientation or movement. This may be done, for example for purposes of training the system to avoid collisions between probes, between a probe and a robotic arm, or between robotic arms. The teaching or training process may serve to constrain or limit the possible range of motion of a probe or probes to an allowable range of motion. In some embodiments, the processor is configured to implement a "teaching session" or training session to establish the boundaries or limits on a range of motion, for example, prior to placing one or more of the probes within the patient. During this teaching session a sterile protective calibrated guide 2502, also referred to as a calibration device, can be provided and the imaging probe 460 can be inserted therein and be used to measure geometric position data for incorporation into a positional database of the robotic arm.

In some embodiments, this guide comprises one or more of a capture lumen 2504 for receiving the imaging probe 460, a touch point 2506 for identifying the tip of the treatment probe 450, one or more dual notch structures 2508, 2510 for identifying the linear shaft location relative to the imaging probe 460, or a planar surface identifying 'do not cross' anatomical planes. Alternatively, or in combination, a plurality of cameras and machine vision software instructions can be used to measure the probe positions in 3D space relative to their respective origins and create a database of allowable relative positions between the two probes.

A calibration device 2502 may be sterile and provided with features that enable positioning onto a first probe 460 and placement for calibration of second probe 450 relative to the first probe 460. A capture lumen 2504 or open structure provides one way to position first probe 460 into a known position and orientation. The first probe 460 may be moved within the capture lumen 2504 with controlled depth of placement into the calibration device 2502 and an envelope of its spatial boundary, e.g., a bounding volume or representation of its allowed range of motion, may be created and saved to a database.

In some embodiments, the calibration device 2502 includes a tip location pocket 2506 to detect contact with the tip of the second probe 450. A first notch structure 2508 provides a guide for the shaft of the second probe 450 as the second probe 450 is advanced to the touch point 2506. The combination of the first notch structure 2508 and the touch point 2506 thus provides an instructional path for placement of the second probe 450, the positions of which can be stored in the positional database, which also stores the relative locations of the first probe 460 and the second probe 450.

With the tip of a second probe in the tip location pocket of the calibration device 2502 the shaft of the second probe can be positioned relative to the shaft of the first probe and a signal can be sent to a processor to note the positions of both robotic arms holding the first probe and second probe.

Similarly, the shafts of the first probe 460 and the second probe 450 can be moved to another spatial orientation relative to each other, such as by advancing the second probe 450 along the second notch structure 2510 and a calibration signal can be sent to the processor to store the relative position of the first probe and second probe.

Additionally, the calibration device 2502 can be configured to accept a second probe feature to detect and determine a rotational assurance of the second probe 450 and, similarly, the rotational position of the first probe 460 which may be used to align the treatment probe nozzle relative to both a transverse and sagittal plane of an ultrasound probe, for example.

The calibration device 2502 thus may provide a secure physical capture region to assure simple placement and docking of a probe tip against the calibration device 2502, the position and orientation of which can be stored in a spatial database to teach the robotic arm controller system an acceptable spatial envelope of relative position and orientation of the first probe 460 with respect to the second probe 450.

The methods and apparatus disclosed herein can be configured in many ways and may comprise fiducials and a processor configured with instructions to provide navigation and surgical guidance to a user such as a surgeon. For example, one or more of the imaging probe 460 (e.g., TRUS probe), the treatment probe 450, the proximal end of the treatment probe 450, the proximal end of the imaging probe 460, or the robotic arm may comprise navigation fiducials. These navigational fiducials can be detected with sensors to provide position and orientation information of the treatment probe 450 and imaging probe 460 relative to the patient and a fixed reference frame such as a base as described herein. The fiducials may comprise reflective structures, energy emitting structures, coils, magnets or visual references, for example. These fiducials can provide positional information to the computing navigation system to inform a user of errant motion. The positional information can be used to measure and control the location of the treatment and imaging probes and movement. The positional information can also be shown on a display visible to a user. The processor may comprise instructions to show treatment fiducials on a display in relation to target locations on a patient and register real time images of the patient with the target treatment profile in real time, for example.

As described herein, the positioning of the elements of the system, both with respect to a patients' tissue and organs, and with respect to each other is of great importance for the safe and effective performance of a procedure by a physician. For example, it is important that the robotic arms not collide with each other and that the probes not collide with each other when placed inside a patient. This means that the absolute and relative location, positioning and orientation of both the robotic arms and probes is preferably monitored and able to be limited or constrained to prevent harm. In some embodiments, this can be accomplished by defining protection regions or zones, defining exclusive operating or treatment areas, establishing "virtual" walls or features to constrain the motion or positioning of a probe, etc.

As described herein, the monitoring and constraining of the location, position, orientation, and motion of the robotic arms and probes may be accomplished by one or by a combination of processes that will be described. These processes may generally be referred to as layers or degrees of constraint and include (1) the possible or potential range of motion of the elements of a probe or probes, (2) constraints on the possible range of motion introduced by a physician during a training or teaching process and thereby defining an allowable range of motion, and (3) constraints or limitations resulting from the interpretation of images and/or other data obtained during a procedure that indicate a potential risk of collision or harm to a patient.

In some embodiments, the location, positional or orientation information is used to monitor relative motion and as a feedback loop for controlling intentional motion or responding to unintentional motion.

Figure 12:
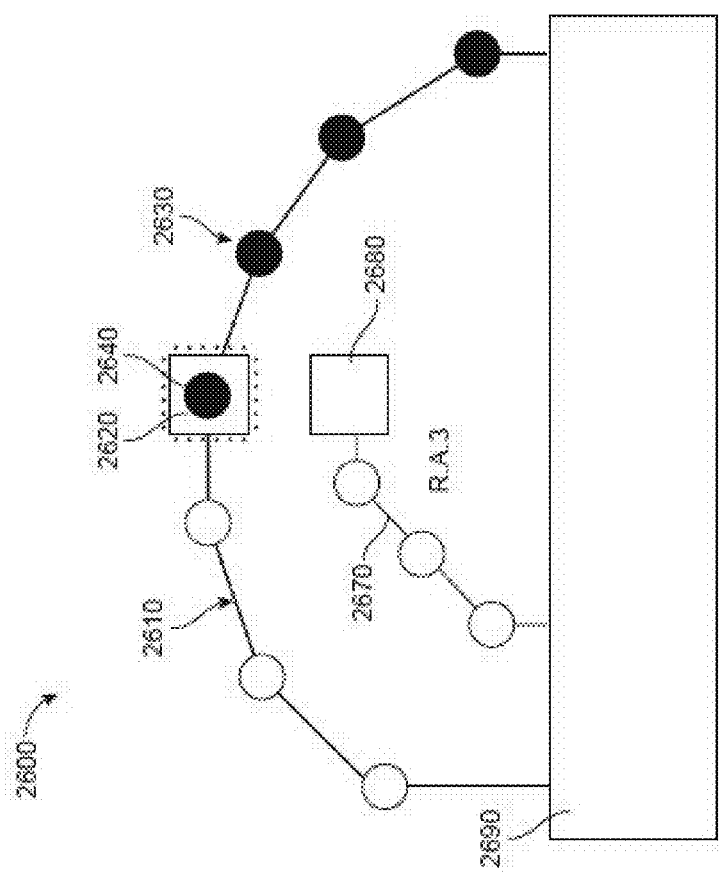
FIG. 12 illustrates an arm coupled to a sheath, a robotic arm coupled to a treatment probe, and an arm coupled to an ultrasound probe, in accordance with some embodiments.

FIG. 12 illustrates a system 2600 comprising an arm 2610 coupled to a sheath 2620, a robotic arm 2630 coupled to a treatment probe 2640, and an arm 2670 coupled to an ultrasound probe 2680. The arms are coupled to a base 2690, which may comprise any suitable base as described herein, such as a crossbar coupled to rails of a patient support, for example. The arm 2610 may comprise any arm as described herein, and may comprise a robotic arm, or a manually adjustable arm configured to lock into position, for example.

The sheath 2610 is configured for insertion into a lumen of the patient such as a urethra and may comprise a stiff sheath or a flexible sheath, for example. The robotic arm 2630 may comprise any suitable robotic arm as described herein. The treatment probe 2640 may comprise any suitable treatment probe as described herein. The arm 2670 may comprise any suitable arm as described herein, an may comprise a manual lockable arm or a robotic arm as described herein. The ultrasound probe 2680 may comprise any suitable ultrasound probe as described herein, for example a TRUS probe. The robotic arms, treatment probe and ultrasound probe are operatively coupled to a processor as described herein.

Figure 13:
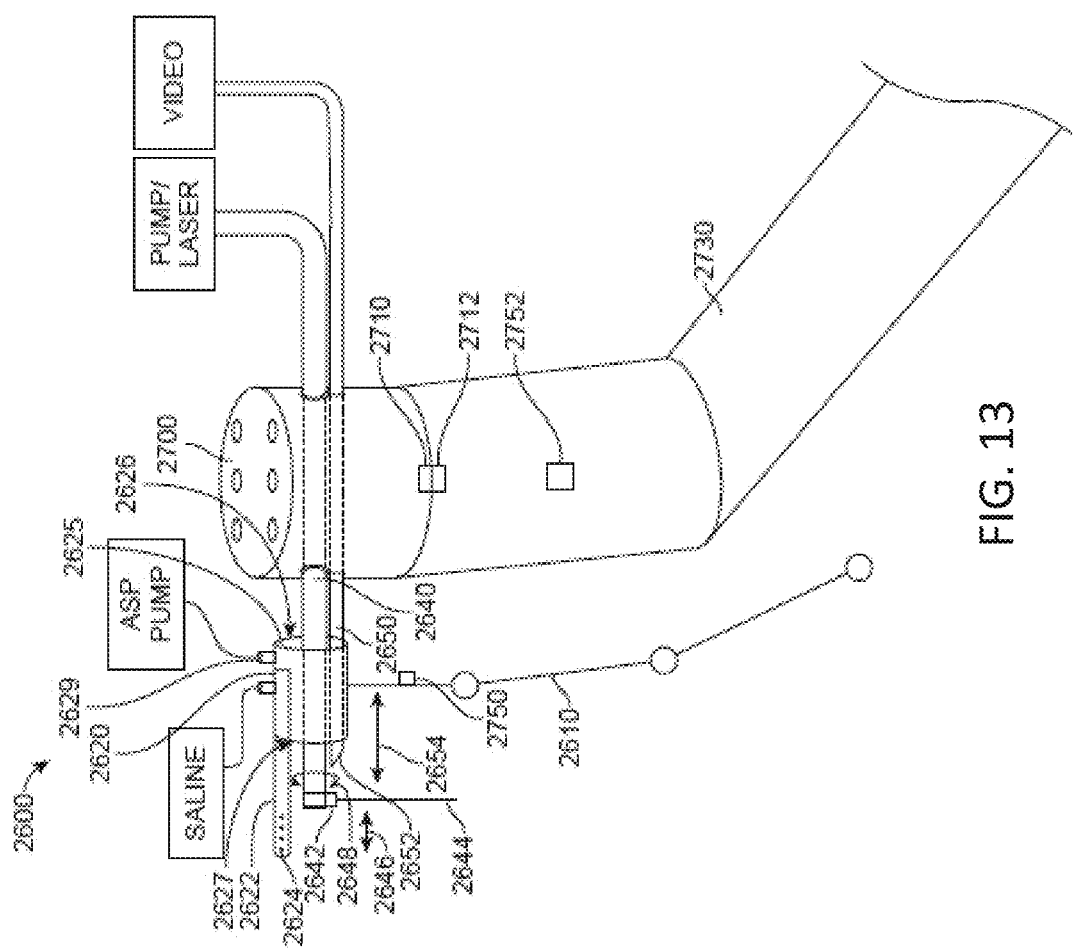
FIG. 13 illustrates a system comprising a robotic arm coupled to a treatment probe and an arm coupled to a sheath as in FIG. 12.
Figure 26:
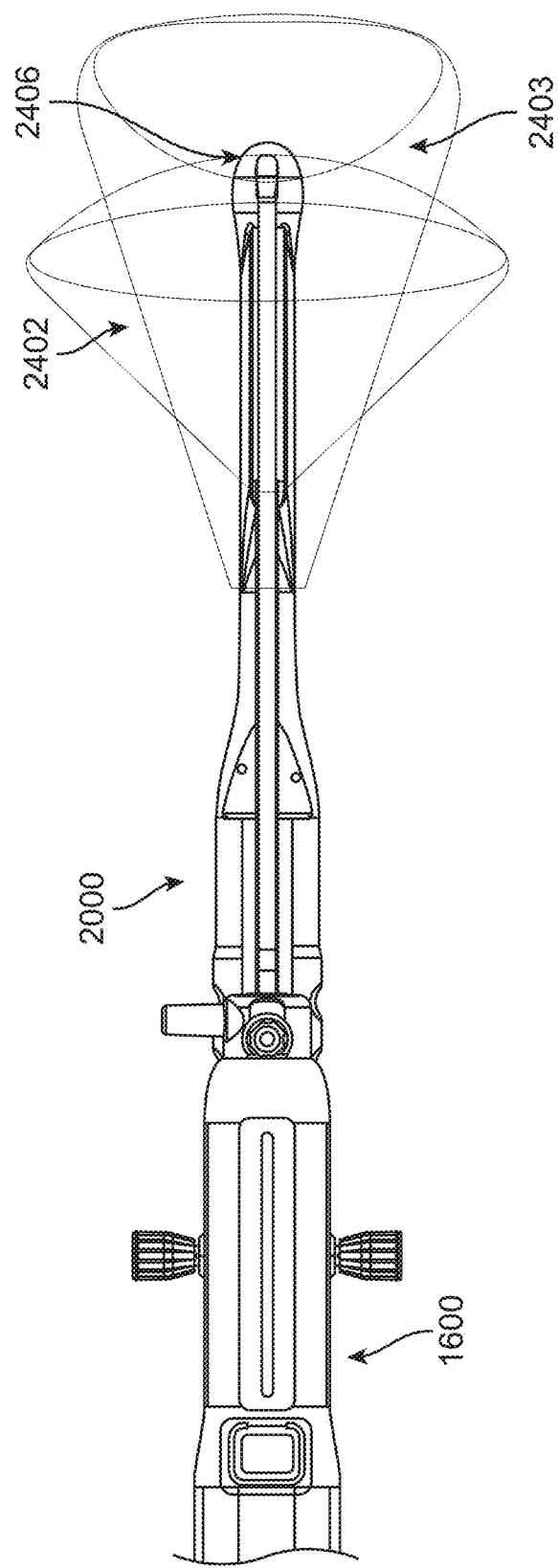
FIG. 26 illustrates a top view of the treatment probe and imaging probe of FIG. 25A and shows the respective ranges of motion overlaid with each other when the probes are separate but colinear or parallel to each other, in accordance with some embodiments.

FIG. 13 illustrates a robotic arm 2630 coupled to a treatment probe 2640 and an arm 2610 coupled to a sheath 2620 as in FIG. 26. The sheath 2620 is coupled to arm 2610. In some embodiments, the sheath 2620 comprises an irrigation lumen 2622 extending to one or more openings 2624 to irrigate the surgical site. The irrigation lumen can be connected to a source of irrigation fluid such as saline. The sheath may comprise a lumen 2626 sized to receive the treatment probe. The lumen 2626 comprises a proximal opening 2625 and extends to a distal opening 2627. In some embodiments, the sheath 2620 comprises an aspiration channel 2629 extending to an opening into lumen 2620 to fluidically couple the lumen 2626 to an aspiration pump to remove resection products. The treatment probe 2640 is coupled to a source of energy as described herein such as a laser, water pump, or electrical source, and comprises an energy release structure such as nozzle, optical fiber end, aperture, or electrode to direct energy toward the tissue. The treatment probe is configured to translate 2646 and rotate 2648 energy 2644 from the treatment probe. An endoscope 2650 extends into the sheath. The endoscope comprises a viewing port such as a viewing port of an endoscopic camera 2652, which is configured to translate 2654. The endoscope is coupled to a video display to view the treatment probe and treatment site with the endoscope.

A coupling 2700 is coupled to an end portion of the robotic arm 2630. The coupling 2700 comprises one or more engagement structures 2710 to couple to the end portion of the robotic arm. The robotic arm 2630 comprise one or more corresponding engagement structures 2712 to connect to the coupling 2700 to the robotic arm. In some embodiments, the coupling 2700 comprises internal structures such as linkages and actuators as described herein to translate one or more of the treatment probe, the endoscope, the irrigation lumen or the aspiration lumen relative to the robotic arm. In some embodiments the coupling 2700 is configured to rotate the treatment probe independently of the endoscope, the irrigation lumen and the aspiration lumen. In some embodiments, the coupling 2700 comprises a structure to receive a treatment probe and define an orientation of the treatment probe with respect to the coupling. The structure to receive the treatment probe may comprise one or more of an aperture or a channel coupled to the linkage, for example. In some embodiments, the coupling 2700 comprises an engagement structure to couple to an end portion of a robotic arm to establish an orientation of the treatment probe with respect to the end portion of the robotic arm.

In some embodiments, one or more of the arm or the sheath comprises a sensor 2750 to determine the orientation of the sheath when placed in the patient. In some embodiments, the robotic arm 2752 comprises an orientation sensor 2752 to determine the orientation of the treatment probe 2640 coupled to the robotic arm. Alternatively, or in combination with the sensors, the joint states of the robotic arm 2630 can be used to determine the orientation of the treatment probe, and the joint states of the arm 2610 can be used to determine the orientation of the sheath.

In some embodiments, the treatment probe comprises an elongate axis and the sheath comprises an elongate axis to receive the treatment probe.

The system can be configured in many ways to treat the patient in many ways. In some embodiments, the sheath is sized and shaped for insertion into the patient. The sheath comprises an elongate axis, and an arm is coupled to the sheath. The treatment probe comprising an energy source and an elongate axis. The treatment probe sized and shaped for insertion into a lumen of the sheath. The robotic arm is coupled to the treatment probe and configured to align the elongate axis of the treatment probe with the elongate axis of the sheath and to advance the treatment probe into the sheath. The robotic arm coupled to the treatment probe is configured to align the axis of the treatment probe with the axis of the sheath prior to advancing the treatment probe into the sheath.

In some embodiments, the robotic arm comprises a sensor to determine an orientation of the treatment probe and the sensor comprises one or more of an accelerometer, a gyroscope, or an inertial measurement unit (IMU). Alternatively, or in combination, the arm coupled to sheath comprises a sensor to determine an orientation of the sheath. The sensor may comprise one or more of an accelerometer, a gyroscope, or an IMU.

In some embodiments, sheath comprises a proximal opening to receive the treatment probe and a distal opening and the treatment probe comprises a length sufficient to extend to at least the distal opening. In some embodiments, the treatment probe is dimensioned for the energy source to extend to at least the distal opening when the treatment probe has been advanced into the sheath.

In some embodiments, the energy source extends to at least the distal opening with a gap between an end portion of the robotic arm and the sheath.

Although reference is made to the coupling structure rotating the treatment probe, in some embodiments robotic arm 2630 is configured to rotate the treatment probe.

The processor can be coupled to one or more of the arm 2610, the arm 2630, or the arm 2720. In some embodiments, processor configured with instructions to advance the treatment probe into the sheath, which can facilitate the alignment of the treatment probe with the sheath. In some embodiments, the processor is configured to align the elongate axis of the treatment probe with the elongate axis of the sheath. In some embodiments, the processor is configured with instructions to receive an input indicating that the elongate axis of the treatment probe has been aligned with the elongate axis of the sheath and to advance the treatment probe along the elongate axis of the treatment probe in response to the input. The input may comprise a user input, or the input may comprise an input from sensor data. In some embodiments, the arm coupled to the stiff sheath comprises a sensor operatively coupled to the processor to determine an orientation of the sheath, and the processor is configured with instructions to orient the treatment probe with the sheath in response to the orientation of the stiff sheath measured with the sensor. In some embodiments, the robotic arm comprises a sensor to determine an orientation of the treatment probe. Alternatively, or in combination, the orientation of the treatment probe can be determined from the joint states of the robotic arm. In some embodiments, the orientation of the sheath is determined from joint states of the arm coupled to the stiff sheath.

Figure 14A:
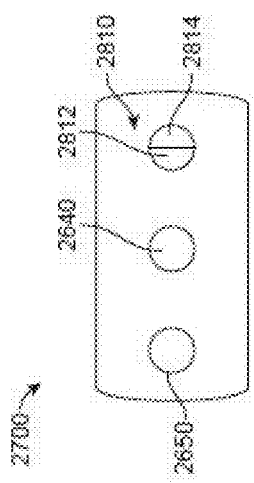
FIG. 14A illustrates a coupling to couple a robotic arm to a treatment probe.

FIG. 14A illustrates a coupling 2700 to couple a robotic arm 2630 to a treatment probe 2640. In some embodiments, the coupling 2700 is configured to couple the treatment probe 2740, the endoscope 2650, an irrigation lumen 2812 and an aspiration lumen 2814 to the robotic arm. Each of these lumens may be defined by an elongate tube defining the lumen. In some embodiments, the irrigation lumen and the aspiration lumen comprise lumens of a dual lumen tube such as a catheter. Alternatively, the irrigation lumen and the aspiration lumen may comprise separate catheters.

Figure 14B:
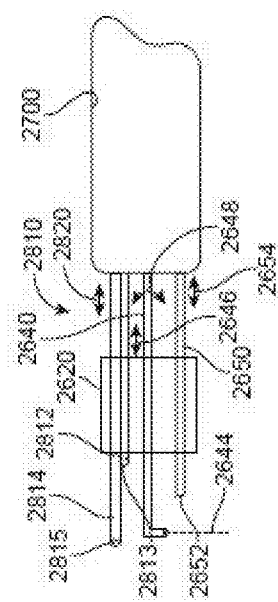
FIG. 14B illustrates movements of the treatment probe, the endoscope, the irrigation lumen and the aspiration lumen provided by the coupling as in FIG. 14A.

FIG. 14B illustrates movements of the treatment probe 2640, the endoscope 2650, the irrigation lumen 2812 and the aspiration lumen 2814 provided by the coupling as in FIG. 28A. The irrigation lumen 2812 extends to an opening 2813 to release an irrigation fluid. The aspiration lumen 2814 extends to an opening 2814 to receive resection products. The sheath 2620 is sized to receive these lumens and the corresponding structures defining the lumens, e.g. tubes. The sheath 2620 is sized to receive the treatment probe. In some embodiments, the sheath 2620 is sized to receive the endoscope 2650.

The coupling 2700 can be configured in many ways to move one or more of the treatment probe, the endoscope, the irrigation lumen or the aspiration lumen. In some embodiments, the coupling connects to the robotic arm 2630 and the robot arm provides motion to the treatment probe. For example, the robotic arm can be configured to rotate the treatment probe. Alternatively, or in combination, the robotic arm can be configured to rotate and translate the treatment arm.

In some embodiments, the coupling 2700 is configured to rotate the treatment probe. For example, the coupling can be configured to rotate 2648 the treatment probe. The robotic arm can be configured to translate 2646 the treatment probe while the coupling 2700 rotates the treatment probe. In some embodiments, the endoscope 2750 is configured to translate 2654 with the treatment probe. In some embodiments, the irrigation lumen and the aspiration lumen are configured to translate with the treatment probe.

In some embodiments, the coupling 2700 is configured to provide independent translational movement to the treatment probe and one or more of the endoscope, the irrigation lumen, or the aspiration lumen. In some embodiments, the coupling is configured to provide independent translation movement to the treatment probe, the endoscope, and one or more of the irrigation probe or the aspiration probe.

Figure 15:
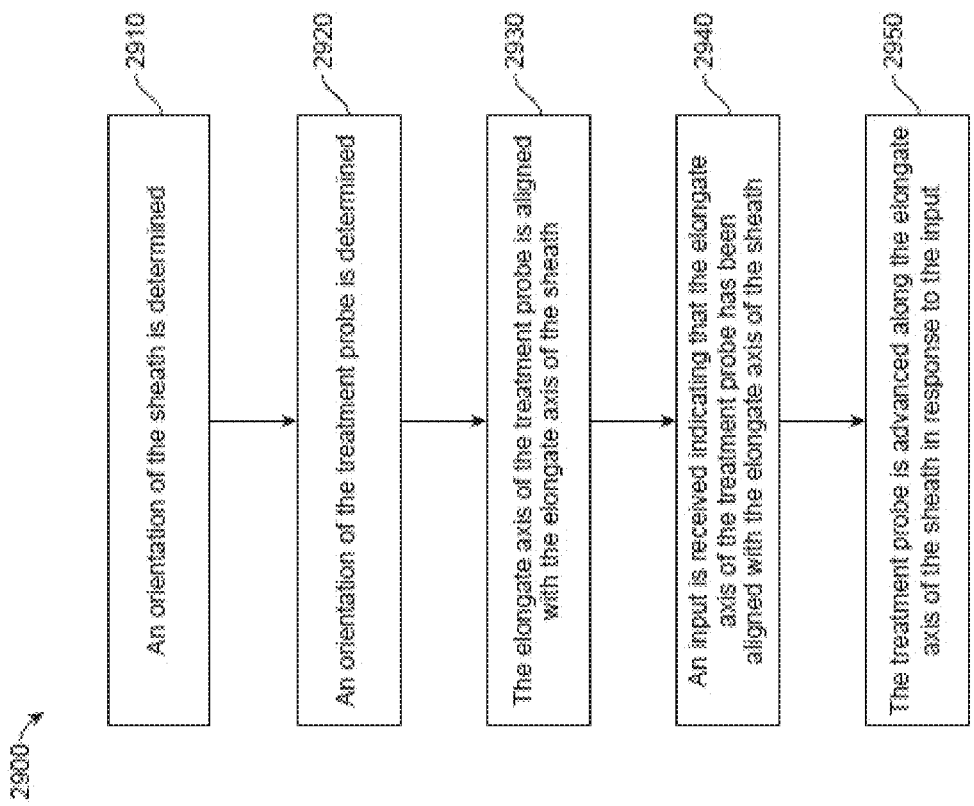
FIG. 15 illustrates a method of treatment, in accordance with some embodiments.

FIG. 15 illustrates a method 2900 of treatment, in accordance with some embodiments.

At a step 2910, an orientation of the sheath is determined. The orientation of the sheath can be determined from one or more sensors coupled to the sheath, such as an orientation sensor on the arm coupled to the sheath or from the joint states of the arm coupled to the sheath.

At a step 2920, an orientation of the treatment probe is determined. The orientation of the treatment probe can be determined from one or more sensors coupled to the treatment probe, such as an orientation sensor on the arm coupled to the treatment probe or from the joint states of the arm coupled to the treatment probe.

At a step 2930, the elongate axis of the treatment probe is aligned with the elongate axis of the sheath. This alignment can be performed manually. Alternatively, the processor can be configured with instructions to align the elongate axis of the treatment probe with the elongate axis of the sheath.

At a step 2940, an input is received indicating that the elongate axis of the treatment probe has been aligned with the elongate axis of the sheath. This input may comprise a user input based on visualization or an input from sensor data, or a combination thereof.

At a step 2950, the treatment probe is advanced along the elongate axis of the sheath in response to the input.

Figure 16:
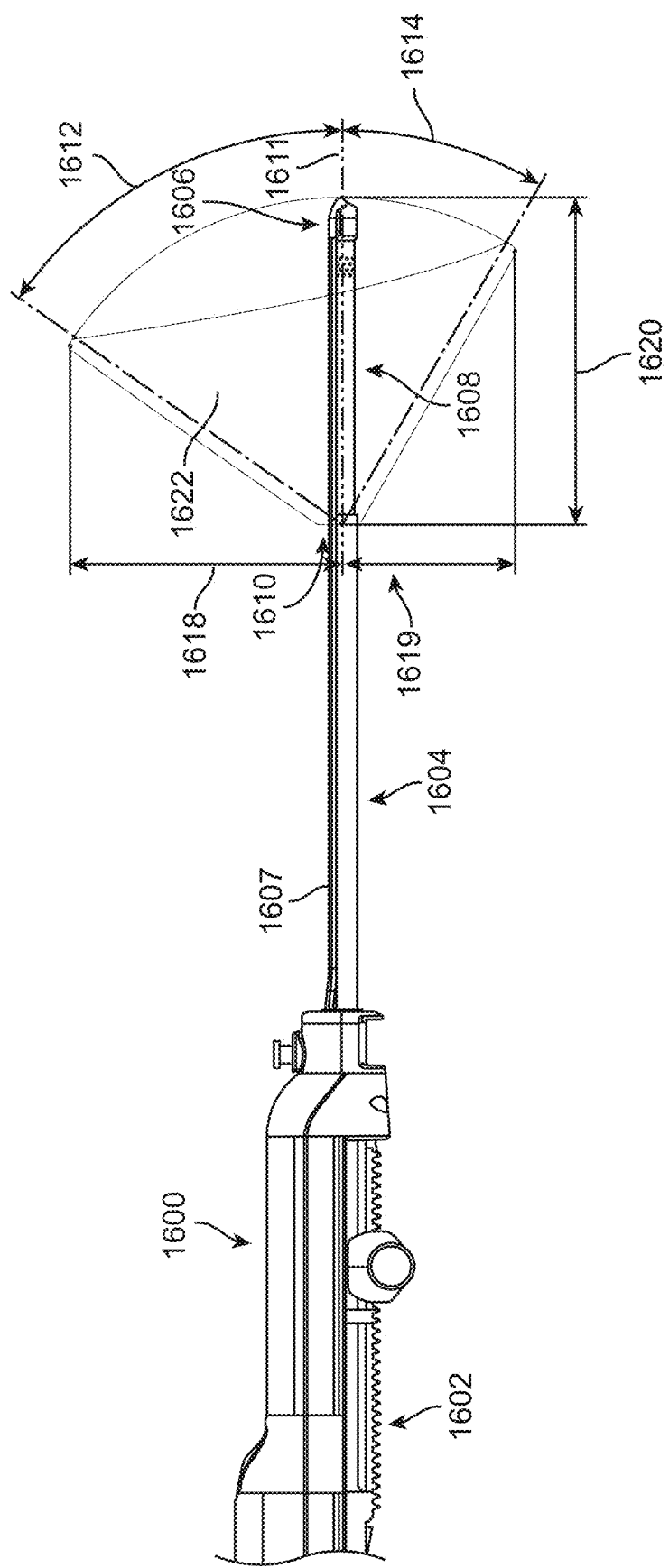
FIG. 16 illustrates a side view of a handpiece or treatment probe and shows an example range of motion (ROM) about a ROM origin point of the probe for the distal end of the probe from that perspective, in accordance with some embodiments.

FIG. 16 illustrates a side view of a handpiece or treatment probe 1600 and shows an example range of motion (ROM) 1622 about a ROM origin or pivot point 1610 of the probe for the distal end of the probe from that perspective, in accordance with some embodiments. As shown in the figure, a treatment probe 1600 may comprise a handle 1602 and a wand or extension 1604 extending from the handle to a distal end 1606 of the probe. The wand or extension may comprise two segments (identified as "segment 1" 1607 and "segment 2" 1608 in the figure), with segment 1 extending from the end of the handle to a point or location about which the distal end may rotate or otherwise move (referred to as an origin or pivot point 1610 herein), and segment 2 extending from the pivot point to the distal end of the probe.

As shown, a superior angle 1612 may be defined between the axis of the probe 1611 and an upper boundary of the probe range of motion 1622. In some embodiments, the superior angle may vary between 50 and 60 degrees, for example 55 degrees. An inferior angle 1614 may be defined between the axis 1611 of the probe and a lower boundary of the probe range of motion 1622. In some embodiments, the inferior angle may vary between 20 and 40 degrees, for example 30 degrees. The figure also indicates distances between the axis 1611 of the probe and the boundaries of the range of motion 1622. In some embodiments, the distance 1618 between the probe axis 1611 and the upper boundary of the range of motion 1622 may vary between 80 and 100 mm, for example 87 mm. In some embodiments, the distance 1619 between the probe axis 1611 and the lower boundary of the range of motion 1622 may vary between 50 and 60 mm, for example 55 mm. In some embodiments, the distance 1620 between the pivot point 1610 and the distal end 1606 of the probe may vary between 90 and 120 mm, for example 105 mm.

The approximately conical section 1622 shown in the figure (representing the Possible Range of Motion) is the envelope or region within which the distal end of the probe may move about the origin (pivot) point prior to application of any further constraints or limitations. Note that in this example, the range of motion or envelope within which the distal end may move when viewed from this perspective is not symmetrical.

Figure 17:
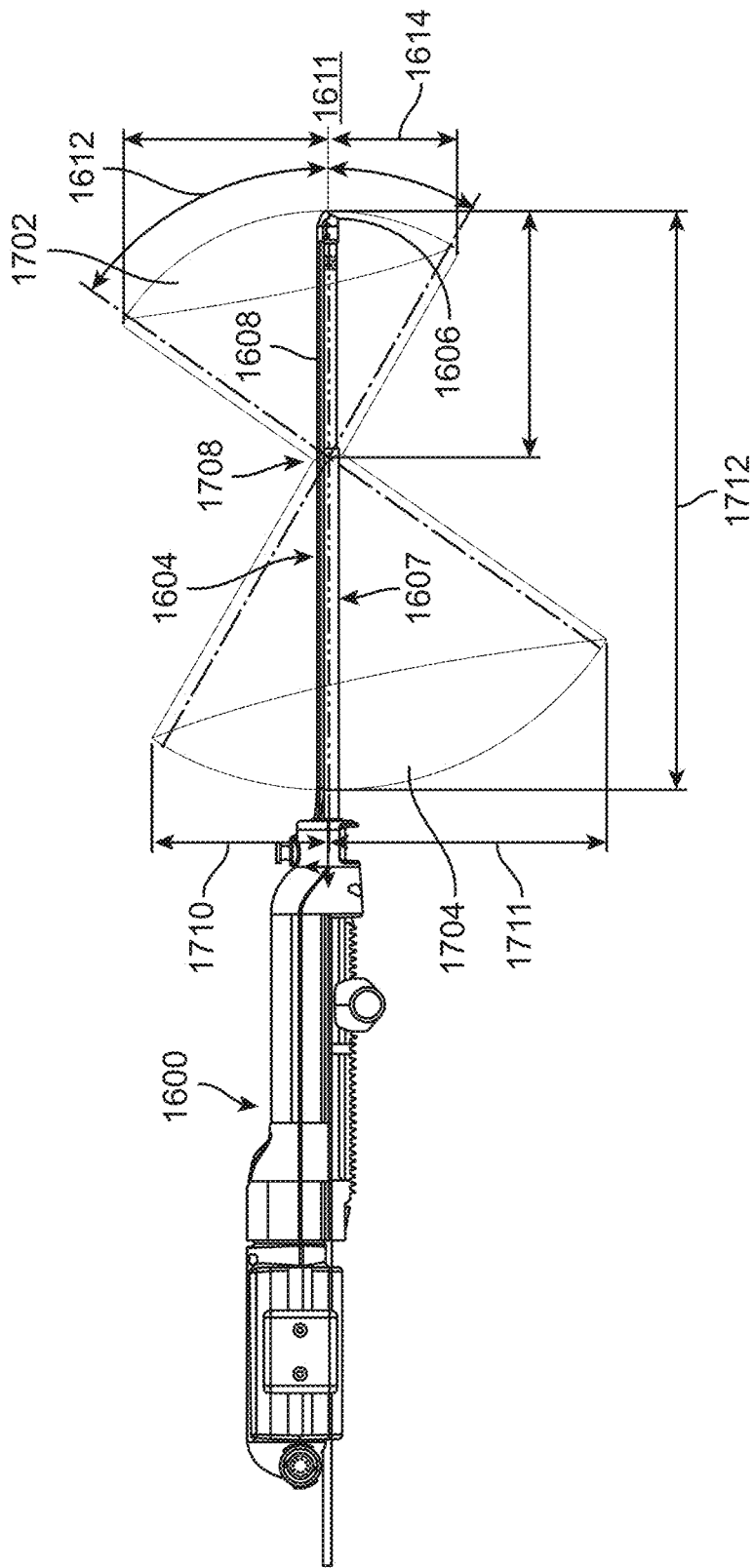
FIG. 17 illustrates the treatment probe of FIG. 16 and shows an example of a possible range of motion (ROM) for the distal end of the probe, in accordance with some embodiments. The figure also illustrates a possible range of motion for the probe about a pivot point representing the location on the probe wand beyond which the probe is inserted into a patient's body.

FIG. 17 illustrates the treatment probe 1600 of FIG. 16 and shows an example of a possible range of motion (ROM) 1702 for the distal end 1606 of the probe, in accordance with some embodiments. The figure also illustrates a possible range of motion 1704 for the probe under the control of a robotic arm about the pivot point 1708, where this point represents the location on the probe wand or extension 1604 beyond which the probe is inserted into a patient's body. The figure indicates distances between the axis of the probe 1611 and the boundaries of the range of motion for the probe under control of the robotic arm 1704. In some embodiments, the distance 1710 between the probe axis 1611 and the upper boundary of the range of motion 1704 may be vary between 70 and 80 mm, for example 75 mm. In some embodiments, the distance 1711 between the probe axis 1611 and the lower boundary of the range of motion 1704 may vary between 110 and 130 mm, for example 119 mm. In some embodiments, the distance 1712 between the outer edge of the range of motion under robotic control 1704 and the outer edge of the range of motion of the distal end 1702 may vary between 225 mm and 275 mm, for example 247 mm.

As examples, repositioning or other factors that may impact the (safe) range of motion of the distal end of the treatment probe may be due to one or more of (a) the specific treatment area involved, (b) the patient's anatomy and differences in tissue and organ sizes and shapes between patients, (c) the patient's physical size, (d) the patient's position or orientation for the treatment, or (e) the patient's health condition or prior medical history. These possible reasons for a change in the range of motion of the treatment probe emphasize the importance of preventing collisions or harm to the patient tissue and organs using the approaches described herein.

Figure 18:
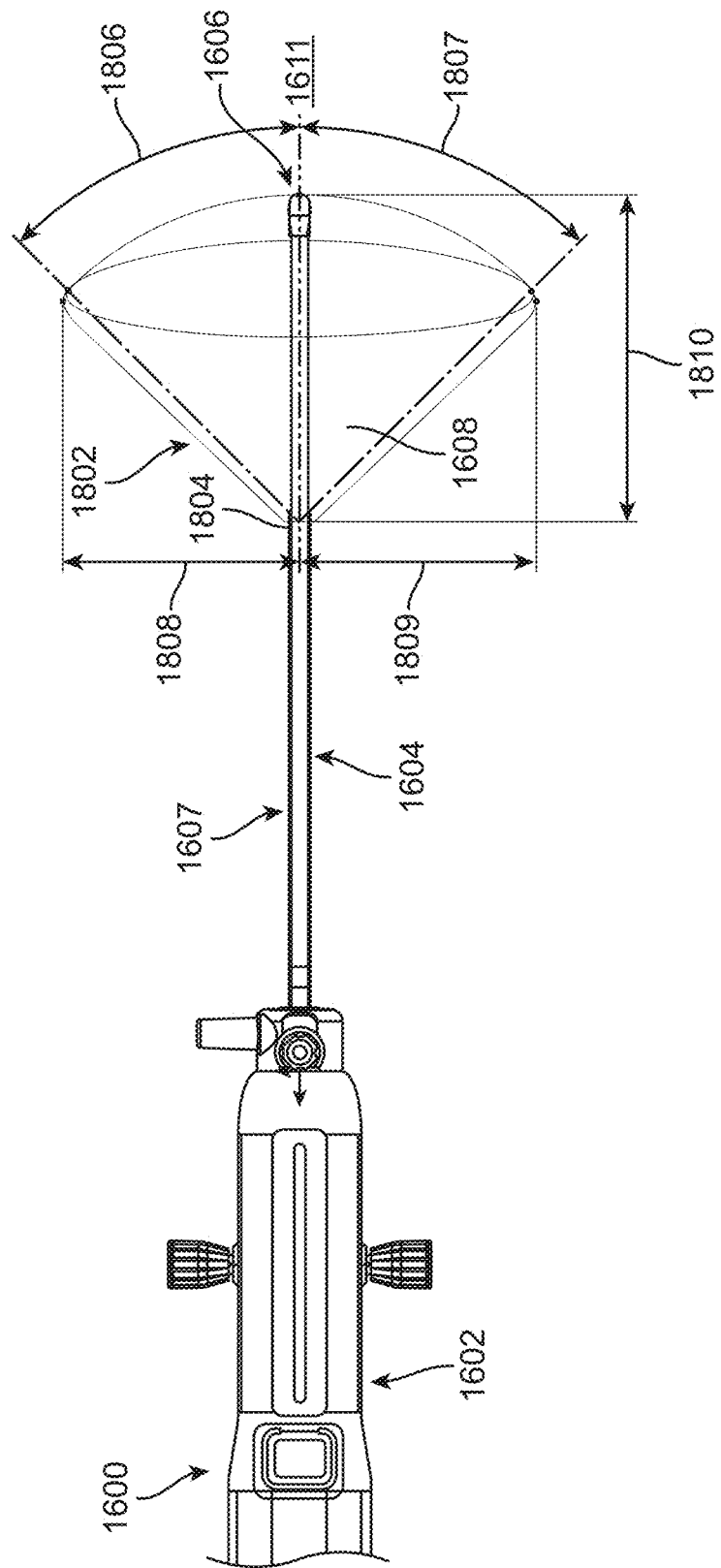
FIG. 18 illustrates a top view of the handpiece or treatment probe of FIG. 16 and shows an example range of motion about a range of motion origin point of the probe for the distal end of the probe from that perspective, in accordance with some embodiments.

FIG. 18 illustrates a top view of the handpiece or treatment probe 1600 of FIG. 16 and shows an example range of motion 1802 about a range of motion origin (pivot) point 1804 of the probe for the distal end 1606 of the probe from that perspective, in accordance with some embodiments.

As shown, a first side angle 1806 may be defined between the axis 1611 of the probe and an upper boundary of the probe range of motion 1802. In some embodiments, the first side angle may vary between 40 and 50 degrees, for example 45 degrees. A second side angle 1807 may be defined between the axis 1611 of the probe and a lower boundary of the probe range of motion 1802. In some embodiments, the second side angle may vary between 40 and 50 degrees, for example 45 degrees. The figure also indicates distances between the axis of the probe and the boundaries of the range of motion. In some embodiments, the distance 1808 between the probe axis 1611 and the upper boundary of the range of motion 1802 may be vary between 70 and 80 mm, for example 76 mm. In some embodiments, the distance 1809 between the probe axis 1611 and the lower boundary of the range of motion 1802 may vary between 70 and 80 mm, for example 76 mm. In some embodiments, the distance 1810 between the pivot point 1804 and the distal end of the probe 1606 may vary between 90 and 120 mm, for example 105 mm. The approximately conical section 1802 shown in the figure (representing the Possible Range of Motion) is the envelope or region within which the distal end 1606 of the probe may move about the origin (pivot) point 1804 prior to application of any further constraints or limitations. Note that in this example, the range of motion or envelope within which the distal end may move when viewed from this perspective is symmetrical.

Figure 19:
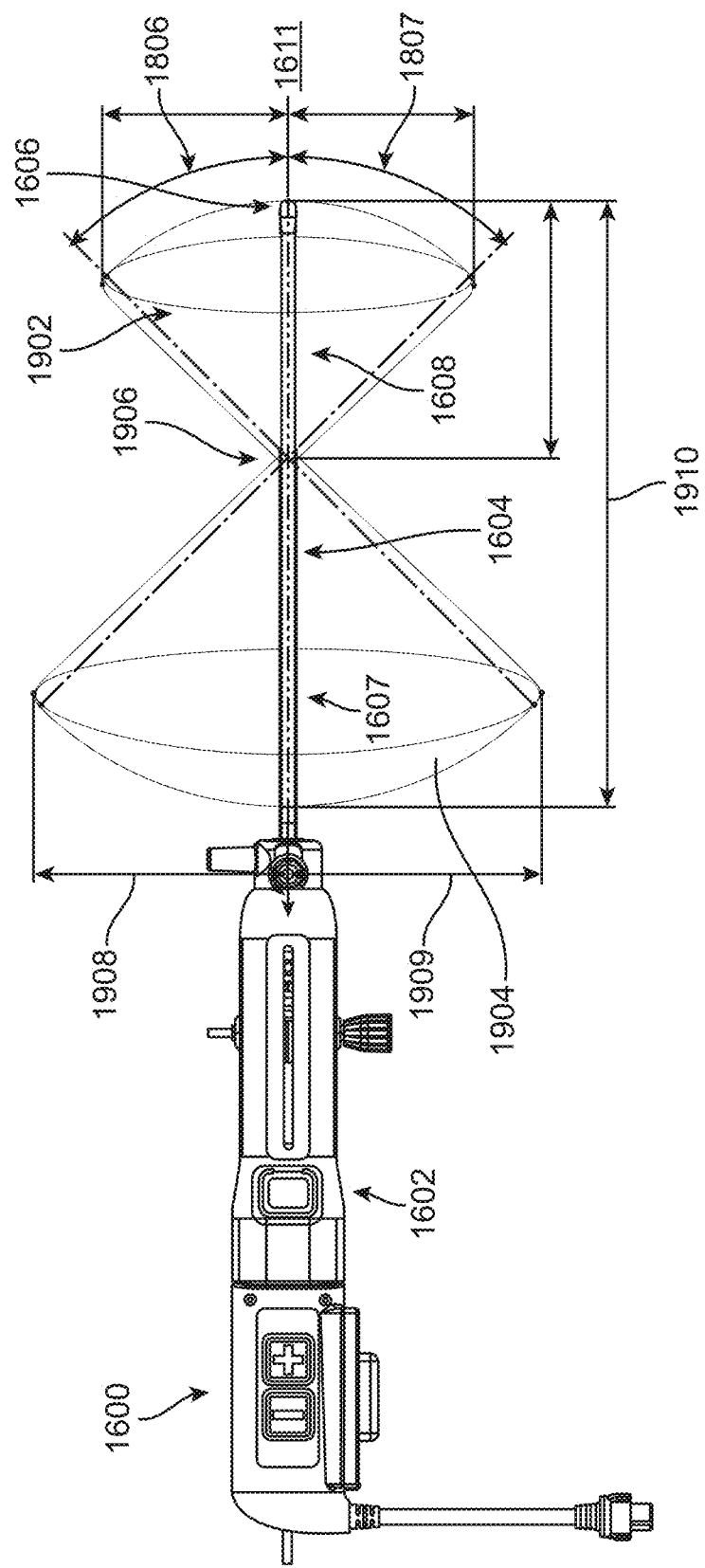
FIG. 19 illustrates the treatment probe of FIG. 18 and shows an example of a possible range of motion (ROM) for the distal end of the probe, in accordance with some embodiments. The figure also illustrates a possible range of motion for the probe about a pivot point representing the location on the probe wand beyond which the probe is inserted into a patient's body.

FIG. 19 illustrates the treatment probe 1600 of FIG. 18 and shows an example of a possible range of motion (ROM) 1902 for the distal end 1606 of the probe, in accordance with some embodiments. The figure also illustrates a possible range of motion 1904 for the probe under the control of a robotic arm about the pivot point 1906, where the pivot point represents the location on the probe wand or extension 1604 beyond which the probe is inserted into a patient's body. The figure indicates distances between the axis of the probe 1611 and the boundaries of the range of motion 1904 for the probe under control of the robotic arm. In some embodiments, the distance 1908 between the probe axis 1611 and the upper boundary of the range of motion 1904 may be vary between 90 and 110 mm, for example 104 mm. In some embodiments, the distance 1909 between the probe axis 1611 and the lower boundary of the range of motion 1904 may vary between 90 and 110 mm, for example 104 mm. In some embodiments, the distance 1910 between the outer edge of the range of motion under robotic control 1904 and the outer edge of the range of motion of the distal end 1902 may vary between 225 mm and 275 mm, for example 247 mm.

Figure 20:
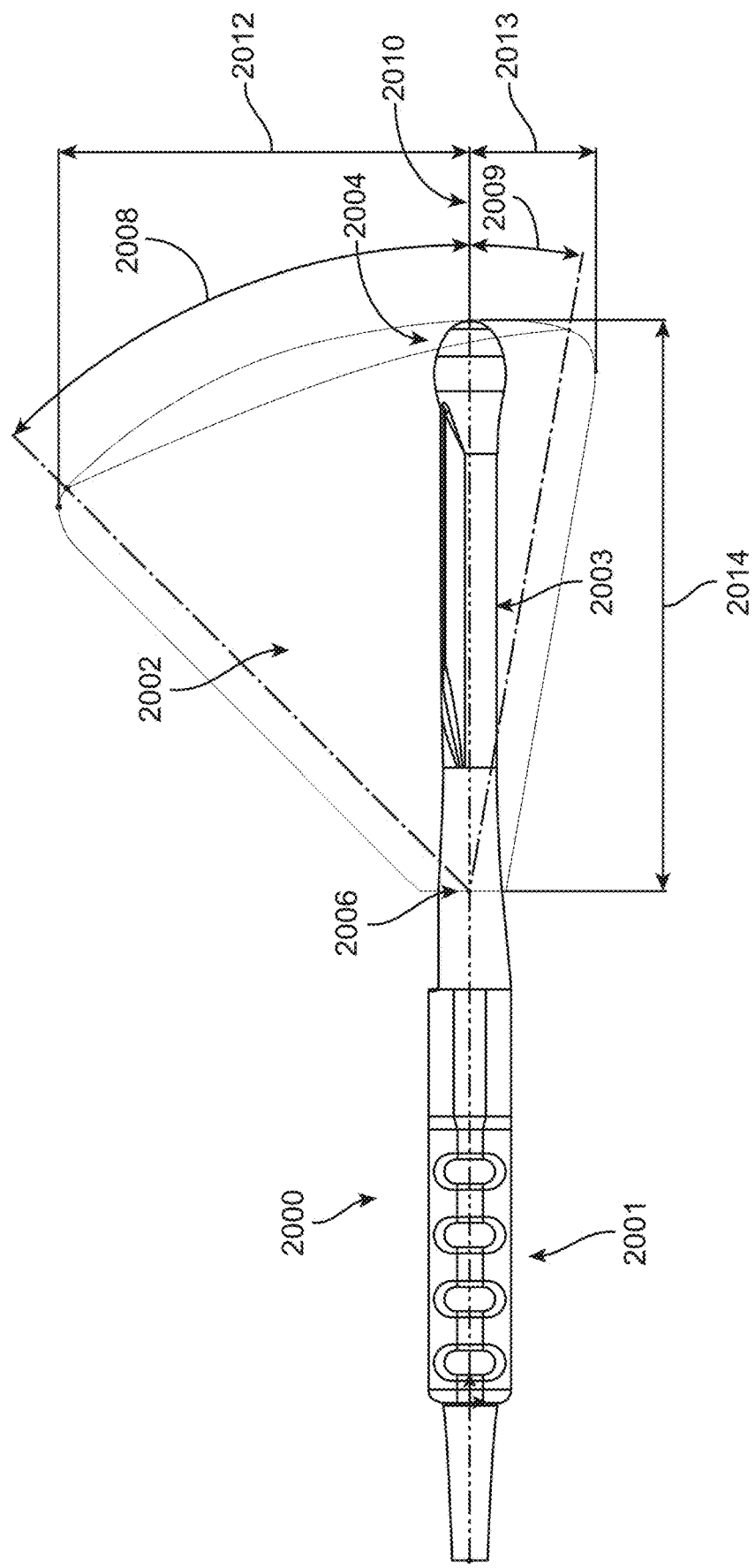
FIG. 20 illustrates a side view of an imaging probe and an example of a range of motion for the distal end of the probe about a pivot point from that perspective, in accordance with some embodiments.

FIG. 20 illustrates a side view of an imaging probe 2000 and an example of a range of motion 2002 for the distal end 2004 of the probe about a pivot point 2006 from that perspective, in accordance with some embodiments. As shown in the figure, an imaging probe 2000 may comprise a handle 2001 and a wand or extension 2003 extending from the handle to the distal end of the probe. The wand or extension 2003 may comprise a segment extending from a pivot point 2006 to the distal end 2004 of the probe.

As shown, a superior angle 2008 may be defined between the axis 2010 of the probe and an upper boundary of the probe range of motion 2002. In some embodiments, the superior angle may vary between 40 and 50 degrees, for example 45 degrees. An inferior angle 2009 may be defined between the axis 2010 of the probe and a lower boundary of the probe range of motion 2002. In some embodiments, the inferior angle may vary between 5 and 15 degrees, for example 10 degrees. The figure also indicates distances between the axis of the probe 2010 and the boundaries of the range of motion 2002. In some embodiments, the distance 2012 between the probe axis 2010 and the upper boundary of the range of motion 2002 may be vary between 110 and 150 mm, for example 130 mm. In some embodiments, the distance 2013 between the probe axis 2010 and the lower boundary of the range of motion 2002 may vary between 30 and 50 mm, for example 40 mm. In some embodiments, the distance 2014 between the pivot point 2006 and the distal end 2004 of the probe may vary between 150 and 200 mm, for example 180 mm. Note that as viewed from this perspective the range of motion or envelope within which the distal end of the probe may move is not symmetrical.

Figure 21:
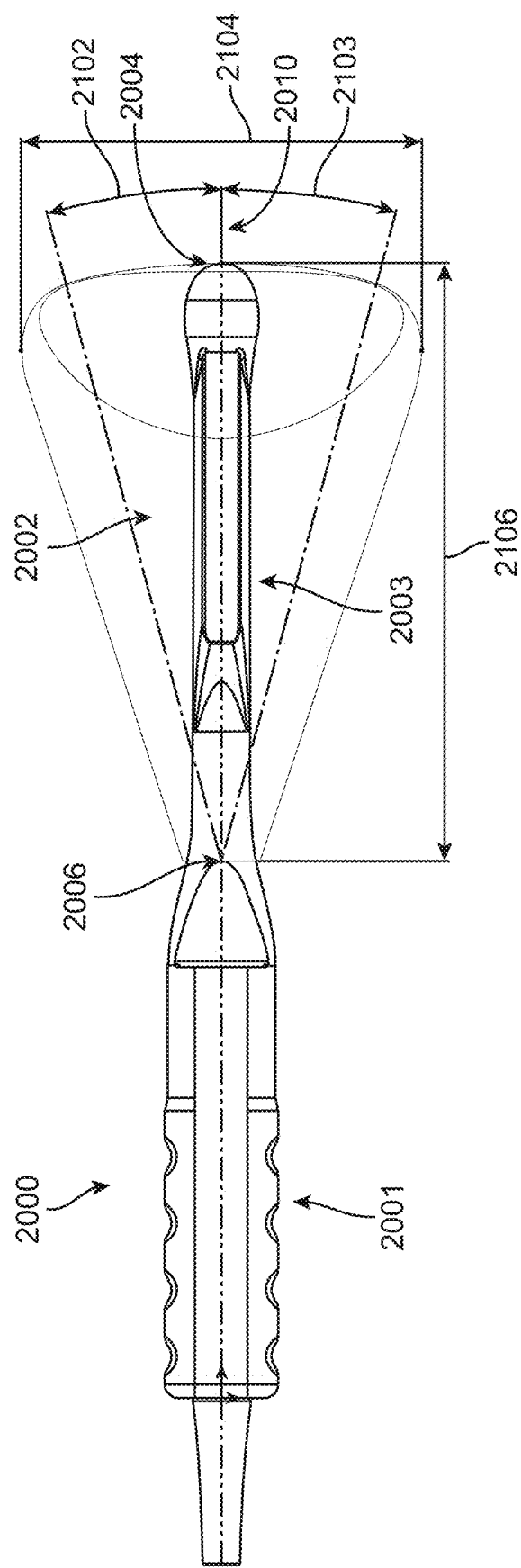
FIG. 21 illustrates a top view of the imaging probe of FIG. 20 and an example of a range of motion for the distal end of the probe about a pivot point from that perspective, in accordance with some embodiments.

FIG. 21 illustrates a top view of the imaging probe 2000 of FIG. 20 and an example of a range of motion 2002 for the distal end 2004 of the probe about a pivot point 2006 from that perspective, in accordance with some embodiments. As shown, a first side angle 2102 may be defined between the axis 2010 of the probe and an upper boundary of the probe range of motion 2002. In some embodiments, the first side angle may vary between 10 and 20 degrees, for example 15 degrees. A second side angle 2103 may be defined between the axis 2010 of the probe and a lower boundary of the probe range of motion 2002. In some embodiments, the second side angle may vary between 10 and 20 degrees, for example 15 degrees. The figure also indicates distances between the axis of the probe 2010 and the boundaries of the range of motion 2002. In some embodiments, the distance 2104 between the upper boundary of the range of motion and the lower boundary may be vary between 100 and 140 mm, for example 120 mm. In some embodiments, the distance 2106 between the pivot point 2006 and the distal end 2004 of the probe may vary between 150 and 200 mm, for example 180 mm. Note that as viewed from this perspective the range of motion or envelope within which the distal end of the probe may move is symmetrical.

Figure 22:
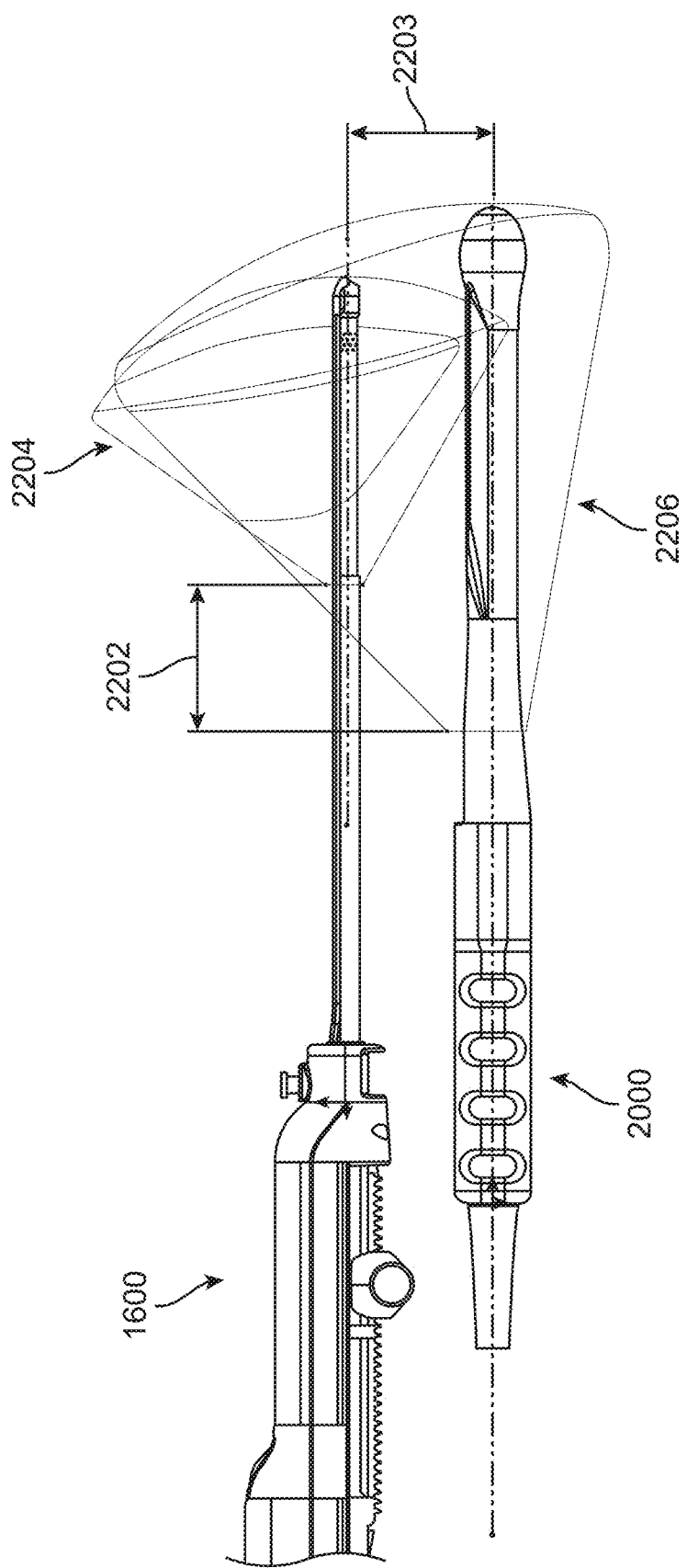
FIG. 22 illustrates a side view of a treatment probe and an imaging probe and shows the respective ranges of motion of the distal end of each probe overlaid with each other from that perspective, in accordance with some embodiments.

FIG. 22 illustrates a side view of a treatment probe 1600 and an imaging probe 2000 and shows the respective ranges of motion of the distal end of each probe overlaid with each other from that perspective, in accordance with some embodiments. In the figure, the probes are separate but colinear or substantially parallel to each other with the pivot point of the treatment probe positioned in front of (offset from) the pivot point of the imaging probe, as indicated by the distance represented by the separation of the pivot points of the probes 2202.

The longitudinal and lateral separation between the probes may vary or be varied as needed for a specific patient anatomy and treatment. For example, in some embodiments, the longitudinal separation 2202 of the pivot points (or fulcrums) of the two probes may vary between 25 and 75 mm, for example 50 mm. The lateral separation 2203 of the two substantially parallel probes may vary between 25 and 75 mm, for example 50 mm. As shown in the figure, the possible range of motion for the treatment probe 2204 is of a different shape and dimensions than that of the imaging probe 2206, as viewed from this perspective. The longitudinal and/or lateral separation of the two probes may be set initially and then modified by a physician based on patient anatomy, the specific treatment being performed, a CT or MRI scan, a pre-programmed profile for a treatment or patient, etc.

The relative positioning of the distal ends of the two probes shown in the figure is an example of how the two probes may be positioned when used for a treatment. This example of the relative positioning may result from a physician inserting each probe into a patient and then repositioning one or both probes prior to a treatment. This example of the relative positioning may also result from a robotic arm moving one or both probes after the probes are inserted into a patient. Note that in some embodiments, the system may be used to calibrate or pre-program the movements of the robotic arms to ensure that the two probes don't collide or come within a specified distance of each other (even though their range of motion (ROM) may intersect or overlap).

Figure 23:
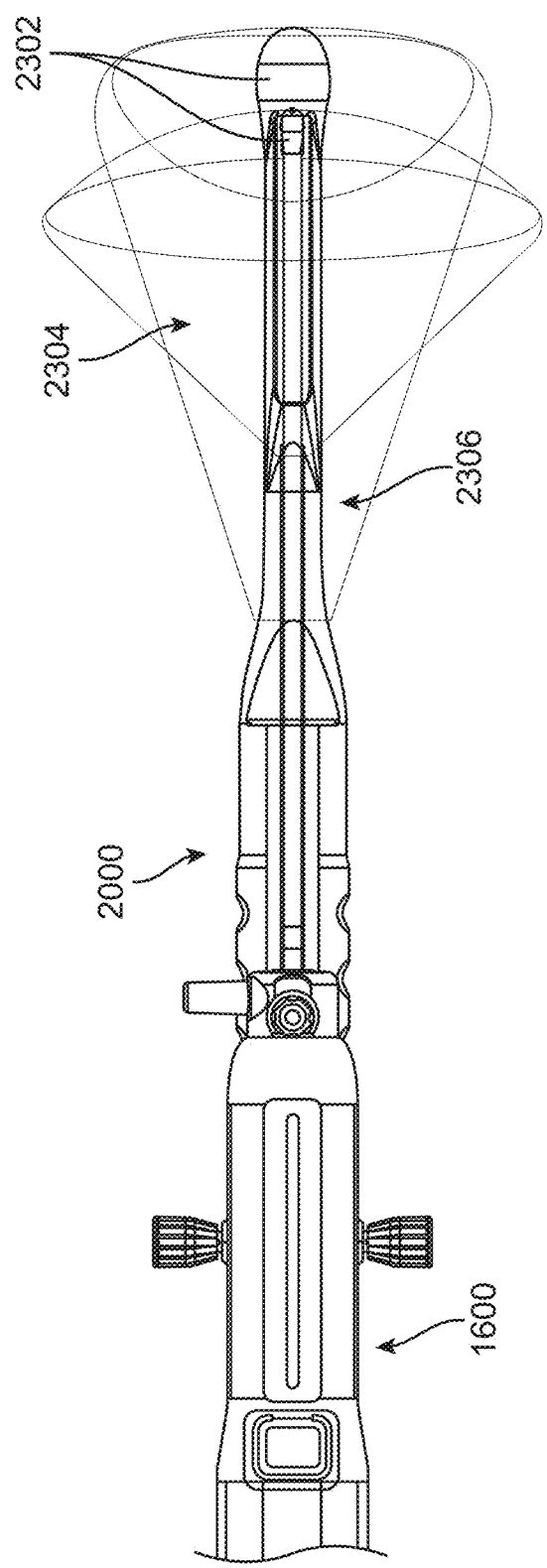
FIG. 23 illustrates a top view of the treatment probe and imaging probe of FIG. 22 and shows the respective ranges of motion of the distal end of each probe overlaid with each other from that perspective, in accordance with some embodiments.

FIG. 23 illustrates a top view of the treatment probe 1600 and imaging probe 2000 of FIG. 22 and shows the respective ranges of motion of the distal end of each probe overlaid with each other from that perspective, in accordance with some embodiments. As with FIG. 22, in FIG. 23 the probes are separate but colinear or parallel to each other with the pivot point of the treatment probe positioned in front of (offset from) the pivot point of the imaging probe. Note that in the embodiment shown, the distal ends 2302 of the two probes are also offset. Note also that in the figure, the imaging probe is underneath and partially obscured by the treatment probe. As shown in the figure, the possible range of motion for the treatment probe 2304 is of a different shape and dimensions than that of the imaging probe 2306, as viewed from this perspective.

As is apparent from the figures, in some embodiments each of the probes has a respective possible range of motion. This possible range of motion represents the maximum envelope or boundary region within which the distal end of the probe can move based on the probe's construction and operation.

As mentioned, this possible range of motion may be constrained or limited to prevent collision between the probes and/or the robotic arms that are used to move the probes. The constraint or limitation may be the result of a training or teaching process as described herein, where a physician may manipulate the probes and their respective distal ends to define an allowable range of motion. The training or teaching process may be performed with the probes outside of a patient and/or inside a patient. Further, images of the treatment probe and/or the interior of the patient's body may be used to further constrain or restrict the allowable motion of the probes or robotic arms to prevent collisions or harm to a patient.

Figure 24:
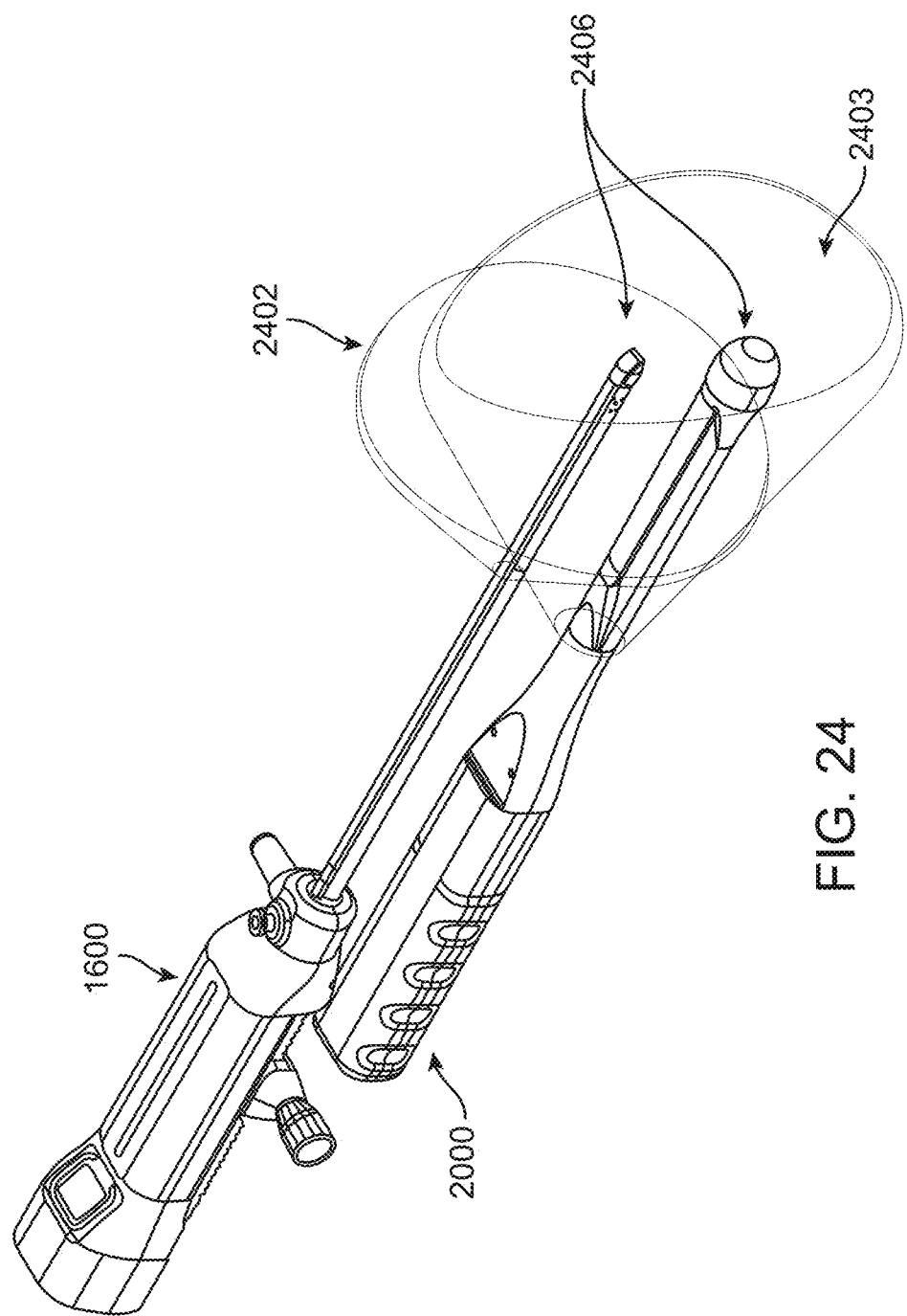
FIG. 24 illustrates an isometric view of a treatment probe and an imaging probe and shows the respective ranges of motion of the distal ends of the probes overlaid with each other from that perspective, in accordance with some embodiments.

FIG. 24 illustrates an isometric view of a treatment probe 1600 and an imaging probe 2000 and shows the respective ranges of motion 2402 (treatment probe) and 2403 (imaging probe) of the distal ends 2406 of the probes overlaid with each other from that perspective, in accordance with some embodiments. In the figure, the probes are separate but colinear or parallel to each other with the distal end of the imaging probe aligned with the distal end of the treatment probe as indicated by the alignment of the distal ends 2406. The figure shows the asymmetrical envelope of motion possible for the distal end of the imaging probe from that perspective.

Figure 25A:
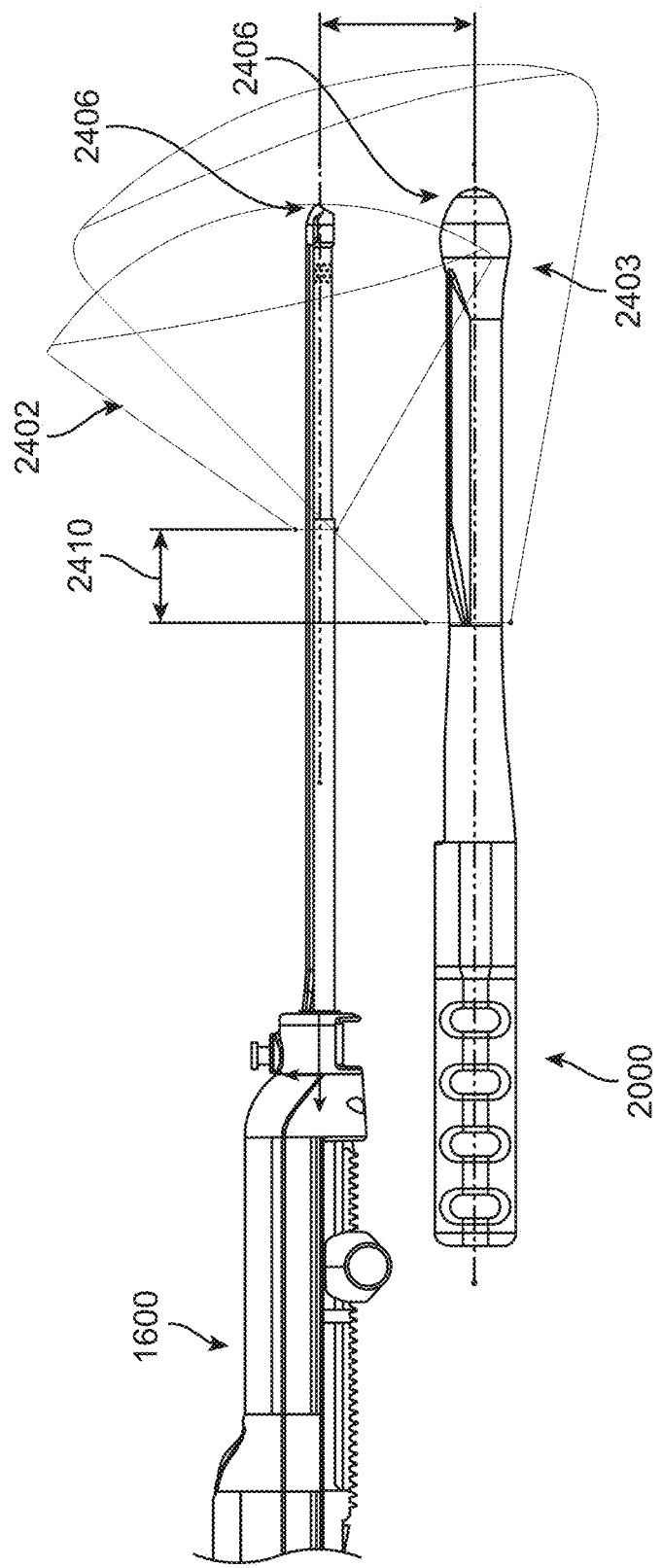
FIG. 25A illustrates a side view of the treatment probe and imaging probe of FIG. 24 and shows the respective ranges of motion of the distal ends of the probes overlaid with each other from that perspective, in accordance with some embodiments.

FIG. 25A illustrates a side view of the treatment probe 1600 and imaging probe 2000 of FIG. 24 and shows the respective ranges of motion 2402, 2403 of the distal ends 2406 of the probes 1600, 2000, respectively, overlaid with each other from that perspective, in accordance with some embodiments. Note that in comparison with FIG. 22, the longitudinal distance 2410 between the pivot points (or fulcrums) on the respective probes is reduced as the distal ends are aligned as indicated by the positions of distal ends 2406. In this embodiment, the longitudinal separation 2410 between the two pivot points or fulcrums is for example 50 mm or less. This change in relative positioning of the distal ends of the two probes in comparison to FIG. 22 impacts the way in which the respective ranges of motion for the probes overlap. This situation could arise in a treatment of a patient for whom the imaging probe could not be inserted as far as in the example shown in FIG. 22 and/or during movement of the imaging probe in relation to the treatment probe during treatment.

Figure 25B:
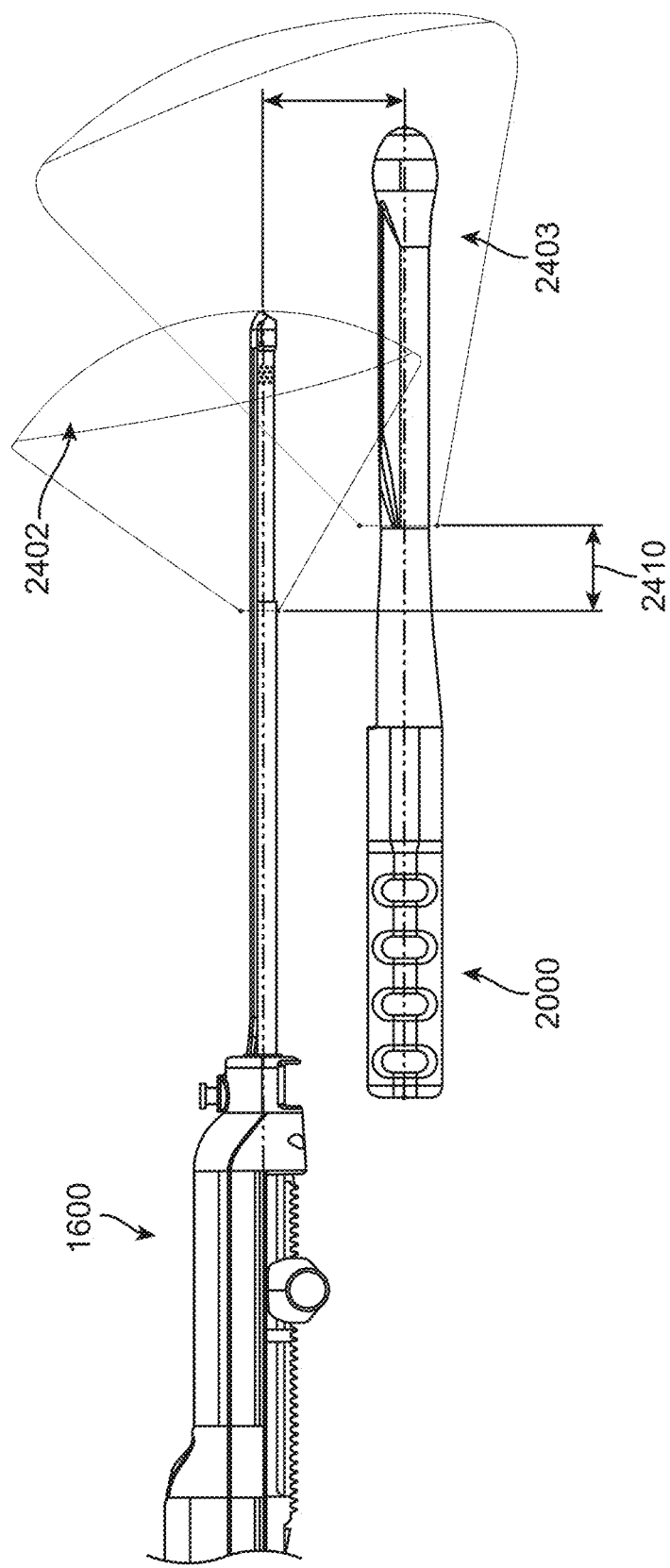
FIG. 25B illustrates a side view of the treatment probe and imaging probe of FIG. 24 and shows the respective ranges of motion of the distal ends of the probes overlaid with each other from that perspective, in accordance with some embodiments. Note that in this figure, the imaging probe is advanced horizontally or longitudinally with respect to the treatment probe in comparison to FIG. 25A.

FIG. 25B illustrates a side view of the treatment probe 1600 and imaging probe 2000 of FIG. 24 and shows the respective ranges of motion 2402, 2403 of the distal ends of the probes 1600, 2000, respectively, overlaid with each other from that perspective, in accordance with some embodiments. Note that in this figure, the imaging probe 2000 is advanced horizontally or longitudinally with respect to the treatment probe in comparison to FIG. 25A. As a result, the distal ends of the probe are not aligned, as in FIG. 25A. This type of change in relative positioning could result from a difference in patient anatomy, patient internal organs or tissue, or the treatment being performed. In this embodiment, the longitudinal separation 2410 between the two pivot points or fulcrums is for example 50 mm.

As described, depending upon one or more factors related to the treatment plan, treatment site, patient positioning, or the patient anatomy (including for example, patient size or health), one or both of the treatment or imaging probes may not be able to be inserted or moved in the same manner as for another patient or treatment. This will result in different positioning of the distal ends of the probes relative to each other, and therefore a different amount of overlap or orientation of the range of motion envelope(s) for the two probes. Hence, careful monitoring of the position, location, orientation and movement of each probe relative to the patient and to each other is important to avoid harm to the patient or to the probes due to collisions.

FIG. 26 illustrates a top view of the treatment probe 1600 and imaging probe 2000 of FIG. 25 and shows the respective ranges of motion 2402, 2403 overlaid with each other when the probes 1600, 2000, respectively, are separate but colinear or parallel to each other, in accordance with some embodiments. In the figure, the distal end of the imaging probe is aligned with the distal end of the treatment probe as indicated by positions of ends 2406. As seen from the figure, from this perspective or view the ranges of motion or envelopes of motion appear symmetrical.

As has been described, during a treatment each of the two probes is inserted into a patient. The imaging probe (or TRUS probe in some examples) is typically inserted into a patient's rectum or sphincter muscle, and typically up to the pubic bone. A physician or surgeon can move the imaging probe within the tissue regions but must be careful not to move the probe into or against bone with force, as that may cause harm to the patient. In some embodiments, a boundary or limit on the possible motion of the distal end of the probe may be obtained from studies of cadavers or other forms of research activities. This may be instead of, or in addition to a teaching or training session performed by a physician either prior to or after insertion of the probe into a patient.

The treatment probe or handpiece is typically inserted through the urethra for prostate treatments, and towards the pelvic notch in front of the pubis. This may present a starting point for further manipulation or repositioning of the probe.

Figure 27:
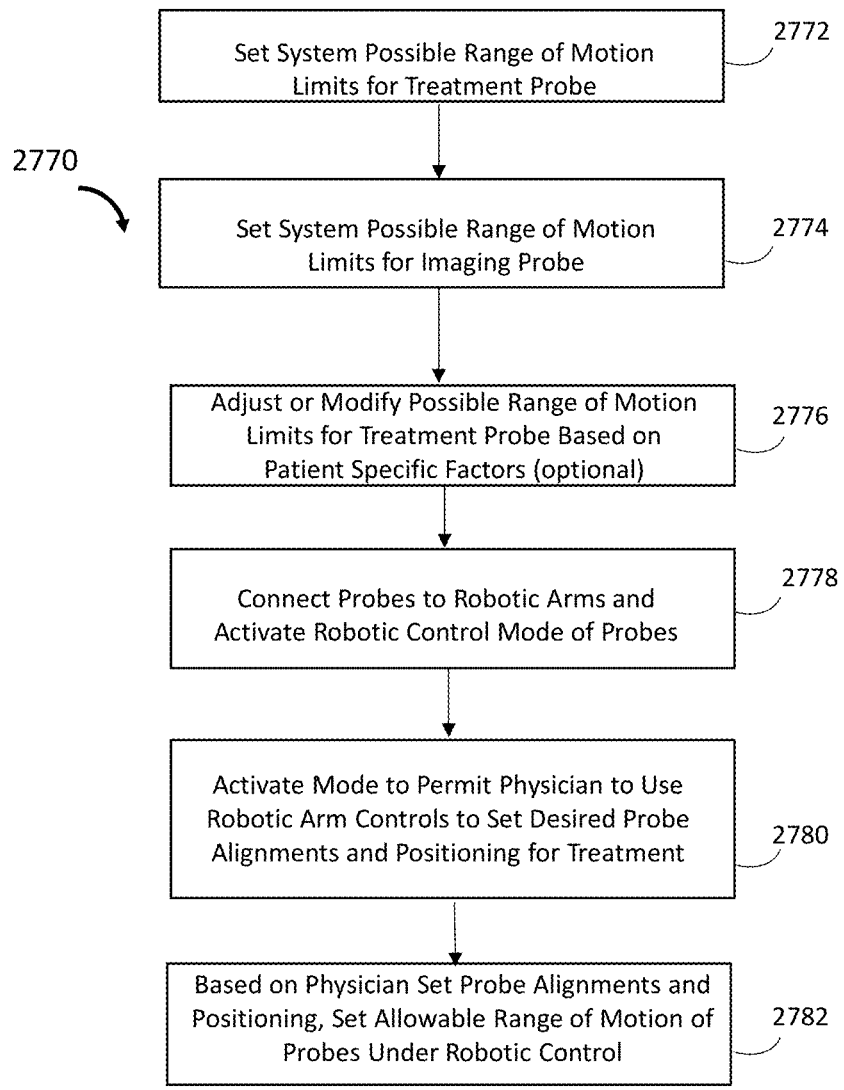
FIG. 27 is a flowchart or flow diagram illustrating a method, process, operation or function for setting a range of motion (ROM) for a probe used as part of a procedure to treat a patient, in accordance with some embodiments.

FIG. 27 is a flowchart or flow diagram illustrating a method, process, operation or function 2770 for setting a range of motion (ROM) for a probe used as part of a procedure to treat a patient, in accordance with some embodiments. With a step 2772, the possible range of motion limits are set for a treatment probe. As described herein, this may comprise providing the system with a mathematical or other description of the range of motion or envelope of motion of the probe about a pivot point.

With a step 2774, corresponding possible range of motion limits are set for an imaging probe. As described herein, this may comprise providing the system with a mathematical or other description of the range of motion or envelope of motion of the probe about a pivot point.

With a step 2776, the possible range of motion for either or both the treatment probe and imaging probe may be adjusted or modified based on patient specific factors or parameters. As described herein, this may involve consideration of patient anatomy, a patient scan and/or other relevant consideration. This is an optional step and may be performed by execution of a teaching or training session while the probes are external to a patient.

With a step 2778, the probe or probes are connected to the robotic arms of the system and activated to allow the robotic control of the location, positioning and orientation of the probe or probes.

With a step 2780, a physician may activate a mode to use the robotic arm controls to further define, constrain, or restrict the range of motion or positioning for one or both probes, and therefore define the allowable range of motion and desired probe positions for treatment. This may involve a teaching or training session or other form of setting the desired positions and range of motion for the probes.

With a step 2782, the system may set or fix one or more of the allowable range of motion for one or both probes, the positioning and alignment of each probe with respect to each other both longitudinally and laterally, and/or the positioning and alignment of each probe with respect to the treatment region.

Although the above steps show a method 2770 for setting a range of motion (ROM) for a probe used as part of a procedure to treat a patient in accordance with some embodiments, a person of ordinary skill in the art will recognize many variations based on the teachings described herein. For example, the steps may be completed in a different order. One or more steps may be added or omitted. Some of the steps may comprise sub-steps. Many of the steps may be repeated as often as necessary or desired.

In some sense, there are three possible areas or volumes of interest that may be used to define or set the allowable or desired range of motion, or place constraints on the initial possible range of motion (ROM) of one or both probes. A first volume is that of the possible and/or allowable range of motion of the two probes relative to each other. A second volume is that of the possible and/or allowable ROM of the imaging probe (inside the patient's rectum). A third volume is that of the possible and/or allowable ROM of the treatment probe (inside the patient's prostate/bladder). The first volume or region is to prevent collision of the devices with each other and a distance to maintain between the probes to protect against probe collision related tissue damage. The second volume or region is to establish a safe and desired tissue manipulation capability within the rectum, independent of the other probe's location. The third volume or region is to establish a safe and desired tissue manipulation capability within the bone structure, urethra, prostate, and bladder, independent of the other probe's location. Note that each region or volume may be established separately and together they function as a rule set that is taken into account when determining if an intersection of the regions or volumes may occur.

Note that although reference is made to defining, controlling and/or constraining the range of motion of the distal end or one or both of a treatment or an imaging probe, embodiments are also directed to defining, controlling and/or constraining the range of motion of an entire probe. This may include constraining or limiting the trajectory, motion, vector, alignment, orientation, or other form of positioning and/or motion of a probe. Such a constraint or limitation may be based on, or take into consideration, one or more of a probe's dimensions, a pivot point relative to a patient's anatomy, a relative alignment between a treatment probe and an imaging probe, or other relevant information or images.

In some embodiments and uses of the described system, a person will initially place or position a probe, the probe will be coupled to a robotic arm, and the robotic arm will then be used to move the probe. A range of motion, boundary of motion, or envelope of motion may be defined by data input to a computing system that is coupled to the robotic arm(s). The data may comprise measurements, parameter limits, threshold values, specific instructions, images, or other form of representing a constraint or limit on the possible movement of a probe.

The data may be generated during a training or teaching session conducted by a physician, such as by having the physician manipulate the probe to move it over the allowable range of motion. The allowable range of motion as defined by the physician may be modified by information or data regarding the patient that is stored in a database coupled to the computing device. The database may contain a scan, such as a CT or MRI, that provides more detailed information regarding a specific patient's anatomy and the treatment site. For purposes of ensuring safety to the patient, a tolerance amount may be used to adjust or modify the determined allowable range of motion.

As mentioned, a patient's anatomy may impact how a probe is positioned in the patient. For example, if a patient is obese or has more than an average amount of abdominal fatty tissue, then the length of the probe inserted into the patient and initial position of the probe inside the patient may be different than for a slenderer patient. Also, the relative location of the rectal pivot of the imaging probe and pivot of the treatment probe near the pelvic notch may vary, for example depending on weight.

In making fine adjustments to the location, position, or orientation of the treatment probe, the imaging probe may be used to obtain images of the distal end of the treatment probe. The imaging probe is typically several millimeters in width and for optimal ultrasound imaging, it is helpful to have contact between the probe and tissue. If sufficient contact is lacking, then an operator may need to slightly lift the probe slightly, for example. A patient's anatomy may be non-symmetrical and require movement of an imaging probe and/or treatment probe to one side or the other.

As mentioned, avoiding collisions between the probes, collisions between the robotic arms, or collisions between a probe and the tissue or organ of a patient are all important in preventing harm and successfully completing a treatment. As described herein, avoiding collisions by constraining or limiting the range of motion of a probe can be accomplished by several approaches.

A first is a purely manual approach, as is done conventionally. In this approach, a physician is responsible for carefully manipulating the probe or probes to avoid contact with each other or with the tissue or organs of the patient. The physician may rely on images from the imaging probe to determine the location of each probe inside the patient and to recognize tissue or other structures inside the patient.

A second approach is to set limits on the possible range of motion or define a boundary of a region or envelope in which the probe distal end may safely move. As described, in one example, a physician may demonstrate to a computing system a range of allowable motion of a probe. The computing system may determine from the demonstrated range of motion the parameters of allowed motion and these parameters may be translated into restrictions or limits on the commands or instructions that may be applied to the robotic arms and probes. Sensors on the arms or probes may assist in determining the location, position, or orientation of a robotic arm or probe.

A third approach combines the second approach with images from inside the patient. This approach may use image recognition or a previously obtained scan of the patient to identify tissue or organs inside the patient and combined with images of the treatment probe, may be used to provide information for controlling movement of the treatment probe. The imaging probe data can be used to determine how far apart the two probes are, for example. In one example, it may be desirable to maintain a minimum distance between the distal ends of the two probes, for example 2 mm.

In some embodiments, a mathematical model or representation of the possible ranges of motion of each probe may be generated and stored in a computing device. The possible range of motion or envelope of possible motion is typically represented by some form of symmetric or asymmetric conic section. Given the probe dimensions and the points on the probe corresponding to where the probe wands are inserted into the patient (e.g., the pivot points), a computing device can calculate and display the relative position, orientation and range of motion of the two probes inside the patient. This display can be modified by information from a patient scan and/or physician to generate a patient-specific display of the probes and their respective ranges of motion while inside the patient. This information may be used to prevent collisions or harm to the patient by generating an alert, preventing further movement, or other suitable mechanism when (or if) the ends of the probes become too close to each other or to the patient's tissue or organs.

As described herein, the computing devices and systems described and/or illustrated herein broadly represent any type or form of computing device, processor or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Graphic Processing Units (GPUs), Tensor Processing Units (TPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor, processors, or computing device or devices as disclosed herein can be configured with executable instructions to perform any one or more steps of any method as disclosed herein. This may be accomplished by programming a processor with a set of computer-executable instructions. When executed, the instructions will cause the processor or a computing device of which a processor is an element to implement one or more steps or stages of the methods described herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

As used herein, the terms "coarse" and "gross" are used interchangeably.

As used herein, the terms "one or more computing devices" and "processor" are used interchangeably.

The present disclosure includes the following numbered clauses.

Clause 1. A system for treating or imaging tissue of a patient, said system comprising: a probe sized for insertion into the patient; a robotic arm configured to couple to the probe; one or more computing devices operatively coupled to the robotic arm and configured with instructions for: establishing an allowable range of motion for the probe, the allowable range of motion stored on a memory of the one or more computing devices, wherein establishing the allowable range of motion further comprises defining a possible range of motion for a distal end of the probe; and modifying the possible range of motion of the distal end of the probe to define an allowable range of motion for the distal end of the probe; treating or imaging the target tissue of the patient with the probe; and moving the robotic arm to affect movement of the probe within the allowable range of motion for the probe.

Clause 2. The system of clause 1, wherein defining a possible range of motion for a distal end of the probe further comprises defining a region within which the distal end of the probe is capable of moving.

Clause 3. The system of clause 2, wherein the region is defined by a mathematical representation of the region.

Clause 4. The system of clause 2, wherein the region is defined by an image of the region, the image including dimensions of the probe and the possible angular movement of the distal end of the probe.

Clause 5. The system of clause 1, wherein the probe is an imaging probe and the system further comprises a treatment probe sized for insertion into the patient.

Clause 6. The system of clause 5, wherein modifying the possible range of motion of the distal end of the probe to define an allowable range of motion further comprises activating and performing a training or teaching mode for the system, the training or teaching mode comprising a user manipulating one or both of the imaging or treatment probes to define a limit on the possible range of motion of the distal end of one or both of the imaging or treatment probes.

Clause 7. The system of clause 6, wherein the training or teaching mode is conducted when both probes are outside of the patient.

Clause 8. The system of clause 6, wherein the training or teaching mode is conducted when both probes are inside of the patient.

Clause 9. The system of clause 8, further comprising operating the imaging probe to obtain an image of the treatment probe, and in response to the image, constraining the allowable range of motion of the distal end of the treatment probe.

Clause 10. The system of clause 8, further comprising operating the imaging probe to obtain an image of the treatment probe, and in response to the image, constraining the allowable range of motion of the distal end of the imaging probe.

Clause 11. The system of clause 10, further comprising operating the imaging probe to obtain an image of the treatment probe, and in response to the image, automatically moving the distal end of the imaging probe within a predetermined area to avoid collision with the treatment probe.

Clause 12. The system of clause 8, further comprising operating the imaging probe to obtain an image of the patient's anatomy, and in response to the image, constraining the allowable range of motion of the distal end of the imaging probe.

Clause 13. The system of clause 1, wherein modifying the possible range of motion of the distal end of the probe comprises comparing the possible range of motion to a scan of the patient showing an area of the patient's anatomy near a treatment site and modifying the possible range of motion to avoid harm to the patient from the distal end of the probe in a region around the treatment site.

Clause 14. The system of clause 12, further comprising processing the obtained image using an image recognition application to identify an organ or region of tissue of the patient.

Clause 15. A method of treating target tissue at a target site of a patient, said method comprising: manually inserting a probe into the patient; coupling the probe to a robotic arm; establishing an allowable range of motion for the probe, the allowable range of motion stored on a memory of one or more computing devices operably coupled with the robotic arm, wherein establishing the allowable range of motion further comprises defining a possible range of motion for a distal end of the probe; and modifying the possible range of motion of the distal end of the probe to define an allowable range of motion for the distal end of the probe; treating or imaging the target tissue of the patient with the probe; and moving the robotic arm under control of the one or more computing devices operably coupled with the probe, to affect movement of the probe within the allowable range of motion for the probe.

Clause 16. The method of clause 15, wherein defining a possible range of motion for a distal end of the probe further comprises defining a region within which the distal end of the probe is capable of moving.

Clause 17. The method of clause 16, wherein the region is defined by a mathematical representation of the region.

Clause 18. The method of clause 16, wherein the region is defined by an image of the region, the image including dimensions of the probe and the possible angular movement of the distal end of the probe.

Clause 19. The method of clause of claim 15, wherein the probe is an imaging probe and the system further comprises a treatment probe sized for insertion into the patient.

Clause 20. The method of clause 19, wherein modifying the possible range of motion of the distal end of the probe to define an allowable range of motion further comprises activating and performing a training or teaching mode for the system, the training or teaching mode comprising a user manipulating one or both of the imaging or treatment probes to define a limit on the possible range of motion of the distal end of one or both of the imaging or treatment probes.

Clause 21. The method of clause 20, wherein the training or teaching mode is conducted when both probes are outside of the patient.

Clause 22. The method of clause 21, wherein the training or teaching mode defines a range of motion of the first probe relative to the second probe, with the defined range of motion able to be stored in memory and translatable to inside of the patient.

Clause 23. The method of clause 21, wherein the training or teaching mode is conducted when both probes are inside of the patient.

Clause 24. The method of clause 23, further comprising operating the imaging probe to obtain an image of the treatment probe, and in response to the image, constraining the allowable range of motion of the distal end of the treatment probe.

Clause 25. The method of clause 23, further comprising operating the imaging probe to obtain an image of the treatment probe, and in response to the image, constraining the allowable range of motion of the distal end of the imaging probe.

Clause 26. The method of clause 23, further comprising operating the imaging probe to obtain an image of the treatment probe, and in response to the image, performing one or more of: defining a region or volume to prevent a collision of the probes with each other or a distance to maintain between the probes to protect against probe collision related tissue damage; confirming the position of one or both probes within the defined region; or monitoring the position of one or both probes and activating a motion of a robotic arm to prevent a collision.

Clause 27. The method of clause 23, further comprising operating the imaging probe to obtain an image of the patient's anatomy, and in response to the image, constraining the allowable range of motion of the distal end of the imaging probe.

Clause 28. The method of clause 15, wherein modifying the possible range of motion of the distal end of the probe comprises comparing the possible range of motion to a scan of the patient showing an area of the patient's anatomy near a treatment site and modifying the possible range of motion to avoid harm to the patient from the distal end of the probe in a region around the treatment site.

Clause 29. The method of clause 27, further comprising processing the obtained image using an image recognition application to identify an organ or region of tissue of the patient Clause 30. A system for treating target tissue at a target site of a patient, the system comprising: a first robotic arm coupled to a treatment probe for treating the target tissue of the patient; a second robotic arm coupled to an imaging probe for imaging the target tissue of the patient; and one or more computing devices operably coupled with the first robotic arm and the second robotic arm, the one or more computing devices configured to execute instructions for controlling movement of one or more of the first robotic arm or the second robotic arm, wherein the instructions constrain the movement of one or both probes to be within an allowable range of motion for the probe or probes.

Clause 31. The system of clause 30, wherein the one or more computing devices are configured to execute instructions for controlling the movement of the first robotic arm or the second robotic arm to adjust one or more of a pitch, yaw, roll, lateral, or linear position of the treatment probe or the imaging probe along an axis of entry of the treatment probe or the imaging probe into the patient.

Clause 32. The system of clause 30, wherein the instructions for constraining the movement of one or both probes to be within an allowable range of motion for the probe or probes further include instructions for defining a possible range of motion for a distal end of at least one of the probes and modifying the possible range of motion of the distal end of the probe to define an allowable range of motion for the distal end of the probe.

Clause 33. The system of clause 32, wherein defining a possible range of motion for a distal end of the probe further comprises defining a region within which the distal end of the probe is capable of moving.

Clause 34. The system of clause 33, wherein the region is defined by a mathematical representation of the region.

Clause 35. The system of clause 33, wherein the region is defined by an image of the region, the image including dimensions of the probe and the possible angular movement of the distal end of the probe.

Clause 36. The system of clause 32, wherein modifying the possible range of motion of the distal end of the probe to define an allowable range of motion further comprises activating and performing a training or teaching mode for the system, the training or teaching mode comprising a user manipulating one or both of the imaging or treatment probes to define a limit on the possible range of motion of the distal end of one or both of the imaging or treatment probes.

Clause 37. The system of clause 36, wherein the training or teaching mode is conducted when both probes are outside of the patient.

Clause 38. The system of clause 36, wherein the training or teaching mode is conducted when both probes are inside of the patient.

Clause 39. The system of clause 38, further comprising operating the imaging probe to obtain an image of the treatment probe, and in response to the image, constraining the allowable range of motion of the distal end of the treatment probe.

Clause 40. The system of clause 38, further comprising operating the imaging probe to obtain an image of the treatment probe, and in response to the image, constraining the allowable range of motion of the distal end of the imaging probe.

Clause 41. The system of clause 38, further comprising operating the imaging probe to obtain an image of the patient's anatomy, and in response to the image, constraining the allowable range of motion of the distal end of the imaging probe.

Clause 42. The system of clause 30, wherein modifying the possible range of motion of the distal end of the probe comprises comparing the possible range of motion to a scan of the patient showing an area of the patient's anatomy near a treatment site and modifying the possible range of motion to avoid harm to the patient from the distal end of the probe in a region around the treatment site.

Clause 43. The system of clause 41, further comprising processing the obtained image using an image recognition application to identify an organ or region of tissue of the patient.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for treating or imaging tissue of a patient, said system comprising:
   a probe sized for insertion into the patient;
   a robotic arm configured to couple to the probe;
   one or more computing devices operatively coupled to the robotic arm and configured with instructions for:
   executing a training mode in response to a request from an operator of the system, wherein the training mode comprises the operator demonstrating an allowable range of motion of a distal end of the probe with the distal end of the probe inserted into a body of the patient;
   exiting the training mode; and
   treating or imaging the tissue of the patient with the probe after insertion of the distal end of the probe into the body of the patient, wherein the
   robotic arm is caused to affect movement of the distal end of the probe within the body of the patient only within the allowable range of motion for the distal end of the probe.

2. The system of claim 1, wherein prior to executing the training mode, the system defines an initial range of motion for the distal end of the probe by defining a region within which the distal end of the probe is confined to move.

3. The system of claim 2, wherein the region is defined by a mathematical representation of the region.

4. The system of claim 2, wherein the region is defined by an image of the region, the image including dimensions of the probe and a possible angular movement of the distal end of the probe.

5. The system of claim 1, wherein the probe is an imaging probe and the system further comprises a treatment probe sized for insertion into the patient.

6. The system of claim 5, wherein the training mode comprises the operator manipulating one or both of the imaging probe or treatment probe to define a limit on the allowable range of motion of the distal end of said one or both of the imaging probe or the treatment probe.

7. The system of claim 6, wherein the training mode is conducted when both probes are inside of the patient.

8. The system of claim 7, wherein the instructions further cause the system to operate the imaging probe to obtain an image of the treatment probe, and in response to the image, constrain the allowable range of motion of the distal end of the treatment probe.

9. The system of claim 7, wherein the instructions further cause the system to operate the imaging probe to obtain an image of the treatment probe, and in response to the image, constrain the allowable range of motion of the distal end of the imaging probe.

10. The system of claim 9, wherein the instructions further cause the system to operate the imaging probe to obtain an image of the treatment probe, and in response to the image, automatically move the distal end of the imaging probe within a predetermined area to avoid collision with the treatment probe.

11. The system of claim 7, wherein the instructions further cause the system to operate the imaging probe to obtain an image of the patient's anatomy, and in response to the image, modifying the allowable range of motion of the distal end of the imaging probe.

12. The system of claim 11, wherein the instructions further cause the system to process the image of the patient's anatomy using an image recognition application to identify an organ or region of tissue of the patient.

13. The system of claim 1, wherein the instructions further cause the system to compare the allowable range of motion to a scan of the patient showing an area of the patient's anatomy near a treatment site and in response modify the allowable range of motion of the distal end of the probe in a region around the treatment site.

14. A method of treating target tissue at a target site of a patient, said method comprising:
manually inserting a distal end of a probe into the patient;
coupling the probe to a robotic arm;
executing a training mode, wherein the training mode comprises an operator defining an allowable range of motion of a distal end of the probe;
exiting the training mode; and
treating or imaging the target tissue of the patient with the probe after insertion of the distal end of the probe into a body of the patient, wherein
the robotic arm under control of one or more computing devices operably coupled with the probe is caused to affect movement of the distal end of the probe within the allowable range of motion for the distal end of the probe.

15. The method of claim 14, wherein prior to executing the training mode, a system defines an initial range of motion for the distal end of the probe by defining a region within which the distal end of the probe is confined to move.

16. The method of claim 15, wherein the region is defined by a mathematical representation of the region.

17. The method of claim 15, wherein the region is defined by an image of the region, the image including dimensions of the probe and a possible angular movement of the distal end of the probe.

18. The method of claim 14, wherein the probe is an imaging probe and the system further comprises a treatment probe sized for insertion into the patient.

19. The method of claim 18, wherein the training mode comprises the operator manipulating one or both of the imaging probe or the treatment probe to define the allowable range of motion of the distal end of said one or both of the imaging probe or the treatment probe.

20. The method of claim 14, further comprising comparing the allowable range of motion to a scan of the patient showing an area of the patient's anatomy near a treatment site and in response modifying the allowable range of motion of the distal end of the probe in a region around the treatment site.

* * * * *